US008916517B2

(12) United States Patent
Coy et al.

(10) Patent No.: US 8,916,517 B2
(45) Date of Patent: Dec. 23, 2014

(54) ANALOGS OF PITUITARY ADENYLATE CYCLASE-ACTIVATING POLYPEPTIDE (PACAP) AND METHODS FOR THEIR USE

(75) Inventors: David H. Coy, New Orleans, LA (US); Jerome L. Maderdrut, New Orleans, LA (US); Min Li, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 13/505,370

(22) PCT Filed: Nov. 2, 2010

(86) PCT No.: PCT/US2010/055164
§ 371 (c)(1),
(2), (4) Date: Nov. 21, 2012

(87) PCT Pub. No.: WO2011/054001
PCT Pub. Date: May 5, 2011

(65) Prior Publication Data
US 2013/0065816 A1    Mar. 14, 2013

Related U.S. Application Data

(60) Provisional application No. 61/280,298, filed on Nov. 2, 2009.

(51) Int. Cl.
| *A61K 38/17* | (2006.01) |
| *C07K 14/435* | (2006.01) |
| *A61P 11/00* | (2006.01) |
| *A61P 13/12* | (2006.01) |
| *A61P 1/00* | (2006.01) |
| *A61P 27/02* | (2006.01) |
| *A61P 37/06* | (2006.01) |
| *A61P 9/00* | (2006.01) |
| *A61P 9/12* | (2006.01) |
| *A61P 35/00* | (2006.01) |
| *A61P 3/04* | (2006.01) |
| *A61P 3/10* | (2006.01) |
| *A61K 45/06* | (2006.01) |
| *C07K 14/575* | (2006.01) |
| *A61K 33/24* | (2006.01) |
| *A61K 38/00* | (2006.01) |

(52) U.S. Cl.
CPC ............... *A61K 33/24* (2013.01); *A61K 45/06* (2013.01); *C07K 14/57563* (2013.01); *A61K 38/00* (2013.01)
USPC ......... 514/1.4; 514/21.3; 514/13.2; 514/15.4; 514/15.7; 514/16.4; 514/16.6; 514/16.9; 514/17.1; 514/17.7; 514/17.8; 514/17.9; 514/18.6; 514/19.3; 514/19.6; 514/1.7; 514/1.8; 514/1.9; 514/20.8; 514/4.3; 514/4.9; 514/6.9; 514/7.3; 530/324

(58) Field of Classification Search
CPC ... A61K 33/24; A61K 2300/00; A61K 38/00; A61K 45/06; C07K 14/57563
USPC ............. 514/1.4, 13.2, 15.4, 15.7, 16.4, 16.6, 514/16.9, 17.1, 17.7, 17.8, 17.9, 18.6, 19.3, 514/19.6, 1.7, 1.8, 1.9, 20.8, 21.3, 4.3, 4.9, 514/6.9, 7.3; 530/324
See application file for complete search history.

(56) References Cited

U.S. PATENT DOCUMENTS

| 4,526,938 | A | 7/1985 | Churchill et al. |
| 4,980,286 | A | 12/1990 | Morgan et al. |
| 5,128,242 | A | 7/1992 | Arimura et al. |
| 5,128,326 | A | 7/1992 | Balazs et al. |
| 5,198,542 | A | 3/1993 | Onda et al. |
| 5,436,146 | A | 7/1995 | Shenk et al. |
| 5,679,377 | A | 10/1997 | Bernstein et al. |
| 5,708,022 | A | 1/1998 | Bastos et al. |
| 5,912,015 | A | 6/1999 | Bernstein et al. |
| 5,916,597 | A | 6/1999 | Lee et al. |
| 5,989,463 | A | 11/1999 | Tracy et al. |
| 6,242,563 | B1 | 6/2001 | Dong |

(Continued)

FOREIGN PATENT DOCUMENTS

| EP | 0467279 A2 | 1/1992 |
| WO | WO-91/05548 A1 | 5/1991 |

(Continued)

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*

(Continued)

*Primary Examiner* — Julie Ha
*Assistant Examiner* — Erinne Dabkowski
(74) *Attorney, Agent, or Firm* — Clark & Elbing LLP; Paul T. Clark, Esq.; Todd Armstrong

(57) ABSTRACT

This invention relates to novel analogs of pituitary adenylate cyclase-activating polypeptide (PACAP), which are agonists for the PACAP/vasoactive intestinal peptide (VIP) receptors: PAC1, VPAC1 and VPAC2 receptors. These PACAP analogs can be used as prophylactic/therapeutic agents for a wide range of medical disorders, including (but not limited to) cancer and autoimmune disease. These PACAP analogs can be coupled to suitable radionuclides and used in the localization, diagnosis and treatment of disseminated cancers and metastatic tumors, or coupled to small molecule therapeutics and used as vectors for targeted drug delivery. This invention also provides pharmaceutical compositions of one or more PACAP-like compounds of the invention either alone or in combination with one or more other prophylactic/therapeutic agents.

12 Claims, 10 Drawing Sheets

(56) References Cited

U.S. PATENT DOCUMENTS

| | | | |
|---|---|---|---|
| 6,680,295 | B1 | 1/2004 | Arimura |
| 6,855,308 | B2 | 2/2005 | Thakur |
| 2004/0038888 | A1 | 2/2004 | Mercer et al. |
| 2008/0108573 | A1 | 5/2008 | Duggan |
| 2008/0227954 | A1 | 9/2008 | Larsen |
| 2008/0312157 | A1 | 12/2008 | Levy et al. |

FOREIGN PATENT DOCUMENTS

| | | | |
|---|---|---|---|
| WO | WO-92/06180 | A1 | 4/1992 |
| WO | WO-92/22635 | A1 | 12/1992 |
| WO | WO-93/14188 | A1 | 7/1993 |
| WO | WO-93/20221 | A1 | 10/1993 |
| WO | WO-94/12649 | A2 | 6/1994 |
| WO | WO-96/09064 | A1 | 3/1996 |
| WO | WO-96/20698 | A2 | 7/1996 |
| WO | WO-99/15154 | A1 | 4/1999 |
| WO | WO-99/20253 | A1 | 4/1999 |
| WO | WO-03/061680 | A2 | 7/2003 |
| WO | WO-03/092716 | A2 | 11/2003 |
| WO | WO-2005/120545 | A1 | 12/2005 |
| WO | WO-2006/012394 | A1 | 2/2006 |
| WO | WO-2007/021498 | A1 | 2/2007 |
| WO | WO-2009/033767 | A2 | 3/2009 |
| WO | WO-2010/036936 | A2 | 4/2010 |
| WO | WO-2011/054001 | A2 | 5/2011 |
| WO | WO-2011/097581 | A2 | 8/2011 |

OTHER PUBLICATIONS

Patrick Robberecht, Structural requirements for the occupancy of pituitary adenylate-cyclase-activating-peptide (PACAP) receptors and adenylate cyclase activation in human neuroblastoma NB-OK-1 cell membranes, 1992, Eur. J. Biochem. 207, 239-246.*
English Translation of Office Action for Chinese Patent Application No. 201080060381.2, mailed Jul. 12, 2013 (7 pages).
English Translation of Search Report for Chinese Patent Application No. 201080060381.2, dated Jul. 3, 2013 (2 pages).
Hou et al., "Structural requirements for the occupancy of rat brain PACAP receptors and adenylate cyclase activation," Neuropharmacology. 33(10):1189-1195 (1994).
Sun et al., "Solution structure and mutational analysis of pituitary adenylate cyclase-activating polypeptide binding to the extracellular domain of PAC1-RS," Proc Natl Acad Sci USA. 104(19):7875-7880 (2007).
Extended European Search Report for European Application No. 10827667.6, dated Jul. 23, 2013 (8 pages).
Kalhs et al. "Microangiopathy following allogeneic marrow transplantation. Association with cyclosporine and methylprednisolone for graft-versus-host disease prophylaxis" Transplantation. 60(9):949-57 (1995).
Ohtaki et al. "Role of PACAP in ischemic neural death" J Mol Neurosci. 36(1-3):16-25 (2008).
Serkova et al. "Cyclosporine Neurotoxicity" Mol Interven. 4(2):97-107 (2004).
Truwit et al. "MR imaging of reversible cyclosporin A-induced neurotoxicity" AJNR Am J Neuroradiol. 12(4):651-9 (1991).
Office Action in Chinese Patent Application No. 201080060381.2 mailed Apr. 11, 2014 (with English translation) (12 pages).
Alessandrini, "Experimental researches on heart and lung preservation," Acta Biomed Ateneo Parmense. 65(3-4):59-73 (Abstract only) (1994).
Allam, "Vasoactive intestinal peptide inhibits liver pathology in acute murine schistosomiasis mansoni and modulates IL-10, IL-12 and TNF-alpha production," Immunobiology. 212(8):603-612 (2007).
Altschul et al., "Basic local alignment search tool," J Mol Biol. 215(3):403-410 (1990).
Altschul et al., "Gapped Blast and PSI-Blast: a new generation of protein database search programs," Nucleic Acids Res. 25(17):3389-3402 (1997).
Ameen et al., "CFTR channel insertion to the apical surface in rat duodenal villus epithelial cells is upregulated by VIP in vivo," J Cell Sci. 112:887-894 (1999).
Arimura, "PACAP functions as a neurotrophic factor," Ann NY Acad Sci. 739:228-243 (1994).
Arimura, "Perspectives on pituitary adenylate cyclase activating polypeptide (PACAP) in the neuroendocrine, endocrine, and nervous systems," Jpn J Physiol. 48(5):301-331 (1998).
Arimura, "Pituitary adenylate cyclase activating polypeptide (PACAP): discovery and current status of research," Regul Pept. 37(3):287-303 (1992).
Arimura, "Receptors for pituitary adenylate cyclase-activating polypeptide: comparison with vasoactive intestinal peptide receptors," Trends Endocrinol Metab. 3(8):288-294 (1992).
Atlasz et al., "Extent of retinal damage in carotid artery occlusion-induced hypoperfusion model in PACAP-deficient mice," J Mol Neurosci. 42:266-318 (Abstract only) (2010).
Azuma et al., "PACAP protects mice with dextran sodium sulfate-induced acute colitis," J Mol Neurosci. 42:266-318 (Abstract only) (2010).
Azuma et al., "Regulation of somatolactin release from cultured goldfish pituitary cells by PACAP and MCH," J Mol Neurosci. 42:266-318 (Abstract only) (2010).
Bacus et al., "Biological grading of breast cancer using antibodies to proliferating cells and other markers," Am J Pathol. 135(5):783-792 (1989).
Banks et al., "Passage of pituitary adenylate cyclase activating polypeptide1-27 and pituitary adenylate cyclase activating polypeptide1-38 across the blood-brain barrier," J Pharmacol Exp Ther. 267(2):690-696 (1993).
Banks, "PACAP and the blood-brain barrier," J Mol Neurosci. 42:266-318 (Abstract only) (2010).
Barnes et al., "Glucocorticoid resistance in inflammatory diseases," Lancet. 373(9678):1905-1917 (2009).
Boesen et al., "Circumvention of chemotherapy-induced myelosuppression by transfer of the mdr1 gene," Biotherapy. 6:291-302 (1994).
Botia et al., "Neuroprotective effects of PACAP against alcohol toxicity in the developing rat cerebellum," J Mol Neurosci. 42:266-318 (Abstract only) (2010).
Boudard et al., "Inhibition of mouse T-cell proliferation by CGRP and VIP: effects of these neuropeptides on IL-2 production and cAMP synthesis," J Neurosci Res. 29(1):29-41 (1991).
Bourgault et al., "Novel stable PACAP analogs with potent activity towards the PAC1 receptor," *Peptides*. 29(6):919-32 (2008).
Brenneman et al., "Chemokine release is associated with the protective action of PACAP-38 against HIV envelope protein neurotoxicity," Neuropeptides. 36(4):271-280 (2002).
Brenner et al., "Glomeruli and blood pressure. Less of one, more the other?," Am J Hypertens. 1:335-347 (1988).
Buchwald et al., "Long-term, continuous intravenous heparin administration by an implantable infusion pump in ambulatory patients with recurrent venous thrombosis," Surgery. 88(4):507-516 (1980).
Buscail et al., "Stimulation of rat pancreatic tumoral AR4-2J cell proliferation by pituitary adenylate cyclase-activating peptide," Gastroenterology. 103(3):1002-1008 (1992).
Campana et al., "Double and triple staining methods for studying the proliferative activity of human B and T lymphoid cells," J Immunol Methods. 107(1):79-88 (1988).
Castorina et al., "PACAP and VIP prevent apoptosis in schwannoma cells," Brain Res. 1241:29-35 (2008).
Cederbaum et al., "Role of oxidative stress in alcohol-induced liver injury," Arch Toxicol. 83(6):519-548 (2009).
Ceponis et al. "Epithelial cell signaling responses to enterohemorrhagic *Escherichia coli* infection," Mem Inst Oswaldo Cruz. 100(Suppl 1):199-203 (2005).
Chandler, "Possible mechanisms of bleomycin-induced fibrosis," Clin Chest Med. 11(1):21-30 (1990).
Chang, "Experimental study of the effects of pituitary adenylate cyclase-activating polypeptide (PACAP) and its mechanism on the vascular cell components—the possible relationship between PACAP and atherosclerosis," Sheng Li Ke Xue Jin Zhan. 28:132-135 (Abstract only ) (1997).

(56) References Cited

OTHER PUBLICATIONS

Chen et al., "Effects of ectopic overexpression of p21(WAF1/CIP1) on aneuploidy and the malignant phenotype of human brain tumor cells," Oncogene. 13(7):1395-1403 (1996).
Chiodera et al., "Effects of intravenously infused pituitary adenylate cyclase-activating polypeptide on adenohypophyseal Hormone secretion in normal men," Neuroendocrinology. 64(3):242-246 (1996).
Cleek et al., "Biodegradable polymeric carriers for bFGF antibody for cardiovascular application," Pro Intl Symp Control Rel Bioact Mater. 24:853-854 (1997).
Clowes et al., "Long-term biological response of injured rat carotid artery seeded with smooth muscle cells expressing retrovirally introduced human genes," J Clin Invest. 93(2):644-651 (1994).
Cotten et al., "Receptor-mediated transport of DNA into eukaryotic cells," Methods Enzymol. 217:618-644 (1993).
David et al., Society for Neuroscience (33rd Annual Meeting), New Orleans, Louisiana, #38.1 (2003) (Abstract).
Decourt et al., "Complete primary sequences of two lambda immunoglobulin light chains in myelomas with nonamyloid (Randall-type) light chain deposition disease," Am J Pathol. 153(1):313-318 (1998).
Dejda et al., "Involvement of stathmin 1 in the neurotrophic effects of PACAP in PC12 cells," J Mol Neurosci. 42:266-318 (Abstract only) (2010).
Delgado et al., "Vasoactive intestinal peptide and pituitary adenylate cyclase-activating polypeptide inhibit nuclear factor-kB-dependent gene activation at multiple levels in the human monocytic cell line THP-1," J Biol Chem. 276(1):369-380 (2001).
Doan et al., "Design of PAC1/VPAC1 selective analogs as multifunctional drug candidates for the treatment of Parkinson's disease," J. of Peptide Science. 16(S1): 153-154 (2010).
Doan et al., "Key pharmacophore elements of the N-terminal domain of PACAP," J Mol Neurosci. 42:266-318 (Abstract only) (2010).
Doberer et al., "Pulmonary and systemic effects of inhaled PACAP38 in healthy male subjects," Eur J Clin Invest. 37(8):665-672 (2007).
Dufes et al., "Effects of the vasoactive intestinal peptide (VIP) and related peptides on glioblastoma cell growth in vitro" J Mol Neurosci. 21(2):91-102 (2003).
During et al., Controlled release of dopamine from a polymeric brain implant: in vivo characterization, Ann Neurol. 25(4):351-356 (1989).
Dérand et al., "Activation of VPAC1 receptors by VIP and PACAP-27 in human bronchial epithelial cells induces CFTR-dependent chloride secretion," Br J Pharmacol. 141(4):698-708 (2004).
Eiden et al., "PACAP signaling to target genes through cyclic AMP and calcium during the stress response," J Mol Neurosci. 42:266-318 (Abstract only) (2010).
Eiden et al., "Signaling pathways involved in PACAP and cytokine interactions regulating adrenomedullary neuropeptide biosynthesis," J Mol Neurosci. 42:266-318 (Abstract only) (2010).
Ferencz et al., "Comparison of intestinal warm ischemic injury on PACAP knock-out and wild-type mice," J Mol Neurosci. 42:266-318 (Abstract only) (2010).
Ferencz et al., "Influence of PACAP on oxidative stress and tissue injury following small-bowel autotransplantation," J Mol Neurosci. 37(2):168-176 (2009).
Figiel et al., "Pituitary adenylate cyclase-activating polypeptide (PACAP), a neuron-derived peptide regulating glial glutamate transport and metabolism," J Neurosci. 20(10):3596-3605 (2000).
Filipsson et al. "Pituitary adenylate cyclase-activating polypeptide stimulates insulin and glucagon secretion in humans," J Clin Endocrinol Metab. 82(9):3093-3098 (1997).
Fukuchi et al., "Pituitary adenylate cyclase-activating polypeptide (PACAP) induces activity-dependent gene expressions in neurons," J Mol Neurosci. 42:266-318 (Abstract only) (2010).
Ganea et al., "Vasoactive intestinal peptide (VIP) and pituitary adenylate cyclase-activating polypeptide (PACAP) as modulators of both innate and adaptive immunity," Crit Rev Oral Biol Med. 13(3):229-237 (2002).
Gasz et al., "Pituitary adenylate cyclase activating polypeptide protects cardiomyocytes against oxidative stress-induced apoptosis," Peptides. 27(1):87-94 (2006).
Girard et al., "Expression and regulation of PACAP/VIP and receptors in micturition reflex pathways of nerve growth factor (NGF) overexpressing (OE) mice," J Mol Neurosci. 42:266-318 (Abstract only) (2010).
Girard et al., "Presence of VIP, PACAP, and their receptors in control and explants cultured mouse major pelvic ganglia," J Mol Neurosci. 42:266-318 (Abstract only) (2010).
Goldspiel et al., "Human gene therapy," Clin Pharm. 12(7):488-505 (1993).
Gottschall et al., "Characterization and distribution of binding sites for the hypothalamic peptide, pituitary adenylate cyclase-activating polypeptide," Endocrinology. 127(1):272-277 (1990).
Gozes et al., "Davunetide (NAP intranasal formulation AL-108) provides cognitive protection in a model of microtubules dysfunction exhibiting schizophrenia-like symptoms," J Mol Neurosci. 42:266-318 (Abstract only) (2010).
Grammas et al., "PACAP38 protects rat cortical neurons against the neurotoxicity evoked by sodium nitroprusside and thrombin," J Mol Neurosci. 42:266-318 (Abstract only) (2010).
Greenstein et al., "Characterization of the MM.1 human multiple myeloma (MM) cell lines: a model system to elucidate the characteristics, behavior, and signaling of steroid-sensitive and -resistant MM cells," Exp Hematol. 31(4):271-282 (2003).
Grossman et al., "Retroviruses: delivery vehicle to the liver," Curr Opin Genet Dev. 3(1):110-114 (1993).
Gupta, "Intrinsic multidrug resistance phenotype of Chinese hamster (rodent) cells in comparison to human cells," Biochem Biophys Res Commun. 153(2):598-605 (1988).
Gutiérrez-Cañas et al., "VIP and PACAP are autocrine factors that protect the androgen-independent prostate cancer cell line PC-3 from apoptosis induced by serum withdrawal," Br J Pharmacol. 139(5):1050-1058 (2003).
Haberl et al., "Vasoactive intestinal peptide gene alterations in patients with idiopathic pulmonary arterial hypertension," Eur J Hum Genet. 15(1):18-22 (2007).
Hagino, "PAC1-R heterozygous mice have no desire to explore the unknown environment in memory task," J Mol Neurosci. 42:266-318 (Abstract only) (2010).
Hammack, "A role for pituitary adenylate cyclase-activating peptide (PACAP) expression and signaling in the bed nucleus of the stria terminalis (BNST) in stress-induced anxiety-like behavior," J Mol Neurosci. 42:266-318 (Abstract only) (2010).
Hammack et al., "Pituitary adenylate cyclase-activating peptide (PACAP) expression and signaling in the bed nucleus of the stria terminalis (BNST) mediate increased anxiety-like behavior following chronic variate stress," J Mol Neurosci. 42:266-318 (Abstract only) (2010).
Harper et al., "The p21 Cdk-interacting protein Cip 1 is a potent inhibitor of G1 cyclin-dependent kinases," Cell. 75(4):805-816 (1993).
Hatanaka et al., "Identification of a novel-signaling cascade specifically involved in the light-induced phase advance of circadian rhythm by using PACAP knockout mice," J Mol Neurosci. 42:266-318 (Abstract only) (2010).
Hawke et al., "PACAP neurons in the hypothalamic ventromedial nucleus are targets of central leptin signaling," J Neurosci. 29(47):14828-14835 (2009).
Hayata et al., "PACAP plays a crucial role in the stress-induced activation of HPA-axis," J Mol Neurosci. 42:266-318 (Abstract only) (2010).
Hayez et al., "The neuropeptides vasoactive intestinal peptide (VIP) and pituitary adenylate cyclase activating polypeptide (PACAP) modulate several biochemical pathways in human leukemic myeloid cells," J Neuroimmunol. 149(1-2):167-181 (2004).
Hideshima et al., "Targeting p38 MAPK inhibits multiple myeloma cell growth in the bone marrow milieu," Blood. 101(2):703-705 (2003).
Hogle, "Cytoprotective agents used in the treatment of patients with cancer," Semin Oncol Nurs. 23(3):213-224 (2007).

(56) References Cited

OTHER PUBLICATIONS

Hoist et al., "Increased plasma levels of vasoactive intestinal polypeptide in pre-eclampsia," Br J Obstet Gynaecol. 98(8):803-806 (1991).
Horvath et al., "PACAP protects renal cells against in vitro ischemia and oxidative stress in primary kidney cultures," J Mol Neurosci. 42:266-318 (Abstract only) (2010).
Horvath et al., "The role of endogenous PACAP in protection against hypoxia and oxidative stress: in vitro studies in PACAP knockout mice," J Mol Neurosci. 42:266-318 (Abstract only) (2010).
Hoshino et al., "S-phase fraction of human brain tumors in situ measured by uptake of bromodeoxyuridine," Int J Cancer. 38(3):369-374 (1986).
Howard et al., "Intracerebral drug delivery in rats with lesion-induced memory deficits," J Neurosurg. 71(1):105-112 (1989).
Ikeda et al., "Involvement of pituitary adenylate cyclase-activating polypeptide (PACAP) in diabetic neuropathy of streptozotocin (STZ) treated mice," J Mol Neurosci. 42:266-318 (Abstract only) (2010).
Ishido, "Temporal dynamics of gene expression during PACAP-induced PC12 cell differentiation," J Mol Neurosci. 42:266-318 (Abstract only) (2010).
Ishihama et al., "Effects of environmental factors during development on abnormal phenotypes in PACAP knock-out mice," J Mol Neurosci. 42:266-318 (Abstract only) (2010).
Jeoung et al., "Effects of tumor necrosis factor-alpha on antimitogenicity and cell cycle-related proteins in MCF-7 cells," J Biol Chem. 270(31):18367-18373 (1995).
Juarranz et al., "Vasoactive intestinal peptide (VIP) stimulates rat prostatic epithelial cell proliferation," Prostate. 47(4):285-292 (2001).
Karlin et al., "Applications and statistics for multiple high-scoring segments in molecular sequences," Proc Natl Acad Sci USA. 90(12):5873-5877 (1993).
Karlin et al., "Methods for assessing the statistical significance of molecular sequence features by using general scoring schemes," Proc Natl Acad Sci USA. 87(6):2264-2268 (1990).
Kawano et al., "Autocrine generation and requirement of BSF-2/IL-6 for human multiple myelomas," Nature. 332(6159):83-85 (1988).
Kiem et al., "Retrovirus-mediated gene transduction into canine peripheral blood repopulating cells," Blood. 83(6): 1467-1473 (1994).
Kinhult et al., "Pituitary adenylate cyclase-activating peptide inhibits neutrophil chemotaxis," Peptides. 22(12): 2151-2154 (2001).
Kintzel, "Anticancer drug-induced kidney disorders," Drug Saf. 24(1):19-38 (2001).
Kiss et al., "Comparison and possible relationship between PACAP- and enriched environment-induced retinal protection in MSG-treated newborn rats," J Mol Neurosci. 42:266-318 (Abstract only) (2010).
Kitada et al., "Synthesis and structure-activity relationships of PACAP," Peptide Chemistry, Y. Shimonishi 239-244 (1990).
Koller et al., "Inactivating the beta 2-microglobulin locus in mouse embryonic stem cells by homologous recombination," Proc Natl Acad Sci USA. 86(22):8932-8935 (1989).
Kong et al., "Reduction of lipopolysaccharide-induced neurotoxicity in mixed cortical neuron/glia cultures by femtomolar concentrations of pituitary adenylate cyclase-activating polypeptide," Neuroscience. 91(2):493-500 (1999).
Kono et al., "Diphenyleneiodonium sulfate, an NADPH oxidase inhibitor, prevents early alcohol-induced liver injury in the rat," Am J Physiol Gastrointest Liver Physiol. 280(5):G1005-G1012 (2001).
Kucher et al. "Histopathologic comparison of nephrogenic fibrosing dermopathy and scleromyxedema," J Cutan Path. 32(7):484-490 (2005).
Langer, "New methods of drug delivery," Science. 249(4976):1527-33 (1990).
Le et al., "PAC1 and PACAP expression, signaling, and effect on the growth of HCT8, human colonic tumor cells," Regul Pept. 109(1-3):115-125 (2002).

Lee et al., "Analysis of a putative VPAC2 receptor from sturgeon shed light on molecular and functional evolution of VPAC2R in vertebrates," J Mol Neurosci. 42:266-318 (Abstract only) (2010).
Lee et al., "Neutrophil activation and production of reactive oxygen species in pre-eclampsia," J Hypertens. 21(2):395-402 (2003).
Leister et al., "Vasoactive intestinal polypeptide and gastrin-releasing peptide attenuate hepatic microvasculatory disturbances following intestinal ischemia and reperfusion," Digestion. 66(3):186-192 (2002).
Lelièvre et al., "Differential expression and function of PACAP and VIP receptors in four human colonic adenocarcinoma cell lines," Cell Signal. 10(1):13-26 (1998).
Levy et al., "Inhibition of calcification of bioprosthetic heart valves by local controlled-release diphosphonate," Science. 228(4696):190-192 (1985).
Leyton et al., "PACAP(6-38) inhibits the growth of prostate cancer cells," Cancer Lett. 125(1-2):131-139 (1998).
Leyton et al., "PACAP(6-38) is a PACAP receptor antagonist for breast cancer cells," Breast Cancer Res Treat. 56(2):177-186 (1999).
Li et al., "Intravenous infusion of pituitary adenylate cyclase-activating polypeptide (PACAP) in a patient with multiple myeloma and myeloma kidney: a case study," Peptides. 28(9):1891-1895 (2007).
Li et al., "Pituitary adenylate cyclase-activating polypeptide precursor is processed solely by prohormone convertase 4 in the gonads," Endocrinology. 141(10):3723-3730 (2000).
Li et al., "Prohormone convertases 1 and 2 process ProPACAP and generate matured, bioactive PACAP38 and PACAP27 in transfected rat pituitary GH4C1 cells," Neuroendocrinology. 69(3):217-226 (1999).
Li et al., "Renoprotection by pituitary adenylate cyclase-activating polypeptide in multiple myeloma and other kidney diseases," Regul Pept. 145(1-3):24-32 (2008).
Li et al., "Renoprotection with PACAP in cisplatin-induced acute kidney injury," J Mol Neurosci. 42:266-318 (Abstract only) (2010).
Li et al., "Signaling cascades involved in neuroprotection by subpicomolar pituitary adenylate cyclase-activating polypeptide 38," J Mol Neurosci. 27(1):91-105 (2005).
Li et al., "Subcellular distribution of p21 and PCNA in normal and repair-deficient cells following DNA damage" Curr Biol. 6(2):189-199 (1996).
Lu et al., "Paradoxical effects of PACAP and VIP on gastrointestinal physiology," J Mol Neurosci. 42:266-318 (Abstract only) (2010).
Luo et al., "Vasoactive intestinal peptide attenuates concanavalin A-mediated liver injury," Eur J Pharmacol. 607(1-3):226-233 (2009).
Lutz et al., "LIF-mediated maintenance of PACAP-induced neurite outgrowths in human SH-SY5Y neuroblastoma cells require PI3K but not STAT or ERK signaling pathways," J Mol Neurosci. 42:266-318 (Abstract only) (2010).
Maderdrut et al., "Pituitary adenylate cyclase-activating polypeptide (PACAP) analogs increase the therapeutic index of anticancer agents for blood cancers," J Mol Neurosci. 42:266-318 (Abstract only) (2010).
Martinez et al., "Anti-inflammatory role in septic shock of pituitary adenylate cyclase-activating polypeptide receptor," Proc Natl Aced Sci USA 99(2):1053-1058 (2002).
Mastrangeli et al., "Diversity of airway epithelial cell targets for in vivo recombinant adenovirus-mediated gene transfer" J Clin Invest. 91(1):225-234 (1993).
Matsuda et al., "Regulation of feeding behavior by pituitary adenylate cyclase-activating polypeptide (PACAP) and vasoactive intestinal polypeptide (VIP) in vertebrates," Peptides. 28(9):1761-1766 (2007).
Matsuda, et al., "PACAP stimulates somatolacin release from cultured goldfish pituitary cells," Abstracts, 9th International Symposium on VIP, PACAP, and Related Peptides, Kagoshima, Japan, Oct. 5-8, 2009; J Mol Neurosci. 42:286 (2010).
Miura et al., "Regulatory mechanism of PAC1 gene expression by nerve growth factor (NGF) in PC12 cells," J Mol Neurosci. 42:266-318 (Abstract only) (2010).
Miyata et al., "Isolation of a neuropeptide corresponding to the N-terminal 27 residues of the pituitary adenylate cyclase activating polypeptide with 38 residues (PACAP38)," Biochem Biophys Res Commun. 170(2):643-648 (1990).

(56) References Cited

OTHER PUBLICATIONS

Miyata et al., "Isolation of a novel 38 residue-hypothalamic polypeptide which stimulates adenylate cyclase in pituitary cells," Biochem Biophys Res Commun. 164(1):567-574 (1989).
Molnar et al., "The role of the circulatory system in the transportation of PACAP-like compounds in earthworms," J Mol Neurosci. 42:266-318 (Abstract only) (2010).
Mori et al., "Endogenous PACAP attenuated doxorubicin-induced myocardial damage," S.E. *Abstracts*, 9th International Symposium on VIP, PACAP, and Related Peptides, Kagoshima, Japan, Oct. 5-8, 2009; J Mol Neurosci. 42:295 (2010).
Mounien et al., "Pituitary adenylate cyclase-activating polypeptide inhibits food intake in mice through activation of the hypothalamic melanocortin system," Neuropsychopharmacology. 34(2):424-435 (2009).
Mukohyama et al., "The inhibitory effects of vasoactive intestinal peptide and pituitary adenylate cyclase-activating polypeptide on osteoclast formation are associated with upregulation of osteoprotegerin and downregulation of RANKL and RANK," Biochem Biophys Res Commun. 271(1):158-163 (2000).
Mulligan, "The basic science of gene therapy," Science. 260(5110):926-932 (1993).
Murck et al., "Pituitary adenylate cyclase-activating peptide affects homeostatic sleep regulation in healthy young men," Am J Physiol Endocrinol Metab. 292(3):E853-E857 (2007).
Nagata et al., "PACAP/VIP inhibits osteoblastic differentiation and stimulates the cytokine production of IL-6 through VPAC2 receptor in MC3T3 cells," *Abstracts*, 9th International Symposium on VIP, PACAP, and Related Peptides, Kagoshima, Japan, Oct. 5-8, 2009; J Mol Neurosci. 42:285-6 (2010).
Nakagawa et al., "Pituitary adenylate cyclase activating polypeptide (PACAP) enhances blood-brain barrier (BBB) functions of rat brain microvascular endothelial cells in vitro," J Mol Neurosci. 42:266-318 (Abstract only) (2010).
Nakamachi et al., "Effect of PACAP on tear secretion in mouse," *Abstracts*, 9th International Symposium on VIP, PACAP, and Related Peptides, Kagoshima, Japan, Oct. 5-8, 2009; J Mol Neurosci. 42:293 (2010).
Nakata et al., "Intra-islet PACAP protects pancreatic beta-cells against glucotoxicity and lipotoxicity," J Mol Neurosci. 42:266-318 (Abstract only) (2010).
Ng et al., "Molecular cloning and characterization of a VPAC receptor in the inshore hagfish, *Eptatretus burgeri*," J Mol Neurosci. 42:266-318 (Abstract only) (2010).
Ning et al., "Intratumoral radioimmunotherapy of a human colon cancer xenograft using a sustained-release gel," Radiother Oncol. 39(2):179-189 (1996).
Nonaka et al., "Delivery of pituitary adenylate cyclase-activating polypeptide (PACAP) to the brain: targeting with intranasal delivery and cyclodextrins," *Abstracts*, 9th International Symposium on VIP, PACAP, and Related Peptides, Kagoshima, Japan, Oct. 5-8, 2009; J Mol Neurosci. 42:281-2 (2010).
Ogi et al., "Molecular cloning and functional expression of a cDNA encoding a human pituitary adenylate cyclase activating polypeptide receptor," Biochem Biophys Res Commun. 196(3):1511-1521 (1993).
Ohtaki et al., "Neuroprotective strategy on brain injuries by immunemodulation-lesson from PACAP and hMSCs on stroke," *Abstracts*, 9th International Symposium on VIP, PACAP, and Related Peptides, Kagoshima, Japan, Oct. 5-8, 2009; J Mol Neurosci. 42:281 (2010).
Oka et al., "Pituitary adenylate cyclase-activating polypeptide inhibits transforming growth factor-beta1-induced apoptosis in a human pituitary adenoma cell line," Am J Pathol. 155(6):1893-1900 (1999).
Okazaki et al., "Expression of human pituitary adenylate cyclase activating polypeptide (PACAP) cDNA in CHO cells and characterization of the products," FEBS Lett. 298(1):49-56 (1992).
Onoue et al., "Pituitary adenylate cyclase-activating polypeptide attenuates streptozotoc-ininduced apoptotic death of RIN-m5F cells through regulation of Bcl-2 family protein mRNA expression," FEBS J. 275(22):5542-5551 (2008).
Ottaway et al., "Interaction of vasoactive intestinal peptide with mouse lymphocytes: specific binding and the modulation of mitogen responses," J Immunol. 132(1):417-423 (1984).
Otto et al., "Pulmonary hypertension and right heart failure in pituitary adenylate cyclase-activating polypeptide type I receptor-deficient mice," Circulation. 110(20):3245-3251 (2004).
Paran et al., "Extensive colonic ischemia following treatment with bevacizumab, fluouracil and CPT-11 in a young patient with advanced adenocarcinoma of the rectum" Isr Med Assoc J. 9(6):488-9 (2007).
Pirger et al., "Memory, cAMP, and PACAP—a phylogenetically conserved function? Studies in *Lymnea stagnalis* ," J Mol Neurosci. 42:266-318 (Abstract only) (2010).
Racz et al., "Effects of PACAP on mitochondrial antiapoptotic pathways and cytokine expression in rats subjected to renal ischemia/reperfusion," J Mol Neurosci. 42:266-318 (Abstract only) (2010).
Rafferty et al., "Rescue of functional F508del cystic fibrosis transmembrane conductance regulator by vasoactive intestinal peptide in the human nasal epithelial cell line JME/CF15," J Pharmacol Exp Ther. 331(1):2-13 (2009).
Raoult et al., "Tissue-type plasminogen activator (tPA) as a PACAP-regulated gene in neuronal cells," J Mol Neurosci. 42:266-318 (Abstract only) (2010).
Reglodi et al. "Pituitary adenylate cyclase activating polypeptide protects dopaminergic neurons and improves behavioral deficits in a rat model of parkinson's disease," Behav Brain Res. 151(1-2):303-312 (2004).
Reglodi et al., "Delayed systemic administration of PACAP38 is neuroprotective in transient middle cerebral artery occlusion in the rat," Stroke. 31(6):1411-1417 (2000).
Reglodi, et al. "Review of the retinoprotective effects of PACAP," *Abstracts*, 9th International Symposium on VIP, PACAP, and Related Peptides, Kagoshima, Japan, Oct. 5-8, 2009; J Mol Neurosci. 42:282-3 (2010).
Reubi, "Peptide receptors as molecular targets for cancer diagnosis and therapy," Endocr Rev. 24(4):389-427 (2003).
Riera et al., "The enhancement of endogenous cAMP with pituitary adenylate cyclase-activating polypeptide protects rat kidney against ischemia through the modulation of inflammatory response," Transplantation. 72(7):1217-1223 (2001).
Rosenfeld et al., "Adenovirus-mediated transfer of a recombinant alpha 1-antitrypsin gene to the lung epithelium in vivo," Science. 252(5004):431-434 (1991).
Rosenfeld et al., "In vivo transfer of the human cystic fibrosis transmembrane conductance regulator gene to the airway epithelium," Cell. 68(1):143-155 (1992).
Rácz et al., "Protective effects of pituitary adenylate cyclase activating polypeptide in endothelial cells against oxidative stress-induced apoptosis," Gen Comp Endocrinol. 153:115-123 (2007).
Said et al., "Moderate pulmonary arterial hypertension in male mice lacking the vasoactive intestinal peptide gene," Circulation. 115(10):1260-1268 (2007).
Said, S. "An update on VIP in health disease," *Abstracts*, 9th International Symposium on VIP, PACAP, and Related Peptides, Kagoshima, Japan, Oct. 5-8, 2009; J Mol Neurosci. 42:294 (2010).
Sakiyama et al., "Structure-activity relationship of pituitary adenylate cyclase activating polypeptide (PACAP)," Pep Chem. 215-220 (1991).
Sakurai et al., "The roles of pancreatic PACAP in cerulein-inducded pancreatitis," J Mol Neurosci. 42:266-318 (Abstract only) (2010).
Salmons et al., "Targeting of retroviral vectors for gene therapy," Hum Gene Ther. 4(2):129-141, (1993).
Sandor et al., "Impaired nocifensive behaviors and mechanical hyperalgesia, but enhanced thermal hyperalgesia in PACAP knock-out mice," J Mol Neurosci. 42:266-318 (Abstract only) (2010).
Sano et al., "The effect of pituitary adenylate cyclase activating polypeptide on cultured rat cardiocytes as a cardioprotective factor," Regul Pept. 109(1-3):107-113 (2002).

(56) References Cited

OTHER PUBLICATIONS

Sato et al., "Suppression of oxidative stress by PACAP," J Mol Neurosci. 42:266-318 (Abstract only) (2010).
Saudek et al., "A preliminary trial of the programmable implantable medication system for insulin delivery," N Engl J Med. 321(9):574-579 (1989).
Segre et al., "Receptors for secretin, calcitonin, parathyroid hormone (PTH)/PTH-related peptide, vasoactive intestinal peptide, glucagon-like peptide 1, growth hormone-releasing hormone, and glucagon belong to a newly discovered G-protein-linked receptor family," Trends Endocrinol Metab. 4(10):309-314 (1993).
Sergejeva et al., "A synthetic VIP peptide analogue inhibits neutrophil recruitment in rat airways in vivo," Regul Pept. 117(2):149-154 (2004).
Shen et al., "Roles of the PAC1 receptor in mouse neurogenesis," Abstracts, 9th International Symposium on VIP, PACAP, and Related Peptides, Kagoshima, Japan, Oct. 5-8, 2009; J Mol Neurosci. 42:280 (2010).
Sherwood et al., "The origin and function of the pituitary adenylate cyclase-activating polypeptide (PACAP)/glucagon superfamily," Endocr Rev. 21(6):619-670 (2000).
Shibata et al., "15-Deoxy-Δ-prostaglandin J$_2$ enhances NGF-induced neurite outgrowth in PC12 cells via a CRTH2 receptor-p38 MAP kinase pathway," J Mol Neurosci. 42:266-318 (Abstract only) (2010).
Shintani, N. "Altered emotional and cognitive function in PACAP-deficient mice: a novel animal model for psychiatric disorder," Abstracts, 9th International Symposium on VIP, PACAP, and Related Peptides, Kagoshima, Japan, Oct. 5-8, 2009; J Mol Neurosci. 42:278-9 (2010).
Shivers et al., "Two high affinity binding sites for pituitary adenylate cyclase-activating polypeptide have different tissue distributions," Endocrinology. 128(6):3055-65 (1991).
Sreedharan et al., "Structure, expression, and chromosomal localization of the type I human vasoactive intestinal peptide receptor gene," Proc Natl Acad Sci USA. 92(7):2939-2943 (1995).
Steenstrup et al., "Pituitary adenylate cyclase activating polypeptide (PACAP): occurrence and vasodilatory effect in the human uteroplacental unit," Regul Pept. 61(3):197-204 (1996).
Sugawara et al., "The alternative regulation of pituitary adenylate cyclase-activating polylpeptide (PACAP) gene expression by neural-restrictive silencer," J Mol Neurosci. 42:266-318 (Abstract only) (2010).
Svoboda et al., "Molecular cloning and functional characterization of a human VIP receptor from SUP-T1 lymphoblasts," Biochem Biophys Res Commun. 205(3):1617-1624 (1994).
Szabadfi et al., "Effects of PACAP in streptozotocin-induced rat model of diabetic retinophathy," J Mol Neurosci. 42:266-318 (Abstract only) (2010).
Szakaly et al., "The in vivo role of endogenous PACAP kidney ischemia/reperfusion: studies with knockout mice and radioimmunoassay," J Mol Neurosci. 42:266-318 (Abstract only) (2010).
Szakaly et al.,"Effects of PACAP on survival and renal morphology in rats subjected to renal ischemia/reperfusion," J Mol Neurosci. 36(1-3):89-96 (2008).
Takemura et al., "Doxorubicin-induced cardiomyopathy from the cardiotoxic mechanisms to management," Prog Cardiocasc Dis. 49(5):330-352 (2007).
Tamas et al., "PACAP-38 in human plasma and milk under physiological and pathological conditions: introductory measurements for possible future clinical diagnostic application," J Mol Neurosci. 42:266-318 (Abstract only) (2010).
Tamas et al., "Protective effects of PACAP against oxidative stress in cochlear cells," J Mol Neurosci. 42:266-318 (Abstract only) (2010).
Tatsuno et al., "Inhibition of mitogen-stimulated proliferation of murine splenocytes by a novel neuropeptide, pituitary adenylate cyclase activating polypeptide: a comparative study with vasoactive intestinal peptide," Endocrinology. 128(2):728-734 (1991).
Thakur et al., "Regulation of macrophage activation in alcoholic liver disease," J Gastrogenterol Hepatol. 22(Suppl 1):S53-S56 (2007).
Tominaga et al., "The cell specific promoter in upstream region of human PACAP testis-specific exon," J Mol Neurosci. 42:266-318 (Abstract only) (2010).
Trejter et al., "Studies on the involvement of endogenous neuropeptides in the control of thymocyte proliferation in the rat," Histol Histopathol. 16(1):155-158 (2001).
Turner et al., "Treatment of human prostate cancer cells with dolastatin 10, a peptide isolated from a marine shell-less mollusc," Prostate. 34(3):175-181 (1998).
Uchida et al., "Cytoprotective action of pituitary adenylate cyclase activating polypeptide (PACAP) in ischemia-induced neuronal cell death in rat hippocampus," Soc Neurosci. 20:Abstract No. 193.10 (1994).
Uchida et al., "Prevention of ischemia-induced death of hippocampal neurons by pituitary adenylate cyclase activating polypeptide," Brain Res. 736(1-2):280-286 (1996).
Ushiyama et al., "Alternative splicing of the pituitary adenylate cyclase-activating polypeptide (PACAP) receptor contributes to function of PACAP-27," Abstracts, 9th International Symposium on VIP, PACAP, and Related Peptides, Kagoshima, Japan, Oct. 5-8, 2009; J Mol Neurosci. 42:290 (2010).
Valiante et al., "Localization of pituitary adenylate cyclase-activating polypeptide (PACAP) receptors in peripheral tissues during mouse perinatal development," J Mol Neurosci. 42:266-318 (Abstract only) (2010).
Valiante et al., "Pituitary adenylate cyclase-activating polypeptide (PACAP) receptor expression is altered in the brain of *Podarcis sicula* after nonylphenol administration," Abstracts, 9th International Symposium on VIP, PACAP, and Related Peptides, Kagoshima, Japan, Oct. 5-8, 2009; J Mol Neurosci. 42:283 (2010).
Valiante et al., "Pituitary adenylate cyclase-activating polypeptide and its receptors in diet-induced obese rat adrenal glands," J Mol Neurosci. 42:266-318 (Abstract only) (2010).
Vallejo, M. "PACAP as a neurotrophic signal for astrocyte differentiation," Abstracts, 9th International Symposium on VIP, PACAP, and Related Peptides, Kagoshima, Japan, Oct. 5-8, 2009; J Mol Neurosci. 42:280 (2010).
Vassilev et al., "The levels of ubiquitinated histone H2A are highly upregulated in transformed human cells: partial colocalization of uH2A clusters and PCNA/cyclin foci in a fraction of cells in S-phase," J Cell Sci. 108(Pt 3):1205-1215 (1995).
Vaudry et al., "Pituitary adenylate cyclase-activating polypeptide and its receptors: from structure to functions," Pharmacol Rev. 52:269-324 (2000).
Watanabe et al., "PACAP stimulates catecholamine release from adrenal medulla: a novel noncholinergic secretagogue," Am J Physiol. 269(5 Pt 1):E903-E909 (1995).
Winding et al. "Pituitary adenylyl cyclase-activating polypeptides and vasoactive intestinal peptide inhibit bone resorption by isolated rabbit osteoclasts," Exp Physiol. 82(5):871-886 (1997).
Wu et al., "Comparative analysis of cortical gene expression in mouse models of Alzheimer's disease," Neurobiol Aging. 27(3):377-386 (2006).
Wu et al., "Receptor-mediated in vitro gene transformation by a soluble DNA carrier system," J Biol Chem. 262(10):4429-4432 (1987).
Yamada et al., "Increased stathmin 1 expression in the dentate gyrus causes abnormal axonal arborizations potential relevance to schizophrenia," J Mol Neurosci. 42:266-318 (Abstract only) (2010).
Yang et al., "Pituitary adenylate cyclase-activating polypeptide (PACAP) 38 and PACAP4-6 are neuroprotective through inhibition of NADPH oxidase: potent regulators of microglia-mediated oxidative stress," J Pharmacol Exp Ther. 319(2):595-603 (2006).
Yang et al., "The activation of PACAP receptor (PAC1 receptor) differentially targets NR2A containing NMDA receptors and favors LTP induction," J Mol Neurosci. 42:266-318 (Abstract only) (2010).
Zabalou et al., "A three-season comparative analysis of the chromosomal distribution of P and hobo mobile elements in a natural population of *Drosophila melanogaster*," Hereditas. 120(2):127-140 (1994).
Zhu et al., "Heteromeric Kv1 potassium channel expression: amino acid determinants involved in processing and trafficking to the cell surface," J Biol Chem. 278(28):25558-25567 (2003).

(56) References Cited

OTHER PUBLICATIONS

Zia et al., "Pituitary adenylate cyclase activating peptide receptors regulate the growth of non-small cell lung cancer cells," Cancer Res. 55(21): 4886-91 (1995).

Zijlstra et al., "Germ-line transmission of a disrupted $\beta_2$-microglobulin gene produced by homologous recombination in embryonic stem cells," Nature. 342(6248):435-438 (1989).

English Translation of Office Action for Chinese Patent Application No. 200980145368.4, mailed Nov. 27, 2013 (8 pages).

English Translation of Office Action for Japanese Patent Application No. 2007-522734, mailed Jul. 11, 2011 (8 pages).

English Translation of the Notification of the Second Office Action for Chinese Patent Application No. 200980145368.4, mailed Apr. 18, 2013 (7 pages).

Extended European Search Report for European Patent Application No. 05791771.8, dated Jun. 5, 2009 (13 pages).

Extended European Search Report for European Patent Application No. 11740499.6, dated Sep. 13, 2013 (5 pages).

International Preliminary Report on Patentability and Written Opinion of the International Searching Authority for International Application No. PCT/US2005/025836, issued Jan. 27, 2007 (4 pages).

International Preliminary Report on Patentability and Written Opinion of the International Searching Authority for International Application No. PCT/US2009/058445, mailed Apr. 30, 2010 (4 pages).

International Search Report for International Application No. PCT/US2005/25836, mailed Jan. 4, 2006 (1 page).

International Preliminary Report on Patentability and Written Opinion of the International Searching Authority for International Application No. PCT/US2010/055164, dated May 8, 2012 (8 pages).

International Search Report for International Application No. PCT/US2010/055164, mailed Jul. 29, 2011 (6 pages).

Office Action for Canadian Patent Application No. 2,574,709, dated Apr. 19, 2012 (6 pages).

Office Action in Japanese Patent Application No. 2011-529275 mailed Dec. 17, 2013 (with English Translation) (6 pages).

\* cited by examiner

Figure 1

His-Ser-Asp-Gly-Ile-Phe-Thr-Asp-Ser-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-NH$_2$ (SEQ ID NO:1)

His-Ser-Asp-Gly-Ile-Phe-Thr-Asp-Ser-Tyr-Arg-Lys-Gln-Met-Ala-Val-Lys-Lys-Tyr-Leu-Ala-Ala-Val-Leu-NH$_2$ (SEQ ID NO:2)

His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-NH$_2$ (SEQ ID NO:3)

His-Ser-Pip-Gly-Ile-Phe-Thr-Asp-Ser-Tyr-Ser-Arg-Tyr-Arg-Lys-Aib-Ala-Ala-Val-Lys-Lys-Tyr-Leu-Ala-Ala-Val-Leu-Aib-Lys-Arg-Tyr-Lys-Gln-Lys-Val-Lys-Asn-D-Lys-NH$_2$ (SEQ ID NO:4)

His-Ser-Pip-Gly-Ile-Phe-Thr-Asp-Ser-Tyr-Ser-Arg-Tyr-Arg-Lys-Aib-Ala-Ala-Val-Lys-Lys-Tyr-Leu-Ala-Ala-Val-Leu-Aib-Lys-Arg-Tyr-Lys-Gln-Lys-Val-Lys-Asn-D-Lys-NH$_2$ (SEQ ID NO:5)

His-Ser-Pip-Gly-Ile-Phe-Thr-Asp-Ser-Tyr-Ser-Arg-Tyr-Arg-Lys-Aib-Ala-Ala-Val-Lys-Lys-Tyr-Ala-Ala-Ala-Val-Leu-Aib-Lys-Arg-Tyr-Lys-Gln-Lys-Val-Lys-Asn-D-Lys-NH$_2$ (SEQ ID NO:6)

His-Ser-Pip-Gly-Ile-Phe-Thr-Asp-Ser-Tyr-Ser-Arg-Tyr-Arg-Lys-Aib-Ala-Ala-Val-Ala-Lys-Tyr-Leu-Ala-Ala-Val-Leu-Aib-Lys-Arg-Tyr-Lys-Gln-Lys-Val-Lys-Asn-D-Lys-NH$_2$ (SEQ ID NO:7)

His-Ser-Pip-Gly-Ile-Phe-Thr-Asp-Ser-Tyr-Ser-Arg-Tyr-Arg-Lys-Aib-Ala-Ala-Val-Lys-Lys-Tyr-Leu-Ala-Ala-Val-Leu-Aib-Lys-Arg-Tyr-Lys-Gln-Lys-Val-Lys-Asn-D-Lys-NH$_2$ (SEQ ID NO:8)

His-Ser-Pip-Gly-Ile-Phe-Thr-Asp-Ser-Tyr-Ser-Arg-Tyr-Arg-Lys-Aib-Ala-Ala-Val-Lys-Lys-Tyr-Leu-Ala-Ala-Val-Leu-NH$_2$ (SEQ ID NO:9)

N-acety-His-Ser-Pip-Gly-Ile-Phe-Thr-Asp-Ser-Tyr-Ser-Arg-Tyr-Arg-Lys-Aib-Ala-Ala-Val-Lys-Lys-Tyr-Leu-Ala-Ala-Val-Leu-NH$_2$ (SEQ ID NO:10)

His-Ala-Pip-Gly-Ile-Phe-Thr-Asp-Ser-Tyr-Arg-Lys-Gln-Met-Ala-Val-Lys-Lys-Tyr-Leu-Ala-Ala-Val-Leu-NH$_2$ (SEQ ID NO:11)

His-Ser-Pip-Gly-Ile-Phe-Thr-Asp-Ser-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-NH$_2$ (SEQ ID NO:12)

Figure 2

MALDI/MS-Determined and Calculated Molecular Weights

| Peptide | MALDI/MS | Calculated |
|---|---|---|
| [Pip$^3$,Aib$^{16,28}$,Ala$^{17}$,Lys$^{34}$,D-Lys$^{38}$]PACAP38 | 4426 | 4428 |
| [Pip$^3$,Ala$^{15,17}$,Aib$^{16,28}$,Lys$^{34}$,D-Lys$^{38}$]PACAP38 | 4370 | 4371 |
| [Pip$^3$,Ala$^{14,17}$,Aib$^{16,28}$,Lys$^{34}$,D-Lys$^{38}$]PACAP38 | 4342 | 4343 |
| [Pip$^3$,Aib$^{16,28}$,Ala$^{17,21}$,Lys$^{34}$,D-Lys$^{38}$]PACAP38 | 4369 | 4371 |
| [Pip$^3$,Aib$^{16,28}$,Ala$^{17,20}$,Lys$^{34}$,D-Lys$^{38}$]PACAP38 | 4365 | 4371 |
| [Pip$^3$,Aib$^{16}$,Ala$^{17}$]PACAP27 | 3039 | 3041 |
| N-acetyl[Pip$^3$,Aib$^{16}$,Ala$^{17}$]PACAP27 | 3079 | 3083 |
| [Ala$^{2,17}$,Pip$^3$,Aib$^{16}$]PACAP27 | 3023 | 3025 |
| [Pip$^3$]PACAP38 | 4531 | 4532 |
| N-acetyl[Pip$^3$]PACAP38 | 4573 | 4574 |

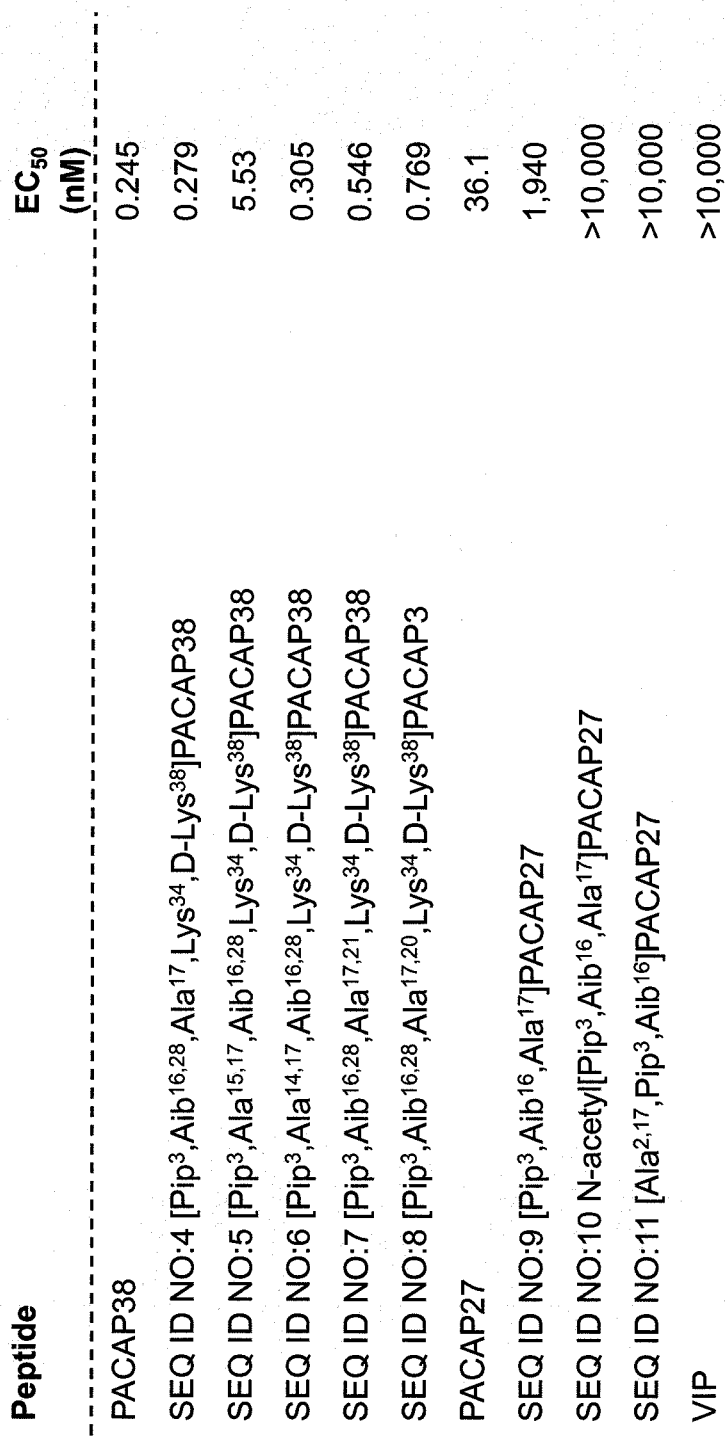

Figure 3

| Peptide | Inhibition of Myeloma Cell Proliferation EC$_{50}$ (nM) |
|---|---|
| PACAP38 | 0.245 |
| SEQ ID NO:4 [Pip$^3$,Aib$^{16,28}$,Ala$^{17}$,Lys$^{34}$,D-Lys$^{38}$]PACAP38 | 0.279 |
| SEQ ID NO:5 [Pip$^3$,Ala$^{15,17}$,Aib$^{16,28}$,Lys$^{34}$,D-Lys$^{38}$]PACAP38 | 5.53 |
| SEQ ID NO:6 [Pip$^3$,Ala$^{14,17}$,Aib$^{16,28}$,Lys$^{34}$,D-Lys$^{38}$]PACAP38 | 0.305 |
| SEQ ID NO:7 [Pip$^3$,Aib$^{16,28}$,Ala$^{17,21}$,Lys$^{34}$,D-Lys$^{38}$]PACAP38 | 0.546 |
| SEQ ID NO:8 [Pip$^3$,Aib$^{16,28}$,Ala$^{17,20}$,Lys$^{34}$,D-Lys$^{38}$]PACAP3 | 0.769 |
| PACAP27 | 36.1 |
| SEQ ID NO:9 [Pip$^3$,Aib$^{16}$,Ala$^{17}$]PACAP27 | 1,940 |
| SEQ ID NO:10 N-acetyl[Pip$^3$,Aib$^{16}$,Ala$^{17}$]PACAP27 | >10,000 |
| SEQ ID NO:11 [Ala$^{2,17}$,Pip$^3$,Aib$^{16}$]PACAP27 | >10,000 |
| VIP | >10,000 |

SEQUENCE LISTING

```
<160> NUMBER OF SEQ ID NOS: 16

<210> SEQ ID NO 1
<211> LENGTH: 38
<212> TYPE: PRT
<213> ORGANISM: Homo sapiens

<400> SEQUENCE: 1

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 2
<211> LENGTH: 27
<212> TYPE: PRT
<213> ORGANISM: Homo sapiens

<400> SEQUENCE: 2

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 3
<211> LENGTH: 28
<212> TYPE: PRT
<213> ORGANISM: Homo sapiens

<400> SEQUENCE: 3

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 4
<211> LENGTH: 38
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Pipecolic acid
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (28)..(28)
<223> OTHER INFORMATION: Alpha-aminoisobutyric acid
<220> FEATURE:
<221> NAME/KEY: MOD_RES
<222> LOCATION: (38)..(38)
<223> OTHER INFORMATION: D-Lysine

<400> SEQUENCE: 4

His Ser Xaa Gly Ile Phe Thr Asp Ser Tyr Ser Arg Tyr Arg Lys Xaa
1               5                   10                  15

Ala Ala Val Lys Lys Tyr Leu Ala Ala Val Leu Xaa Lys Arg Tyr Lys
            20                  25                  30

Gln Lys Val Lys Asn Lys
        35

<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Pipecolic acid
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (28)..(28)
<223> OTHER INFORMATION: Alpha-aminoisobutyric acid
<220> FEATURE:
<221> NAME/KEY: MOD_RES
<222> LOCATION: (38)..(38)
<223> OTHER INFORMATION: D-Lysine

<400> SEQUENCE: 5

His Ser Xaa Gly Ile Phe Thr Asp Ser Tyr Ser Arg Tyr Arg Ala Xaa
1               5                   10                  15

Ala Ala Val Lys Lys Tyr Leu Ala Ala Val Leu Xaa Lys Arg Tyr Lys
            20                  25                  30

Gln Lys Val Lys Asn Lys
        35

<210> SEQ ID NO 6
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Pipecolic acid
```

```
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (28)..(28)
<223> OTHER INFORMATION: Alpha-aminoisobutyric acid
<220> FEATURE:
<221> NAME/KEY: MOD_RES
<222> LOCATION: (38)..(38)
<223> OTHER INFORMATION: D-Lysine

<400> SEQUENCE: 6

His Ser Xaa Gly Ile Phe Thr Asp Ser Tyr Ser Arg Tyr Ala Lys Xaa
1               5                   10                  15

Ala Ala Val Lys Lys Tyr Leu Ala Ala Val Leu Xaa Lys Arg Tyr Lys
            20                  25                  30

Gln Lys Val Lys Asn Lys
        35

<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Pipecolic acid
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (28)..(28)
<223> OTHER INFORMATION: Alpha-aminoisobutyric acid
<220> FEATURE:
<221> NAME/KEY: MOD_RES
<222> LOCATION: (38)..(38)
<223> OTHER INFORMATION: D-Lysine

<400> SEQUENCE: 7

His Ser Xaa Gly Ile Phe Thr Asp Ser Tyr Ser Arg Tyr Arg Lys Xaa
1               5                   10                  15

Ala Ala Val Lys Ala Tyr Leu Ala Ala Val Leu Xaa Lys Arg Tyr Lys
            20                  25                  30

Gln Lys Val Lys Asn Lys
        35

<210> SEQ ID NO 8
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Pipecolic acid
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (28)..(28)
```

```
<223> OTHER INFORMATION: Alpha-aminoisobutyric acid
<220> FEATURE:
<221> NAME/KEY: MOD_RES
<222> LOCATION: (38)..(38)
<223> OTHER INFORMATION: D-Lysine

<400> SEQUENCE: 8

His Ser Xaa Gly Ile Phe Thr Asp Ser Tyr Ser Arg Tyr Arg Lys Xaa
1               5                   10                  15

Ala Ala Val Ala Lys Tyr Leu Ala Ala Val Leu Xaa Lys Arg Tyr Lys
            20                  25                  30

Gln Lys Val Lys Asn Lys
        35

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pipecolic acid
<220> FEATURE:
<221> NAME/KEY: MOD_RES
<222> LOCATION: (16)..(16)
<223> OTHER INFORMATION: Alpha-aminoisobutyric acid

<400> SEQUENCE: 9

His Ser Xaa Gly Ile Phe Thr Asp Ser Tyr Ser Arg Tyr Arg Lys Xaa
1               5                   10                  15

Ala Ala Val Lys Lys Tyr Leu Ala Ala Val Leu
            20                  25

<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-acetyl-Histidine
<220> FEATURE:
<221> NAME/KEY: MOD_RES
<222> LOCATION: (3)..(3)
<223> OTHER INFORMATION: Pipecolic acid
<220> FEATURE:
<221> NAME/KEY: MOD_RES
<222> LOCATION: (16)..(16)
<223> OTHER INFORMATION: Alpha-aminoisobutyric acid

<400> SEQUENCE: 10

His Ser Xaa Gly Ile Phe Thr Asp Ser Tyr Ser Arg Tyr Arg Lys Xaa
1               5                   10                  15

Ala Ala Val Lys Lys Tyr Leu Ala Ala Val Leu
            20                  25

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Pipecolic acid
<220> FEATURE:
<221> NAME/KEY: MOD_RES
<222> LOCATION: (16)..(16)
<223> OTHER INFORMATION: Alpha-aminoisobutyric acid

<400> SEQUENCE: 11

His Ala Xaa Gly Ile Phe Thr Asp Ser Tyr Ser Arg Tyr Arg Lys Xaa
1               5                   10                  15

Ala Ala Val Lys Lys Tyr Leu Ala Ala Val Leu
            20                  25

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Pipecolic acid

<400> SEQUENCE: 12

His Ser Xaa Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: N-acetyl-Histidine
<220> FEATURE:
<221> NAME/KEY: MOD_RES
<222> LOCATION: (3)..(3)
<223> OTHER INFORMATION: Pipecolic acid

<400> SEQUENCE: 13

His Ser Xaa Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 14
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (3)..(3)
<223> OTHER INFORMATION: Nipecotic acid
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (28)..(28)
<223> OTHER INFORMATION: Alpha-aminoisobutyric acid
<220> FEATURE:
<221> NAME/KEY: MOD_RES
<222> LOCATION: (38)..(38)
<223> OTHER INFORMATION: D-Lysine

<400> SEQUENCE: 14

His Ser Xaa Gly Ile Phe Thr Asp Ser Tyr Ser Arg Tyr Arg Lys Xaa
1               5                   10                  15

Ala Ala Val Lys Lys Tyr Leu Ala Ala Val Leu Xaa Lys Arg Tyr Lys
            20                  25                  30

Gln Lys Val Lys Asn Lys
        35

<210> SEQ ID NO 15
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Isonipecotic acid
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (28)..(28)
<223> OTHER INFORMATION: Alpha-aminoisobutyric acid
<220> FEATURE:
<221> NAME/KEY: MOD_RES
<222> LOCATION: (38)..(38)
<223> OTHER INFORMATION: D-Lysine

<400> SEQUENCE: 15

His Ser Xaa Gly Ile Phe Thr Asp Ser Tyr Ser Arg Tyr Arg Lys Xaa
1               5                   10                  15

Ala Ala Val Lys Lys Tyr Leu Ala Ala Val Leu Xaa Lys Arg Tyr Lys
            20                  25                  30

Gln Lys Val Lys Asn Lys
        35

<210> SEQ ID NO 16
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Xaa is His, D-His, Tyr, D-Tyr, Trp, D-Trp, Pal,
      or D-Pal
<220> FEATURE:
<221> NAME/KEY: MOD_RES
<222> LOCATION: (1)..(1)
<223> OTHER INFORMATION: The residue at position 1 can be modified to
```

-continued

```
      include H, (C1-C18)alkyl, or CO(C1-C18)alkyl, or the modification
      is omitted
<220> FEATURE:
<221> NAME/KEY: MOD_RES
<222> LOCATION: (2)..(2)
<223> OTHER INFORMATION: Xaa is Ser, D-Ser, hSer, N-Me-Ser, Thr, D-Thr,
      Ala, D-Ala, Ile, D-Ile, Pro, D-Pro, Abu, Aib, Acb, Ach, Acpe, or
      Acpr
<220> FEATURE:
<221> NAME/KEY: MOD_RES
<222> LOCATION: (3)..(3)
<223> OTHER INFORMATION: Xaa is Pip
<220> FEATURE:
<221> NAME/KEY: MOD_RES
<222> LOCATION: (4)..(4)
<223> OTHER INFORMATION: Xaa is Gly, Ala, D-Ala, beta-Ala, Gaba, Abu,
      Aib, Acb, Ach, Acpe, or Acpr
<220> FEATURE:
<221> NAME/KEY: MOD_RES
<222> LOCATION: (5)..(5)
<223> OTHER INFORMATION: Xaa is Ile, Leu, Nle, Val, Nva, Aib, Acb, Ach,
      Acpe, or Acpr
<220> FEATURE:
<221> NAME/KEY: MOD_RES
<222> LOCATION: (6)..(6)
<223> OTHER INFORMATION: Xaa is Phe, Tyr, Trp, Cha, Bip, or Nal
<220> FEATURE:
<221> NAME/KEY: MOD_RES
<222> LOCATION: (7)..(7)
<223> OTHER INFORMATION: Xaa is Thr, Ser, hSer, or Val
<220> FEATURE:
<221> NAME/KEY: MOD_RES
<222> LOCATION: (8)..(8)
<223> OTHER INFORMATION: Xaa is  Asp, Asn, or Glu
<220> FEATURE:
<221> NAME/KEY: MOD_RES
<222> LOCATION: (9)..(9)
<223> OTHER INFORMATION: Xaa is Ser, hSer, Thr, Asn, Asp, Ala, Abu, Aib,
      Acb, Ach, Acpe, or Acpr
<220> FEATURE:
<221> NAME/KEY: MOD_RES
<222> LOCATION: (10)..(10)
<223> OTHER INFORMATION: Xaa is Tyr, Phe, Cha, Nal, or Trp
<220> FEATURE:
<221> NAME/KEY: MOD_RES
<222> LOCATION: (11)..(11)
<223> OTHER INFORMATION: Xaa is Ser, hSer, Thr, Ala, Abu, Aib, Acb, Ach,
      Acpe, or Acpr
<220> FEATURE:
<221> NAME/KEY: MOD_RES
<222> LOCATION: (12)..(12)
<223> OTHER INFORMATION: Xaa is Arg, Lys, Dab, Dap, or Orn
<220> FEATURE:
<221> NAME/KEY: MOD_RES
<222> LOCATION: (13)..(13)
<223> OTHER INFORMATION: Xaa is Tyr, Phe, Cha, Nal, or Trp
<220> FEATURE:
<221> NAME/KEY: MOD_RES
<222> LOCATION: (14)..(14)
<223> OTHER INFORMATION: Xaa is Arg, Lys, Dab, Dap, or Orn
<220> FEATURE:
<221> NAME/KEY: MOD_RES
<222> LOCATION: (15)..(15)
<223> OTHER INFORMATION: Xaa is Lys, Ala, Dab, Dap, Orn, Abu, Aib, Acb,
      Ach, Acpe, or Acpr
<220> FEATURE:
<221> NAME/KEY: MOD_RES
<222> LOCATION: (16)..(16)
<223> OTHER INFORMATION: Xaa is Gln, Glu, Asn, Asp; Aib, Acb, Ach, Acpe,
      or Acpr
<220> FEATURE:
<221> NAME/KEY: MOD_RES
<222> LOCATION: (17)..(17)
<223> OTHER INFORMATION: Xaa is Met, Nle, Leu, Ile, Ala, Abu, Aib, Acb,
      Ach, Acpe, or Acpr
<220> FEATURE:
<221> NAME/KEY: MOD_RES
<222> LOCATION: (18)..(18)
<223> OTHER INFORMATION: Xaa is Ala, Abu, Aib, Acb, Ach, Acpe, or Acpr
```

```
<220> FEATURE:
<221> NAME/KEY: MOD_RES
<222> LOCATION: (19)..(19)
<223> OTHER INFORMATION: Xaa is Val, Nva, Ser, Leu, Thr, Aib, Acb, Ach,
      Acpe, or Acpr
<220> FEATURE:
<221> NAME/KEY: MOD_RES
<222> LOCATION: (20)..(20)
<223> OTHER INFORMATION: Xaa is Lys, Ala, Dab, Dap, Orn, Abu, Aib, Acb,
      Ach, Acpe, or Acpr
<220> FEATURE:
<221> NAME/KEY: MOD_RES
<222> LOCATION: (21)..(21)
<223> OTHER INFORMATION: Xaa is Lys, Ala, Dab, Dap, Orn, Abu, Aib, Acb,
      Ach, Acpe, or Acpr
<220> FEATURE:
<221> NAME/KEY: MOD_RES
<222> LOCATION: (22)..(22)
<223> OTHER INFORMATION: Xaa is Tyr, Phe, Cha, Nal, Trp, Ala, Abu, Aib,
      Acb, Ach, Acpe, or Acpr
<220> FEATURE:
<221> NAME/KEY: MOD_RES
<222> LOCATION: (23)..(23)
<223> OTHER INFORMATION: Xaa is Leu, Nle, Ile, Val, Nva, Aib, Acb, Ach,
      Acpe, or Acpr
<220> FEATURE:
<221> NAME/KEY: MOD_RES
<222> LOCATION: (24)..(24)
<223> OTHER INFORMATION: Xaa is Ala, Asn, Abu, Aib, Acb, Ach, Acpe, or
      Acpr
<220> FEATURE:
<221> NAME/KEY: MOD_RES
<222> LOCATION: (25)..(25)
<223> OTHER INFORMATION: Xaa is Ala, Val, Leu, Met, Nle, Ile, Ser, hSer,
      Thr, Abu, Aib, Acb, Ach, Acpe, Acpr, or is omitted
<220> FEATURE:
<221> NAME/KEY: MOD_RES
<222> LOCATION: (26)..(26)
<223> OTHER INFORMATION: Xaa is Val, Nva, Leu, Met, Nle, Ile, Ala, Abu,
      Aib, Acb, Ach, Acpe, Acpr, or is omitted
<220> FEATURE:
<221> NAME/KEY: MOD_RES
<222> LOCATION: (27)..(27)
<223> OTHER INFORMATION: Xaa is Leu, D-Leu, Met, D-Met, Nle, Ile, D-Ile,
      Val, D-Val, Gaba, Ala, D-Ala, Abu, Aib, Acb, Ach, Acpe, Acpr, or
      is omitted
<220> FEATURE:
<221> NAME/KEY: MOD_RES
<222> LOCATION: (28)..(28)
<223> OTHER INFORMATION: Xaa is Gly, Ala, D-Ala, beta-Ala, Gaba, Asn,
      D-Asn, Gln, D-Gln, Asp, D-Asp, Abu, Aib, Acb, Ach, Acpe, Acpr, or
      is omitted
<220> FEATURE:
<221> NAME/KEY: MOD_RES
<222> LOCATION: (29)..(29)
<223> OTHER INFORMATION: Xaa is Lys, D-Lys, Arg, D-Arg, Dab, D-Dab, Dap,
      D-Dap, Orn, D-Orn, or is omitted
<220> FEATURE:
<221> NAME/KEY: MOD_RES
<222> LOCATION: (30)..(30)
<223> OTHER INFORMATION: Xaa is Arg, D-Arg, Lys, D-Lys, Dab, D-Dab, Dap,
      D-Dap, Orn, D-Orn, or is omitted
<220> FEATURE:
<221> NAME/KEY: MOD_RES
<222> LOCATION: (31)..(31)
<223> OTHER INFORMATION: Xaa is Tyr, D-Tyr, Phe, D-Phe, Trp, D-Trp, Cha,
      Nal, or is omitted
<220> FEATURE:
<221> NAME/KEY: MOD_RES
<222> LOCATION: (32)..(32)
<223> OTHER INFORMATION: Xaa is Lys, D-Lys, Arg, D-Arg, Dab, D-Dab, Dap,
      D-Dap, Orn, D-Orn, or is omitted
<220> FEATURE:
<221> NAME/KEY: MOD_RES
<222> LOCATION: (33)..(33)
<223> OTHER INFORMATION: Xaa is Gln, D-Gln, Glu, D-Glu, Asn, D-Asn, Asp;
      D-Asp, Abu, Aib, Acb, Ach, Acpe, Acpr, or is omitted
<220> FEATURE:
<221> NAME/KEY: MOD_RES
```

```
<222> LOCATION: (34)..(34)
<223> OTHER INFORMATION: Xaa is Arg, D-Arg, Lys, D-Lys, Dab, D-Dab, Dap,
      D-Dap, Orn, D-Orn, or is omitted
<220> FEATURE:
<221> NAME/KEY: MOD_RES
<222> LOCATION: (35)..(35)
<223> OTHER INFORMATION: Xaa is Val, D-Val, Nva, Ser, D-Ser, Thr; D-Thr,
      Abu, Aib, Acb, Ach, Acpe, Acpr, or is omitted
<220> FEATURE:
<221> NAME/KEY: MOD_RES
<222> LOCATION: (36)..(36)
<223> OTHER INFORMATION: Xaa is Lys, D-Lys, Arg, D-Arg, Dab, D-Dab, Dap,
      D-Dap, Orn, D-Orn, or is omitted
<220> FEATURE:
<221> NAME/KEY: MOD_RES
<222> LOCATION: (37)..(37)
<223> OTHER INFORMATION: Xaa is Asn, D-Asn, Gln, D-Gln, Asp, D-Asp, Ala,
      D-Ala, Aib, Acb, Ach, Acpe, Acpr, or is omitted
<220> FEATURE:
<221> NAME/KEY: MOD_RES
<222> LOCATION: (38)..(38)
<223> OTHER INFORMATION: Xaa is Lys, D-Lys, Arg, D-Arg, Dab, D-Dab, Dap,
      D-Dap, Orn, D-Orn, or is omitted
<220> FEATURE:
<221> NAME/KEY: MOD_RES
<222> LOCATION: (38)..(38)
<223> OTHER INFORMATION: The residue at position 38 can be modified to
      include OH, NH2, (C1-C18)alkoxyl, or NH(C1-C18)alkyl, or the
      modification is omitted

<400> SEQUENCE: 16

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa
        35
```

ANALOGS OF PITUITARY ADENYLATE CYCLASE-ACTIVATING POLYPEPTIDE (PACAP) AND METHODS FOR THEIR USE

CROSS-REFERENCE TO RELATED APPLICATIONS

This application is the U.S. National Stage filing under 35 U.S.C. §371 of International Application No. PCT/US2010/055164, filed Nov. 2, 2010, which claims benefit of U.S. Provisional Application No. 61/280,298, filed Nov. 2, 2009.

FIELD OF THE INVENTION

This invention relates to novel analogs of pituitary adenylate cyclase-activating polypeptide (PACAP), which are agonists for the PACAP/vasoactive intestinal peptide (VIP) receptors: $PAC_1$, $VPAC_1$ and $VPAC_2$ receptors. These PACAP analogs can be used as prophylactic/therapeutic agents for a wide range of medical disorders, including (but not limited to) age-related neurodegenerative diseases (such as Alzheimer's disease, Parkinson's disease and amyotrophic lateral sclerosis), injuries to the central nervous system caused by stroke, heart attack and blunt force trauma (such as concussions and spinal cord trauma), Huntington's disease and other CAG codon repeat expansion diseases, retinal diseases (such as diabetic retinopathy, macular degeneration and glaucoma), autoimmune diseases (such as rheumatoid arthritis, Crohn's disease, ulcerative colitis, scleroderma, Sjögren's disease, idiopathic membranous nephropathy, Goodpasture's disease, autoimmune hepatitis, myasthenia gravis, multiple sclerosis, Guillain-Barré syndrome, type I diabetes, Hashimoto's thyroiditis, Graves' disease, pemphigus vulgaris, and lupus erythematosus), keratoconjunctivitis sicca caused by autoimmune diseases or LASIK surgery, type II diabetes, sepsis caused by bacteria and/or viruses (including bacterial and viral toxins), acute and chronic cardiovascular diseases (such as myocardial infarction, atherosclerosis and restenosis), acute and chronic renal diseases (such as ischemia/reperfusion injury, nephritis and drug-induced nephrotoxicity), acute and chronic pulmonary diseases (such as asthma, chronic obstructive pulmonary disease, cystic fibrosis, and pulmonary arterial hypertension), systemic hypertension, hematological cancers (such as leukemias, lymphomas and plasma cell dyscrasias), eating disorders, acute and chronic liver diseases (such as ischemia/reperfusion injury, hepatitis and fatty liver), osteoporosis, pre-eclampsia, cell and solid organ transplantation, cognitive disorders, AIDS dementia complex, and aging of the central nervous system. These PACAP analogs coupled to suitable radionuclides can be used in the localization, diagnosis and treatment of disseminated cancers and metastatic tumors, and coupled to small molecule therapeutics can be used as vectors for targeted drug delivery. This invention also provides pharmaceutical compositions of one or more PACAP-like compounds of the invention either alone or in combination with one or more other prophylactic/therapeutic agents.

BACKGROUND OF THE INVENTION

Pituitary adenylate cyclase-activating polypeptide (PACAP) was isolated from ovine (sheep) hypothalami based on its ability to stimulate adenylate cyclase activity in rat anterior pituitary cell cultures (Miyata et al., *Biochem Biophys Res Commun* 164:567-574, 1989). PACAP exists as two α-amidated peptides with 38 (PACAP38; SEQ ID NO:1) or 27 (PACAP27; SEQ ID NO:2) amino acids. Both peptides have the same N-terminal 27 amino acids and are synthesized from the same prohormone. The sequence of PACAP38 is identical in all mammals and differs from the avian and amphibian orthologs by only one amino acid (Vaudry et al., *Pharmacol Rev* 52:269-324, 2000). PACAP is a member of the secretin/vasoactive intestinal peptide (VIP)/growth hormone-releasing hormone (GHRH) family, and PACAP27 has 68% sequence identity with VIP (SEQ ID NO:3). PACAP is most abundant in the brain and testis, but there are significant levels in other organs, including the pancreas, adrenals, thymus, spleen, lymph nodes, and duodenal mucosa (Vaudry et al., *Pharmacol Rev* 52:269-324, 2000). PACAP is synthesized as a preprohormone and is processed mainly by prohormone convertase 1, prohormone convertase 2 and prohormone convertase 4 (Li et al., *Neuroendocrinology* 69:217-226, 1999; Li et al., *Endocrinology* 141:3723-3730, 2000). The half-life of [$^{125}$I]-PACAP38 in the bloodstream of rats following intravenous injection is 5-6 minutes (Banks et al., *J Pharmacol Exp Ther* 267:690-696, 1993). Members of the secretin/VIP/GHRH family are degraded in plasma mainly by aminodipeptidases, especially dipeptidyl peptidase IV (Zhu et al., *J Biol Chem* 278:22418-2223, 2003).

A PACAP-specific receptor, designated as the $PAC_1$ receptor, has been cloned from several vertebrate species (Arimura, *Jpn J Physiol* 48:301-331, 1998; Vaudry et al., *Pharmacol Rev* 52:269-324, 2000). It is a G-protein-coupled receptor with seven putative membrane-spanning domains and belongs to a family of glycoprotein receptors that are coupled to multiple signal transduction pathways (Segre and Goldring, *Trends Endocrinol Metab* 4:309-314, 1993). PACAP binds not only to the $PAC_1$ receptor with a high affinity, but it also binds to the VIP1 ($VPAC_1$) and VIP2 ($VPAC_2$) receptors with an affinity comparable to or greater than VIP. On the other hand, VIP binds to the $PAC_1$ receptor with an affinity 1,000 times less than PACAP (Arimura, *Jpn J Physiol* 48:301-331, 1998). At least 10 splice variants of the rat $PAC_1$ receptor have been cloned and each variant is coupled to distinct combinations of signal transduction pathways (Vaudry et al., *Pharmacol Rev* 52:269-324, 2000). The "second" messengers include adenylate cyclase, phospholipase C, mitogen-activated protein (MAP) kinases, and calcium. PACAP/VIP receptor can be coupled to Gαs and/or Gαi in different types of cells. PACAP/VIP receptors are expressed in many different types of normal and cancer cells, including the catecholamine-containing cells in the adrenal medulla and the sympathetic ganglia; microglia, astrocytes and some types of neurons in the central nervous system; and T- and B-lymphocytes, macrophages, neutrophils, and dendritic cells in the immune system (Vaudry et al., *Pharmacol Rev* 52:269-324, 2000). PACAP is a potent stimulator of catecholamine secretion from the adrenal medulla (Watanabe et al., *Am J Physiol* 269:E903-E909, 1995), but a potent inhibitor of the secretion of tumor necrosis factor-α (TNF-α), interleukin (IL)-6 and IL-12 from activated macrophages (Ganea and Delgado, *Crit. Rev Oral Biol Med* 13:229-237, 2002). More pertinent to the present invention, PACAP stimulates the proliferation of C6 glioblastoma cells (Dufes et al., *J Mol Neurosci* 21:91-102, 2003), AR4-2J pancreatic carcinoma cells (Buscail et al., *Gastroenterology* 103:1002-1008, 1992) and MCF-7 breast cancer cells (Leyton et al., *Breast Cancer Res Treat* 56:177-186, 1999), but inhibits the proliferation of HEL myeloid leukemia cells (Hayez et al., *J Neuroimmunol* 149:167-181, 2004), SW403 colonic adenocarcinoma cells (Lelievre et al., *Cell Signal* 10:13-26, 1998) and multiple myeloma cells (Li et al., *Regul Pept* 145:24-32, 2008; see FIGS. 3 and 4).

Although PACAP was isolated during a screen for novel hypophysiotropic factors, it soon became apparent that it is a pleiotropic peptide (Arimura, *Jpn J Physiol* 48:301-331, 1998; Vaudry et al., *Pharmacol Rev* 52:269-324, 2000). The extraordinarily potent neuroprotective/neurotrophic properties of PACAP were investigated by several laboratories shortly after its isolation. The cytoprotective effects of PACAP and VIP have been studied much more extensively in the nervous system than in any other major organ of the body. The cell types that were protected by PACAP in various in vitro models include cerebellar granule cells, dorsal root ganglion cells, sympathetic ganglion cells, mesencephalic dopaminergic neurons, and basal forebrain cholinergic neurons (Arimura, *Jpn J Physiol* 48:301-331, 1998; Vaudry et al., *Pharmacol Rev* 52:269-324, 2000). PACAP also prevented the neuronal death induced by gp120, the envelope glycoprotein of the human immunodeficiency virus (HIV), in rat hippocampal neuron/glia co-cultures. The dose-response curve was bimodal, with peaks at $10^{-13}$ M and $10^{-10}$ M (Arimura et al., *Ann NY Acad Sci* 739:228-243, 1994). The critical findings in this study have been confirmed by Kong et al. (*Neuroscience* 91:493-500, 1999), who used lipopolysaccharide as the neurotoxin in primary murine cortical neuron/glia co-cultures. The neuroprotective effect at $10^{-12}$ M was correlated with a significant reduction in the accumulation of nitrite in the culture medium. The neuroprotective effect of "low" (femtomolar) doses of PACAP in neuron/glia co-cultures was abolished by PD98059, a MAP kinase inhibitor, but the neuroprotective effect of "high" (nanomolar) doses of PACAP was not affected by PD98059 (Li et al., *J Mol Neurosci* 27:91-106, 2005). However, the neuroprotective effect of nanomolar doses of PACAP was abolished by Rp-cAMP, a protein kinase A inhibitor.

The drawbacks of using peptides for neuroprotection in the brain include their poor transport across the blood-brain barrier and their short half-life in the circulation after systematic administration. However, PACAP38 has been shown to be transported from the blood to the brain via a saturable mechanism (Banks et al., *J Pharmacol Exp Ther* 267:690-696, 1993). Therefore, PACAP38 was tested as a neuroprotectant in common in vivo preclinical models of heart attack and stroke. Four-vessel occlusion in the rat was used to model the consequences of a heart attack for the brain (transient global forebrain ischemia). Blood flow to the forebrain was interrupted for 15 minutes. Following the 15-minute occlusion, there was a significant reduction in the number of pyramidal cells in the CA1 field of the hippocampus after 7 days in vehicle-infused rats. The reduction in the number of pyramidal cells at day 7 post-occlusion was significantly reversed in the rats continuously infused intravenously with PACAP38 (Uchida et al., *Brain Res* 736:280-286, 1996). Middle cerebral artery occlusion (MCAO) in the rat was used to model a stroke (transient focal cerebral ischemia). The middle cerebral artery was occluded for 2 hours using the intraluminal filament technique. The continuous intravenous infusion of PACAP38 beginning at 4, 8 or 12 hours after the start of the transient MCAO resulted in a reduction of the infarct volume of approximately 51%, 22% or 12%, respectively, 48 hours after the start of the MCAO (Reglodi et al., *Stroke* 31:1411-1417, 2000). These observations suggest that small changes in the concentration of PACAP in the brain can alter the vulnerability of nerve cells to injury.

The neuroprotective effects of low concentrations of PACAP in the nervous system are indirect and are probably mediated by at least four distinct mechanisms. (1) PACAP is a potent anti-inflammatory peptide. It has been shown to inhibit the induction of inducible nitric oxide synthase (iNOS) in activated macrophages, to inhibit the production of the pro-inflammatory cytokines TNF-α, IL-6 and IL-12 in activated macrophages, and to stimulate the production of the anti-inflammatory cytokine IL-10 in activated macrophages (Ganea and Delgado, *Crit Rev Oral Biol Med* 13:229-237, 2002). PACAP probably inhibits inflammation at multiple steps in the inflammatory cascade because it is an endogenous counter-regulator of the inflammatory process. PACAP is also an extraordinarily potent "deactivator" of activated microglial cells (Kong et al., *Neuroscience* 91:493-500, 1999; Delgado et al., *Glia* 39:148-161, 2002), which are the resident macrophage-like cells in the nervous system. (2) Femtomolar ($10^{-15}$ M) concentrations of PACAP increase the levels of the mRNA for activity-dependent neurotrophic factor in murine neuron/glia co-cultures (David et al., *Society for Neuroscience* [33rd Annual Meeting], New Orleans, La., #38.1 [Abstract], 2003). Furthermore, the number of $PAC_1$ receptors on "reactive" glial cells is increased following injury (Uchida et al., *Brain Res* 736:280-286, 1996). Brenneman et al. (*Neuropeptides* 36:271-280, 2002) had previously shown that femtomolar concentrations of PACAP stimulate the release of RANTES in astrocyte cultures and that immunoneutralization of RANTES reduces the neuroprotective effect of PACAP in neuron/glia co-cultures. (3) Yang et al. (*J Pharmacol Exp Ther* 319:595-603, 2006) have shown that femtomolar concentrations of PACAP inhibit microglial NADPH oxidase activity and extracellular superoxide levels in mesencephalic neuron/glia co-cultures. (4) Figiel and Engele (*J Neurosci* 20:3596-3605, 2000) have reported that PACAP increased the expression of the glutamate transporters GLT-1 and GLAST and increased the activity of the glutamate metabolizing enzyme glutamine synthetase in astrocytes. These effects of PACAP would be expected to decrease glutamatergic neurotransmission. The extensive studies about the cytoprotective properties of PACAP in the nervous system have provided a solid framework for studying the cytoprotective properties of PACAP in other organs.

Native PACAP has already been administered to normal human volunteers by investigators in at least four different laboratories (Chiodera et al., *Neuroendocrinology* 64:242-246, 1996; Filipsson et al., *J Clin Endocrinol Metab* 82:3093-3098, 1997; Doberer et al., *Eur J Clin Invest* 37:665-672, 2007; Murck et al., *Am J Physiol* 292:E853-E857, 2007) and to a patient with multiple myeloma under a U.S. Food and Drug Administration (FDA)-approved protocol (Li et al., *Peptides* 28:1891-1895, 2007). The only untoward effect reported was a transient flushing.

PACAP is an extraordinarily potent peptide in vitro. However, the usefulness of PACAP as a drug is limited by its very short half-life in the circulation following systemic administration due to both rapid proteolysis and rapid filtration by the kidney. Therefore, there is a need for PACAP analogs that are resistant to proteolysis and/or have reduced rates of filtration by the kidney.

Citation or discussion of a reference herein shall not be construed as an admission that such reference is prior art to the present invention.

SUMMARY OF THE INVENTION

The inventors have made novel peptide analogs of native human PACAP38 and native human PACAP27 that are agonists at one or more PACAP/VIP receptors, and that have significant biological activity in preclinical in vitro and in vivo models for several major medical disorders. The novel PACAP analogs of this invention can be synthesized by the methods of peptide chemistry.

In a first aspect, the invention features novel PACAP analogs that can be used for the prophylactic/therapeutic and diagnostic purposes described in more detail below can be defined by a general formula (I),

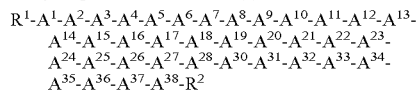
$R^1-A^1-A^2-A^3-A^4-A^5-A^6-A^7-A^8-A^9-A^{10}-A^{11}-A^{12}-A^{13}-$
$A^{14}-A^{15}-A^{16}-A^{17}-A^{18}-A^{19}-A^{20}-A^{21}-A^{22}-A^{23}-$
$A^{24}-A^{25}-A^{26}-A^{27}-A^{28}-A^{30}-A^{31}-A^{32}-A^{33}-A^{34}-$
$A^{35}-A^{36}-A^{37}-A^{38}-R^2$ or a pharmaceutically acceptable salt thereof, wherein
$A^1$ is His, D-His, Tyr, D-Tyr, Trp, D-Trp, Pal, or D-Pal;
$A^2$ is Ser, D-Ser, hSer, N-Me-Ser, Thr, D-Thr, Ala, D-Ala, Ile, D-Ile, Pro, D-Pro, Abu, Aib, Acb, Ach, Acpe, or Acpr;
$A^3$ is Pip;
$A^4$ is Gly, Ala, D-Ala, β-Ala, Gaba, Abu, Aib, Acb, Ach, Acpe, or Acpr;
$A^5$ is Ile, Leu, Nle, Val, Nva, Aib, Acb, Ach, Acpe, or Acpr;
$A^6$ is Phe, Tyr, Trp, Cha, Bip, or Nal;
$A^7$ is Thr, Ser, hSer, or Val;
$A^8$ is Asp, Asn, or Glu;
$A^9$ is Ser, hSer, Thr, Asn, Asp, Ala, Abu, Aib, Acb, Ach, Acpe, or Acpr;
$A^{10}$ is Tyr, Phe, Cha, Nal, or Trp;
$A^{11}$ is Ser, hSer, Thr, Ala, Abu, Aib, Acb, Ach, Acpe, or Acpr;
$A^{12}$ is Arg, Lys, Dab, Dap, or Orn;
$A^{13}$ is Tyr, Phe, Cha, Nal, or Trp;
$A^{14}$ is Arg, Lys, Dab, Dap, or Orn;
$A^{15}$ is Lys, Ala, Dab, Dap, Orn, Abu, Aib, Acb, Ach, Acpe, or Acpr;
$A^{16}$ is Gln, Glu, Asn, Asp; Aib, Acb, Ach, Acpe, or Acpr;
$A^{17}$ is Met, Nle, Leu, Ile, Ala, Abu, Aib, Acb, Ach, Acpe, or Acpr;
$A^{18}$ is Ala, Abu, Aib, Acb, Ach, Acpe, or Acpr;
$A^{19}$ is Val, Nva, Ser, Leu, Thr, Aib, Acb, Ach, Acpe, or Acpr;
$A^{20}$ is Lys, Ala, Dab, Dap, Orn, Abu, Aib, Acb, Ach, Acpe, or Acpr;
$A^{21}$ is Lys, Ala, Dab, Dap, Orn, Abu, Aib, Acb, Ach, Acpe, or Acpr;
$A^{22}$ is Tyr, Phe, Cha, Nal, Trp, Ala, Abu, Aib, Acb, Ach, Acpe, or Acpr;
$A^{23}$ is Leu, Nle, Ile, Val, Nva, Aib, Acb, Ach, Acpe, or Acpr;
$A^{24}$ is Ala, Asn, Abu, Aib, Acb, Ach, Acpe, or Acpr;
$A^{25}$ is Ala, Val, Leu, Met, Nle, Ile, Ser, hSer, Thr, Abu, Aib, Acb, Ach, Acpe, Acpr, or is deleted;
$A^{26}$ is Val, Nva, Leu, Met, Nle, Ile, Ala, Abu, Aib, Acb, Ach, Acpe, Acpr, or is deleted;
$A^{27}$ is Leu, D-Leu, Met, D-Met, Nle, Ile, D-Ile, Val, D-Val, Gaba, Ala, D-Ala, Abu, Aib, Acb, Ach, Acpe, Acpr, or is deleted;
$A^{28}$ is Gly, Ala, D-Ala, 13-Ala, Gaba, Asn, D-Asn, Gln, D-Gln, Asp, D-Asp, Abu, Aib, Acb, Ach, Acpe, Acpr, or is deleted;
$A^{29}$ is Lys, D-Lys, Arg, D-Arg, Dab, D-Dab, Dap, D-Dap, Orn, D-Orn, or is deleted;
$A^{30}$ is Arg, D-Arg, Lys, D-Lys, Dab, D-Dab, Dap, D-Dap, Orn, D-Orn, or is deleted;
$A^{31}$ is Tyr, D-Tyr, Phe, D-Phe, Trp, D-Trp, Cha, Nal, or is deleted;
$A^{32}$ is Lys, D-Lys, Arg, D-Arg, Dab, D-Dab, Dap, D-Dap, Orn, D-Orn, or is deleted;
$A^{33}$ is Gln, D-Gln, Glu, D-Glu, Asn, D-Asn, Asp; D-Asp, Abu, Aib, Acb, Ach, Acpe, Acpr, or is deleted;
$A^{34}$ is Arg, D-Arg, Lys, D-Lys, Dab, D-Dab, Dap, D-Dap, Orn, D-Orn, or is deleted;
$A^{35}$ is Val, D-Val, Nva, Ser, D-Ser, Thr; D-Thr, Abu, Aib, Acb, Ach, Acpe, Acpr, or is deleted;
$A^{36}$ is Lys, D-Lys, Arg, D-Arg, Dab, D-Dab, Dap, D-Dap, Orn, D-Orn, or is deleted;
$A^{37}$ is Asn, D-Asn, Gln, D-Gln, Asp, D-Asp, Ala, D-Ala, Aib, Acb, Ach, Acpe, Acpr, or is deleted;
$A^{38}$ is Lys, D-Lys, Arg, D-Arg, Dab, D-Dab, Dap, D-Dap, Orn, D-Orn, or is deleted;
$R^1$ is independently selected from a group of H, $(C_1-C_{18})$alkyl and $CO(C_1-C_{18})$alkyl
$R^2$ is independently selected from a group of OH, $NH_2$, $(C_1-C_{18})$alkoxyl, and $NH(C_1-C_{18})$alkyl.

In other embodiments, the PACAP-like compound is a polypeptide having a sequence with at least 80%, 85%, 90%, 95%, 97%, 99%, or 100% sequence identity to a sequence selected from SEQ ID NOs: 4-13, or an analog or peptidomimetic thereof, and pharmaceutically acceptable salts thereof. In yet other embodiments, the compound is present in a composition having a pharmaceutically acceptable carrier. In still other embodiments, the polypeptide is conjugated one or more radionuclides (e.g., $^{11}C$, $^{13}N$, $^{15}O$, $^{18}F$, $^{52}Fe$, $^{55}Co$, $^{61}Cu$, $^{62}Cu$, $^{64}Cu$, $^{67}Cu$, $^{67}Ga$, $^{68}Ga$, $^{62}Zn$, $^{63}Zn$, $^{70}As$, $^{71}As$, $^{74}As$, $^{76}Br$, $^{79}Br$, $^{82}Rb$, $^{86}Y$, $^{89}Zr$, $^{110}In$, $^{111}In$, $^{120}I$, $^{123}I$, $^{124}I$, $^{125}I$, $^{131}I$, $^{122}Xe$, $^{175}Lu$, $^{154}Gd$, $^{155}Gd$, $^{156}Gd$, $^{157}Gd$, $^{158}Gd$, $^{94m}Tc$, $^{94}Tc$, and $^{99m}Tc$) or small molecules (e.g., a therapeutic or anticancer agent, such as cisplatin, carboplatin, oxaliplatin, bleomycin, mitomycin C, calicheamicins, maytansinoids, geldanamycin, doxorubicin, idarubicin, daunorubicin, epirubicin, busulfan, carmustine (BCNU), lomustine (CCNU), semustine, thalidomide, lenalidomide, methotrexate, azathioprine, 6-mercaptopurine, fludarabine, 5-azacytidine, pentostatin (2'-deoxycoformycin), cytarabine (cytosine arabinoside), gemcitabine, 5-fluorouracil, hydroxyurea, elesclomol, etoposide, teniposide, amsacrine, camptothecin, topotecan, irinotecan, chlorambucil, cyclophosphamide, ifosfamide, melphalan, bortezomib, vincristine, vinblastine, vinorelbine, paclitaxel, docetaxel, cyclosporine A, tacrolimus (FK506), sirolimus (rapamycin), everolimus, temsirolimus, zotarolimus, or biolimus).

In a second aspect, the invention features a method for treating, managing, or preventing a disease selected from age-related neurodegenerative disease, a central nervous system disorder, Huntington's disease or other CAG codon repeat expansion disease, a retinal disease, an autoimmune disease, keratoconjunctivitis sicca caused by autoimmune diseases or LASIK surgery, type II diabetes, sepsis caused by a bacteria and/or a virus, an acute or chronic cardiovascular disease, an acute or chronic renal diseases, an acute or chronic pulmonary disease, systemic hypertension, a hematological cancer, an eating disorder, an acute or chronic liver disease, osteoporosis, pre-eclampsia, cell and solid organ transplantation, a cognitive disorder, acquired immunodeficiency syndrome (AIDS) dementia complex, aging of the central nervous system, and a disease caused in part by premature in-frame stop codons that result in the synthesis of truncated nonfunctional proteins, said method comprising administering to a subject (e.g., a mammal, such as a human) in need thereof an effective amount of one or more PACAP-like compounds or a pharmaceutically acceptable salt thereof. In several embodiments of the method, the age-related neurodegenerative disease is selected from Alzheimer's disease, Parkinson's disease and amyotrophic lateral sclerosis; the central nervous system disorder is caused by stroke, heart attack or blunt force trauma, in which, preferably, the blunt force trauma is a concussion or spinal cord trauma; the retinal disease is diabetic retinopathy, macular degeneration or glaucoma; the autoimmune disease is rheumatoid arthritis, Crohn's disease, ulcerative colitis, scleroderma, Sjögren's disease, idiopathic membranous nephropathy, Goodpasture's disease, autoimmune hepatitis, myasthenia gravis, multiple sclerosis, Guillain-Barré syndrome, type I diabetes, Hashimoto's thyroiditis, Graves' disease, pemphigus vulgaris, or lupus erythematosus; the septsis is caused by a bacterial or viral toxin; the acute or chronic cardiovascular disease is myocardial infarction, atherosclerosis, or restenosis; the acute or chronic renal disease is ischemia/reperfusion injury, nephritis, or drug-induced nephrotoxicity; the acute or chronic pulmonary disease is asthma, chronic obstructive pulmonary disease, cystic fibrosis, or pulmonary arterial hypertension; the hematological cancer is a lymphoid or myeloid hematopoietic cancer, wherein preferably said lymphoid or myeloid hematopoietic cancer is a leukemia, a lymphoma, a plasma cell dyscrasia, multiple myeloma, or an adenocarcinoma; the acute or chronic liver disease is ischemia/reperfusion injury, hepatitis, and fatty liver; or the disease caused in part by premature in-frame stop codons that result in the synthesis of truncated nonfunctional proteins is selected from cystic fibrosis, Duchenne muscular dystrophy, Hurler's syndrome, nephropathic cystinosis, polycystic kidney disease, retinitis pigmentosa, and ataxia telangiectasia.

In other embodiments of the second aspect of the invention, the subject has an injury to one or more major organs of the body due to treatment with a prophylactic or therapeutic agent other than the PACAP-like compound, trauma, or acute or chronic disease. In other embodiments, the subject is being treated with a primary therapeutic selected from one or more of cisplatin, carboplatin, oxaliplatin, bleomycin, mitomycin C, calicheamicins, maytansinoids, geldanamycin, doxorubicin, idarubicin, daunorubicin, epirubicin, busulfan, carmustine (BCNU), lomustine (CCNU), semustine, thalidomide, lenalidomide, methotrexate, azathioprine, 6-mercaptopurine, fludarabine, 5-azacytidine, pentostatin (2'-deoxycoformycin), cytarabine (cytosine arabinoside), gemcitabine, 5-fluorouracil, hydroxyurea, elesclomol, etoposide, teniposide, amsacrine, camptothecin, topotecan, irinotecan, chlorambucil, cyclophosphamide, ifosfamide, melphalan, bortezomib, vincristine, vinblastine, vinorelbine, paclitaxel, docetaxel, G418, gentamicin, streptomycin, kanamycin, tobramycin, amikacin, arbekacin, netilmicin, paromomycin, rhodostreptomycin, neomycin, framycetin, ribostamycin, bekanamycin, dibekacin, spectinomycin, hygromycin B, sisomicin, isepamicin, verdamicin, astromicin, apramycin, amphotericin B, rifampicin, pentamidine, cyclosporine A, tacrolimus (FK506), sirolimus (rapamycin), everolimus, temsirolimus, zotarolimus, or biolimus (e.g., the subject is being treated with a primary therapy that includes treatment with carmustine, vincristine, paclitaxel, or thalidomide). In another embodiment, the subject has a lymphoid or myeloid cancer.

In still other embodiments of the second aspect of the invention, the PACAP-like compounds, or pharmaceutically acceptable salts thereof, bind to one or more of the PACAP/VIP receptors and/or reduce one or more injuries to one or more major organs of the body of the subject due to treatment with a prophylactic or therapeutic agent other than the PACAP-like compound, trauma, or acute or chronic disease. In other embodiments, the PACAP-like compound is a compound of the first aspect of the invention, or a pharmaceutically acceptable salt thereof. In an embodiment, the subject is resistant to treatment with a glucocorticoid (e.g., dexamethasone, prednisolone, methylprednisolone, or prednisone). In another embodiment, administration of the PACAP-like compound in the subject replaces administration of a corticosteroid selected from prednisone or dexamethasone when the subject is treated using the COP (cyclophosphamide, vincristine and prednisone) or VAD (vincristine, doxorubicin and dexamethasone) regimen.

In other embodiments of the second aspect of the invention, the PACAP-like compound is linked to a polyethylene glycol polymer with a molecular weight from about 4 kilodaltons to about 40 kilodaltons. In still other embodiments, the PACAP-like compound is the unamidated (free acid) form of one or more of the compounds of the first aspect of the invention, and the compound may be flanked by amino-acid consensus sequences for one or more proteolytic enzymes. The method may also involve administration of a PACAP-like compound of the first aspect of the invention that is a peptidomimetic analog.

In still other embodiments of the first aspect of the invention, the PACAP-like compound is administered at a dosage that produces a concentration of $10^{-14}$ M to $10^{-6}$ M in the blood of the subject. In another embodiment, the PACAP-like compound is administered by intravenous infusion at a rate of about 1 μmol/kg body weight/hour to about 20 μmol/kg body weight/hour. In other embodiments, the compound is administered for about 1-12 hours. In still other embodiments, the PACAP-like compound is injected intraperitoneally, subcutaneously, intramuscularly, intranasally, or as an aerosol one or more times (e.g., 2, 3, 4, 5, 6, 7, 8, 9, or 10 times) per day, week, month, or year. In other embodiments, the PACAP-like compound is administered orally in a time-dependent or pH-dependent formulation one or more times per day, week, month, or year; the PACAP-like compound is administered as a controlled release or a sustained release formulation; the PACAP-like compound is administered after encapsulation in liposomes or microparticles; the PACAP-like compound is administered transcutaneously after encapsulation in dendrimers; the PACAP-like compound is used to coat a metallic or a biodegradable stent; or the PACAP-like compound is administered in combination with one or more other cytoprotective adjuvants, such as amifostine, dexrazoxane, mesna, palifermin, or N-acetylcysteine.

In other embodiments of the second aspect of the invention, the injuries to one or more major organs of the body (e.g., the nervous system, heart, lung, kidneys, liver, ear, or gastrointestinal tract) are caused by a prophylactic or therapeutic agent other than a PACAP-like compound (e.g., an anticancer agent, a steroid, or an aminoglycoside). The prophylactic or therapeutic agent may be one or more of cisplatin, carboplatin, oxaliplatin, bleomycin, mitomycin C, calicheamicins, maytansinoids, geldanamycin, doxorubicin, idarubicin, daunorubicin, epirubicin, busulfan, carmustine (BCNU), lomustine (CCNU), semustine, thalidomide, lenalidomide, methotrexate, azathioprine, 6-mercaptopurine, fludarabine, 5-azacytidine, pentostatin (2'-deoxycoformycin), cytarabine (cytosine arabinoside), gemcitabine, 5-fluorouracil, hydroxyurea, elesclomol, etoposide, teniposide, amsacrine, camptothecin, topotecan, irinotecan, chlorambucil, cyclophosphamide, ifosfamide, melphalan, bortezomib, vincristine, vinblastine, vinorelbine, paclitaxel, docetaxel, G418 (GENETICIN™), gentamicin, streptomycin, kanamycin, tobramycin, amikacin, arbekacin, neomycin, netilmicin, paromomycin, rhodostreptomycin, framycetin, ribostamycin, bekanamycin, dibekacin, spectinomycin, hygromycin B, sisomicin, isepamicin, verdamicin, astromicin, apramycin, amphotericin B, rifampicin, pentamidine, cyclosporine A, tacrolimus (FK506), sirolimus (rapamycin), everolimus, temsirolimus, zotarolimus, or biolimus. In yet other embodiments, the injuries to one or more major organs of the body are due to treatment with an unconjugated therapeutic or anticancer agent, a therapeutic or anticancer agent conjugated to a monoclonal antibody or a bioactive peptide, or an unconjugated bioactive peptide. In other embodiments, the PACAP-like compound is conjugated to a therapeutic or anticancer agent or the PACAP- like compound has an additive anticancer effect when administered with one or more other anticancer agents (e.g., those described herein). In an embodiment, the subject is being treated with one or more therapeutic or anticancer agents for a hematopoietic cancer, a myeloproliferative disorder, or multiple myeloma. In other embodiments, the subject is being treated with an aminoglycoside and the PACAP-like compound is administered to inhibit or reduce side-effects resulting from administration of said aminoglycoside (e.g., amikacin, arbekacin, G418, gentamicin, kanamycin, netilmicin, paromomycin, rhodostreptomycin, streptomycin, neomycin, framycetin, ribostamycin, bekanamycin, dibekacin, spectinomycin, hygromycin B, sisomicin, isepamicin, verdamicin, tobramycin,astromicin, and apramycin). In other embodiments, the PACAP-like compound inhibits or reduces nephotoxicity or ototoxicity caused by the aminoglycoside (e.g., amikacin, arbekacin, G418, gentamicin, kanamycin, neomycin, netilmicin, paromomycin, rhodostreptomycin, streptomycin, neomycin, framycetin, ribostamycin, bekanamycin, dibekacin, spectinomycin, hygromycin B, paraomomycin sulfate, sisomicin, isepamicin, verdmicin, tobramycin,astromicin, and apramycin), in particular gentamicin.

A third aspect of the invention features a method for the localization, diagnosis, or treatment of a disseminated cancer or a metastatic tumor (e.g., a hematological cancer, such as leukemia, lymphoma, or myeloma) in a subject (e.g., a mammal, such as a human) by administering an effective amount of a conjugate that includes one or more PACAP-like compounds or a pharmaceutically acceptable salt thereof coupled to one or more radionuclides (e.g., $^{11}$C, $^{13}$N, $^{15}$O, $^{18}$F, $^{52}$Fe, $^{55}$Co, $^{61}$Cu, $^{62}$Cu, $^{64}$Cu, $^{67}$Cu, $^{67}$Ga, $^{68}$Ga, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{111}$In, $^{120}$I, $^{123}$I, $^{124}$I, $^{125}$I, $^{131}$I, $^{122}$Xe, $^{175}$Lu, $^{154}$Gd, $^{155}$Gd, $^{156}$Gd, $^{157}$Gd, $^{158}$Gd, $^{94m}$Tc, $^{94}$Tc, and $^{99m}$Tc). In an embodiment, the PACAP-like compounds bind to one or more of PACAP/VIP receptor on the surface of one or more cells of the disseminated cancer or metastatic tumor; the PACAP-like compound includes one or more of those compounds of the first aspect of the invention or a pharmaceutically acceptable salt thereof (e.g., a polypeptide with a sequence having a sequence identity of 85%-100% to a sequence selected from SEQ ID NOs: 4-13). In other embodiments, the conjugate targets a cell that is a component of a granuloma caused by one or more infectious agents or an autoimmune disease; the subject is being treated with one or more of the conjugates for lymphoid, myeloid hematopoietic cancer, or multiple myeloma.

A fourth aspect of the invention features a method of producing a conjugate by coupling one or more radionuclides (11C, 13N, 150, 18F, 52Fe, 55Co, 61Cu, 62Cu, 64Cu, 67Cu, 67Ga, 68Ga, 62Zn, 63Zn, 70As, 71As, 74As, 76Br, 79Br, 82Rb, 86Y, 89Zr, 110In, 111In, 120I, 123I, 124I, 125I, 131I, 122Xe, 175Lu, 154Gd, 155Gd, 156Gd, 157Gd, 158Gd, 94mTc, 94Tc, and 99mTc) or small molecules (e.g., a therapeutic or anticancer agent, such as cisplatin, carboplatin, oxaliplatin, bleomycin, mitomycin C, calicheamicins, maytansinoids, geldanamycin, doxorubicin, idarubicin, daunorubicin, epirubicin, busulfan, carmustine (BCNU), lomustine (CCNU), semustine, thalidomide, lenalidomide, methotrexate, azathioprine, 6-mercaptopurine, fludarabine, 5-azacytidine, pentostatin (2'-deoxycoformycin), cytarabine (cytosine arabinoside), gemcitabine, 5-fluorouracil, hydroxyurea, elesclomol, etoposide, teniposide, amsacrine, camptothecin, topotecan, irinotecan, chlorambucil, cyclophosphamide, ifosfamide, melphalan, bortezomib, vincristine, vinblastine, vinorelbine, paclitaxel, docetaxel, cyclosporine A, G418, gentamicin, streptomycin, kanamycin, tobramycin, amikacin, arbekacin, netilmicin, paromomycin, rhodostreptomycin, neomycin, framycetin, ribostamycin, bekanamycin, dibekacin, spectinomycin, hygromycin B, paraomomycin sulfate, sisomicin, isepamicin, verdamicin, astromicin, apramycin, amphotericin B, rifampicin, pentamidine, tacrolimus (FK506), sirolimus (rapamycin), everolimus, temsirolimus, zotarolimus, or biolimus) to one or more PACAP-like compounds. In other embodiments, the PACAP -like compound includes one or more of those compounds of the first aspect of the invention or a pharmaceutically acceptable salt thereof (e.g., a polypeptide with a sequence having a sequence identity of 85%-100% to a sequence selected from SEQ ID NOs: 4-13).

A fifth aspect of the invention features a method for targeting delivery of a therapeutic or anticancer agent to a specific cell or tissue of a subject (e.g., a mammal, such as a human) by administering to the subject an effective amount of a conjugate that includes one or more PACAP-like compounds (e.g., one or more of those compounds of the first aspect of the invention (e.g., a polypeptide with a sequence having a sequence identity of 85%-100% to a sequence selected from SEQ ID NOs: 4-13)), or a pharmaceutically acceptable salt thereof, coupled to one or more small molecules (e.g., a therapeutic agent or anticancer agent, such as cisplatin, carboplatin, oxaliplatin, bleomycin, mitomycin C, calicheamicins, maytansinoids, geldanamycin, doxorubicin, idarubicin, daunorubicin, epirubicin, busulfan, carmustine (BCNU), lomustine (CCNU), semustine, thalidomide, lenalidomide, methotrexate, azathioprine, 6-mercaptopurine, fludarabine, 5-azacytidine, pentostatin (2'-deoxycoformycin), cytarabine (cytosine arabinoside), gemcitabine, 5-fluorouracil, hydroxyurea, elesclomol, etoposide, teniposide, amsacrine, camptothecin, topotecan, irinotecan, chlorambucil, cyclophosphamide, ifosfamide, melphalan, bortezomib, vincristine, vinblastine, vinorelbine, paclitaxel, docetaxel, cyclosporine A, G418, gentamicin, streptomycin, kanamycin, tobramycin, amikacin, arbekacin, netilmicin, paromomycin, rhodostreptomycin, neomycin, framycetin, ribostamycin, bekanamycin, dibekacin, spectinomycin, hygromycin B, paraomomycin sulfate, sisomicin, isepamicin, verdamicin, astromicin, apramycin, amphotericin B, rifampicin, pentamidine, tacrolimus (FK506), sirolimus (rapamycin), everolimus, temsirolimus, zotarolimus, or biolimus, or an anti-inflammatory agent). In other embodiments, the one or more PACAP-like compounds bind to one or more PACAPNIP receptors on the surface of the cell or tissue and the conjugate enters the interior of the cell or tissue by receptor-mediated endocytosis.

In other embodiments of the fifth aspect of the invention, the subject has a disease (e.g., age-related neurodegenerative disease, a central nervous system disorder, Huntington's disease or other CAG codon repeat expansion disease, a retinal disease, an autoimmune disease, keratoconjunctivitis sicca caused by autoimmune diseases or LASIK surgery, type II diabetes, sepsis caused by a bacteria and/or a virus, an acute or chronic cardiovascular disease, an acute or chronic renal diseases, an acute or chronic pulmonary disease, systemic hypertension, a hematological cancer, an eating disorder, an acute or chronic liver disease, osteoporosis, pre-eclampsia, cell and solid organ transplantation, a cognitive disorder, acquired immunodeficiency syndrome (AIDS) dementia complex, aging of the central nervous system, or a disease caused in part by premature in-frame stop codons that result in the synthesis of truncated nonfunctional proteins). In several embodiments of the method of the fifth aspect of the invention, the age-related neurodegenerative disease is selected from Alzheimer's disease, Parkinson's disease and amyotrophic lateral sclerosis; the central nervous system disorder is caused by stroke, heart attack or blunt force trauma, in which, preferably, the blunt force trauma is a concussion or spinal cord trauma; the retinal disease is diabetic retinopathy, macular degeneration or glaucoma; the autoimmune disease is rheumatoid arthritis, Crohn's disease, ulcerative colitis, scleroderma, Sjögren's disease, idiopathic membranous nephropathy, Goodpasture's disease, autoimmune hepatitis, myasthenia gravis, multiple sclerosis, Guillain-Barré syndrome, type I diabetes, Hashimoto's thyroiditis, Graves' disease, pemphigus vulgaris, or lupus erythematosus; the septsis is caused by a bacterial or viral toxin; the acute or chronic cardiovascular disease is myocardial infarction, atherosclerosis, or restenosis; the acute or chronic renal disease is ischemia/reperfusion injury, nephritis, or drug-induced nephrotoxicity; the acute or chronic pulmonary disease is asthma, chronic obstructive pulmonary disease, cystic fibrosis, or pulmonary arterial hypertension; the hematological cancer is a lymphoid or myeloid hematopoietic cancer, wherein preferably said lymphoid or myeloid hematopoietic cancer is a leukemia, a lymphoma, a plasma cell dyscrasia, multiple myeloma, or an adenocarcinoma; the acute or chronic liver disease is ischemia/reperfusion injury, hepatitis, and fatty liver; or the disease caused in part by premature in-frame stop codons that result in the synthesis of truncated nonfunctional proteins is selected from cystic fibrosis, Duchenne muscular dystrophy, Hurler's syndrome, nephropathic cystinosis, polycystic kidney disease, retinitis pigmentosa, and ataxia telangiectasia.

In other embodiments, the subject has an injury to one or more major organs of the body due to treatment with a prophylactic or therapeutic agent other than the PACAP-like compound, trauma, or acute or chronic disease. In still other embodiments, the PACAP-like compounds, or pharmaceutically acceptable salts thereof, bind to one or more of the PACAP/VIP receptors and/or reduce one or more injuries to one or more major organs of the body of the subject due to treatment with a prophylactic or therapeutic agent other than the PACAP-like compound, trauma, or acute or chronic disease.

In still other embodiments, the small molecule is anti-inflammatory agent and the subject is being treated for rheumatoid arthritis; the small molecule is an anticancer agent and the subject is being treated for multiple myeloma; the prophylactic or therapeutic agent is an anticancer agent, a steroid, an anti-inflammatory, or an aminoglycoside.

A sixth aspect of the invention features a method for detecting a granuloma in subject by administering to the subject (e.g., a mammal, such as a human) an effective amount of the polypeptide of the first aspect of the invention, or a pharmaceutically acceptable salt thereof, conjugated to a radionuclide (e.g., $^{11}$C, $^{13}$N, $^{15}$O, $^{18}$F, $^{52}$Fe, $^{55}$Co, $^{61}$Cu, $^{62}$Cu, $^{64}$Cu, $^{67}$Cu, $^{67}$Ga, $^{68}$Ga, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{111}$In, $^{120}$I, $^{123}$I, $^{124}$I, $^{125}$I, $^{131}$I, $^{122}$Xe, $^{175}$Lu, $^{154}$Gd, $^{155}$Gd, $^{156}$Gd, $^{157}$Gd, $^{158}$Gd, $^{94m}$Tc, $^{94}$Tc, or $^{99m}$Tc). In other embodiments, the subject has an infectious or autoimmune disease (e.g., tuberculosis or Crohn's disease); the polypeptide is a PACAP-like compound that is capable of binding to one or more of the PACAP/VIP receptors on the surface of target cells; the subject is being treated for tuberculosis; the subject is being treated with one or more of the conjugates of the invention that include an imaging agent for tuberculosis; the subject is being treated with $^{99m}$Tc-isonicotinylhydrazine (INH); the subject is being treated for Crohn's disease; the subject is being treated with one or more of the conjugates of the invention that include an imaging agent for Crohn's disease.

These novel PACAP analogs can be used as prophylactic/therapeutic agents for a wide range of medical disorders in humans or other mammals, including (but not limited to) age-related neurodegenerative diseases (such as Alzheimer's disease, Parkinson's disease and amyotrophic lateral sclerosis), injuries to the central nervous system caused by stroke, heart attack and blunt force trauma (such as concussions and spinal cord trauma), Huntington's disease and other CAG codon repeat expansion diseases, retinal diseases (such as diabetic retinopathy, macular degeneration and glaucoma), autoimmune diseases (such as rheumatoid arthritis, Crohn's disease, ulcerative colitis, scleroderma, Sjögren's disease, idiopathic membranous nephropathy, Goodpasture's disease, autoimmune hepatitis, myasthenia gravis, multiple sclerosis, Guillain-Barré syndrome, type I diabetes, Hashimoto's thyroiditis, Graves' disease, pemphigus vulgaris, and lupus erythematosus), keratoconjunctivitis sicca caused by autoimmune diseases or LASIK surgery, type II diabetes, sepsis caused by bacteria and/or viruses (including bacterial and viral toxins), acute and chronic cardiovascular diseases (such as myocardial infarction, atherosclerosis and restenosis), acute and chronic renal diseases (such as ischemia/reperfusion injury, nephritis and drug-induced nephrotoxicity), acute and chronic pulmonary diseases (such as asthma, chronic obstructive pulmonary disease, cystic fibrosis, and pulmonary arterial hypertension), systemic hypertension, hematological cancers (such as leukemias, lymphomas and plasma cell dyscrasias), eating disorders, acute and chronic liver diseases (such as ischemia/reperfusion injury, hepatitis and fatty liver), osteoporosis, pre-eclampsia, cell and solid organ transplantation, cognitive disorders, AIDS dementia complex, and aging of the central nervous system. The rationale and documentation for these diverse medical indications are described and documented below.

As life expectancy has increased, age-related neurodegenerative disorders, such as Alzheimer's disease, Parkinson's disease and amyotrophic lateral sclerosis, have become more prevalent and placed a greater burden on society. The published literature indicates that PACAP-like peptides can protect neurons (neuroepithelial cells) in vitro against a very broad range of injuries (Arimura, *Jpn J Physiol* 48:301-331, 1998; Vaudry et al., *Pharmacol Rev* 52:269-324, 2000). Published experiments using common in vivo preclinical models indicate that PACAP-like peptides should be efficacious for the treatment of Alzheimer's disease (Mercer et al., *J Neurosci Res* 76:205-215, 2004; Wu et al., *Neurobiol Aging* 27:377-386, 2006; Dogrukol-Ak et al., *J Cereb Blood Flow Metab* 29:411-422, 2009), Parkinson's disease (Delgado and Ganea., *FASEB J* 17:944-946, 2003; Reglodi et al., *Behav Brain Res* 151:303-312, 2004; Chung et al., *Hum Mol Genet.* 14:1709-1725, 2005; Deguil et al., *Neurotox Res.* 17:142-155, 2010) and amyotrophic lateral sclerosis (Arimura et al., 1994; Nguyen et al., *J Neurosci* 24:1340-1349, 2004; Marden et al., *J Clin Invest* 117:2913-2919, 2007).

Published experiments using common in vivo preclinical models indicate that PACAP-like peptides should be efficacious for the treatment of acute neurological diseases, including (but not limited to) stroke (Reglodi et al., *Stroke* 31:1411-1417, 2000; Chen et al., *Regul Pept* 137:4-19, 2006), the central nervous system sequelae of heart attack (Uchida et al., *Brain Res* 736:280-286, 1996; Lenti et al., *Brain Res* 1283:50-57, 2009) and blunt force trauma to the brain and spinal cord (Farkas et al., *Regul Pept* 123:69-75, 2004; Chen and Tzeng, *Neurosci Lett* 384:117-121, 2005; Kövesdi et al., *Neurotox Res* 13:71-78, 2008).

Huntington's disease is a fatal autosomal dominant disorder that is characterized by progressive cognitive and motor dysfunction. It is caused by expansion of the CAG codon (glutamine) repeat in the gene that codes for huntingtin. The neuropathological hallmark is the degeneration of neurons in the striatum. There are no effective treatments for Huntington's disease or the other CAG codon repeat diseases (such as spinobulbar muscular atrophy and the spinocerebellar ataxias). Published clinical experiments and experiments using common in vivo preclinical models indicate that PACAP-like peptides should be efficacious for the treatment of Huntington's disease or other CAG codon repeat diseases (Emson et al., *Brain Res* 173:174-178, 1979; Tamas et al., *Ann NY Acad Sci* 1070:570-574, 2006; Fahrenkrug et al., *J Mol Neurosci* 31:139-148, 2007).

Published experiments using common in vivo preclinical models indicate that PACAP-like peptides should be efficacious for the treatment of retinal diseases, including (but not limited to) diabetic retinopathy (Szabadfi et al., *VIP, PACAP and Related Peptides* [Ninth International Symposium], Kagoshima, 2009), macular degeneration (Feret et al., *Geriatr Nurs* 28:387-392, 2007; Seki et al., *J Mol Neurosci* 36:57-60, 2008) and glaucoma (Silveira et al., *J Biol Chem* 277: 16075-16080, 2002; Osborne et al., *Prog Retin Eye Res* 23:91-147, 2004; Atlasz et al., *Gen Comp Endocrinol* 153: 108-114, 2007; Seki et al., *J Mol Neurosci* 36:57-60, 2008).

Published experiments using common in vivo preclinical models indicate that PACAP-like peptides should also be efficacious for the treatment of autoimmune diseases, including (but not limited to) rheumatoid arthritis (Abad et al., *J Immunol* 167:3182-3189, 2001; Delgado et al., *Nat Med* 7:563-568, 2001), Crohn's disease (Abad et al., *Gastroenterology* 124:961-971, 2003; Arranz et al., *Neuroimmunomodulation* 15:46-53, 2008), ulcerative colitis (Azuma et al., *J Cell Physiol* 216:111-119, 2008), multiple sclerosis (Kato et al., *Mult Scler* 10:651-659, 2004; Tan et al., *Proc Natl Acad Sci USA* 106:2012-2017, 2009), Sjögren's disease (Lodde et al., *Ann Rheum Dis* 65:195-200, 2006; Nakamachi et al., *VIP, PACAP and Related Peptides* [Ninth International Symposium], Kagoshima, 2009), and type I diabetes (Li et al., *Regul Pept* 145:24-32, 2008). In addition, because of the overlapping mechanisms responsible for the pathogenesis of autoimmune diseases, PACAP-like peptides would be expected to be efficacious for the treatment of scleroderma, idiopathic membranous nephropathy, Guillain-Barre syndrome, Goodpasture's disease, autoimmune hepatitis, myasthenia gravis, Hashimoto's thyroiditis, Graves' disease, pemphigus vulgaris, and lupus erythematosus.

Keratoconjunctivitis sicca (dry eye) is an eye disorder that is caused by decreased tear production or increased tear evaporation, with decreased tear production being far more common. The most common cause of decreased tear production is aging. There are numerous other causes for decreased tear production, including hyposecretion of the lacrimal gland due to destruction, therapeutic agents (such as atropine, tricyclic antidepressants and morphine) or post-radiation fibrosis, and hyposecretion of the lacrimal gland associated with systemic autoimmune diseases (such as Wegener's granulomatosis, lupus erythematosus and, especially, Sjögren's disease). Dry eye is also a common side-effect of LASIK surgery. Published experiments using common in vitro and in vivo preclinical models indicate that PACAP-like peptides should also be efficacious for the treatment of keratoconjunctivitis sicca (dry eye) caused by autoimmune diseases or LASIK surgery (Lodde et al., *Ann Rheum Dis* 65:195-200, 2006; Fukiage et al., *Am J Ophthalmol* 143:255-262, 2007; Gaal et al., *J Mol Neurosci* 36:321-329, 2008; Nakamachi et al., VIP, PACAP and Related Peptides (Ninth International Symposium), Kagoshima, 2009).

The β-cells of the pancreas express both the $PAC_1$ receptor and the $VPAC_2$ receptor (Ahrén, *Ann NY Acad Sci* 1144:28-35, 2008). $PAC_1$ receptor-deficient mice had reduced glucose-stimulated insulin secretion and reduced glucose tolerance compared to wild-type mice (Jamen et al., *J Clin Invest* 105:1307-1315, 2000), while mice chronically treated with the $PAC_1$ receptor-specific agonist maxadilan had increased basal plasma levels of insulin and increased glucose tolerance compared to saline-treated mice (Yu et al., *Peptides* 29:1347-1353, 2008). Mice continuously infused with the $VPAC_2$ receptor-selective agonist BAY 55-9837 had increased basal plasma levels of insulin and increased glucose tolerance compared to saline-treated mice (Tsutsumi et al., *Diabetes* 51:1453-1460, 2002). These published articles indicate that PACAP-like peptides should be efficacious for the treatment of type II diabetes.

Published experiments using common in vivo preclinical models indicate that PACAP-like peptides should be efficacious for the treatment of sepsis caused by bacteria and/or viruses, including bacterial and viral toxins (Delgado et al., *J Immunol* 162:1200-1205, 1999; Martinez et al., *Proc Natl Acad Sci USA* 99:1053-1058, 2002, Martinez et al., *J Leukoc Biol* 77:729-738, 2005; Chorny & Delgado, *Am J Pathol* 172:1297-1307, 2008; Tang et al., *Int Immunopharmacol* 8:1646-1651, 2008).

Published experiments using common in vitro and in vivo preclinical models indicate that PACAP-like peptides should also be efficacious for the treatment of a wide range of acute and chronic cardiovascular diseases, including (but not limited to) myocardial infarction (Sano et al., *Regul Pept* 109: 107-113, 2002; Dvoráková, *Drug News Perspect* 18:387-391, 2005; Gasz et al., *Peptides* 27:87-94, 2006; Roth et al., *Ann NY Acad Sci* 1163:512-516, 2009), atherosclerosis (Oiso et al., *Biochem Cell Biol* 71:156-161, 1993; Chang, *Sheng Li Ke Xue Jin Zhan* 28:132-135, 1997) and restenosis (Oiso et al., *Biochem Cell Biol* 71:156-161, 1993; Bruch et al., *J Vasc Res* 34:11-18, 1997; Sun et al., *J Neuroimmunol* 107:88-99, 2000; Freson et al., *J Clin Invest* 113:905-912, 2004; Zhang et al., *Curr Eye Res* 30:1105-1111, 2005; Joner et al., *Arterioscler Thromb Vasc Biol* 27:182-189, 2007; Lv et al., *Shock* 31:185-191, 2009).

Published experiments using common in vitro and in vivo preclinical models indicate that PACAP-like peptides should be efficacious for the treatment of a wide range of acute renal injuries, including (but not limited to) injuries caused by ischemia/reperfusion (Riera et al., *Transplantation* 72:1217-1223, 2001; Szakaly et al., *J Mol Neurosci* 36:89-96, 2008; see FIGS. 6 and 7), light-chain immunoglobulin overload (Li et al., *Regul Pept* 145:24-32, 2008), and many commonly used therapeutic agents such as gentamicin (Li et al., *Regul Pept* 145:24-32, 2008), streptozotocin (Li et al., *Regul Pept* 145:24-32, 2008), cisplatin (Li et al., *Peptides* 31:592-602, 2010; see FIG. 5), and doxorubicin (Racz et al., *J Mol Neurosci* 42:419-427, 2010; Moru et al., *Circ J* 74:1183-1190).

Published experiments using common in vivo preclinical models indicate that PACAP-like peptides should be efficacious for the treatment of a wide range of acute and chronic pulmonary diseases, including (but not limited to) asthma (Lindén et al., *Thorax* 58:217-221, 2003; Onoue et al., *Peptides* 28:1640-1650, 2007), chronic obstructive pulmonary disease (Kinhult et al., *Peptides* 22:2151-2154, 2001: Onoue et al., *Eur J Biochem* 271:1757-1767, 2004; Onoue et al., *Peptides* 28:1640-1650, 2007), cystic fibrosis (Ameen et al., *J Cell Sci* 112:887-894, 1999; Dérand et al., *Br J Pharmacol* 141:698-708, 2004; Sergejeva et al., *Regul Pept* 117:149-154; 2004; Chappe et al., *J Pharmacol Exp Ther* 327:226-238, 2008; Rafferty et al., *J Pharmacol Exp Ther* 331:2-13, 2009), and pulmonary arterial hypertension (Otto et al., *Circulation* 110:3245-3251, 2004; Haberl et al., *Eur J Hum Genet* 15:18-22, 2007; Said et al., *Circulation* 115:1260-1268, 2007; Szema et al., *VIP, PACAP and Related Peptides* [Ninth International Symposium], Kagoshima, 2009).

Systemic hypertension is a polygenic disease. Polymorphisms in the PACAP gene appear to represent predispositions for the development of systemic hypertension (Rutherford et al., *Am J Med Genet A* 126:241-247, 2004). Thus, the invention also features a method of determining whether a subject (e.g., a mammal, such as a human) has an increased risk of systemic hypertension. In particular, the method involves detecting one or more polymorphisms in the PACAP gene of the subject, wherein the presence of the polymorphisms indicates an increase risk of systemic hypertension in the subject.

Cancer is the leading cause of death in industrialized countries. Chemotherapy is the preferred treatment for disseminated cancers and metastatic tumors. Chemotherapy is also frequently used when surgery or radiation therapy have not completely eradicated a localized tumor, or as an adjunctive treatment with surgery or radiation therapy. Published experiments using common in vitro and in vivo preclinical models indicate that PACAP-like peptides should also be efficacious for the treatment of hematological cancers, including (but not limited to) blood cancers such as lymphoid and myeloid leukemias, lymphomas and plasma cell disorders (Waldenström's macroglobulinemia, multiple myeloma, etc.). The published literature suggests that PACAP-like peptides inhibit the proliferation of most normal hematopoietic cells (e.g., Ottaway and Greenberg, *J Immunol* 132:417-423, 1984; Boudard and Bastide, *J Neurosci Res* 29:29-41, 1991; Tatsuno et al., *Endocrinology* 128:728-734, 1991; Trejter et al., *Histol Histopathol* 16:155-158, 2001). PACAP-like peptides have been shown to inhibit the proliferation of HEL myeloid leukemia cells (Hayez et al., *J Neuroimmunol* 149:167-181, 2004). Two of the inventors of the present invention have shown that PACAP-like peptides potently inhibit the proliferation of multiple myeloma cells (Li et al., *Regul Pept* 145:24-32, 2008; see FIGS. 3 and 4). Two of the inventors of the present invention have also shown that PACAP-like peptides are efficacious in a patient with multiple myeloma (Li et al., *Peptides* 28:1891-1895, 2007). The inventors of the present invention have recently shown that PACAP-like peptides enhance the killing of both lymphoid and myeloid hematopoietic cancer cells by the commonly used anticancer agents carmustine, vincristine and thalidomide (Li et al., PCT/US2009/058445, 2009). Therefore, PACAP-like peptides should be efficacious for the treatment of lymphoid and myeloid hematopoietic cancers both as monotherapeutics and as adjunctive therapeutics with commonly used anticancer agents.

In contrast, the published literature suggests that PACAP-like peptides promote the proliferation and survival of most (though not all) epithelial cancer cells. Oka et al. (*Amer J Pathol* 155:1893-1900, 1999) reported that PACAP protects HP75 human pituitary adenoma cells against apoptotic cell death caused by treatment with transforming growth factor-β31, and PACAP has been shown more recently to protect PC-3 androgen-independent human prostate cancer cells (Gutiérrez-Cañas et al., *Br J Pharmacol* 139:1050-1058, 2003) and CRL-2768 rat schwannoma cells (Castorina et al., *Brain Res* 1241:29-35, 2008) against apoptotic cell death caused by serum withdrawal. Onoue et al. (*FEBS J* 275:5542-5551, 2008) have shown that PACAP protects RIN-m5F insulinoma cells against apoptotic cell death caused by the anticancer agent streptozotocin. In addition, PACAP(6-38), a PACAP/VIP receptor antagonist, inhibited the growth in nude mice of xenografts of PC-3 human prostate cancer cells (Leyton et al., *Cancer Lett* 125:131-139, 1998), NCI-H838 human non-small cell lung cancer cells (Zia et al., *Cancer Res* 55:4886-4891, 1995) and MCF-7 human breast cancer cells (Leyton et al., *Breast Cancer Res Treat* 56:177-186, 1999). Therefore, parenteral administration of PACAP-like peptides cannot be used to treat patients with most (though perhaps not all) solid epithelial tumors. However, parenteral administration of PACAP/VIP receptor antagonists could be used to treat patients with solid epithelial tumors in combination with anticancer agents whose dose-limiting toxicity was myelosuppression.

Glucocorticoids are frequently used for the treatment of patients with blood cancers and autoimmune diseases in order to inhibit the activity of B- and T-lymphocytes. However, a significant portion of the patients treated with glucocorticoids eventually become resistant to the steroid (Barnes & Adcock, *Lancet* 373:1905-1917, 2009). The inventors of the present invention have shown that PACAP-like peptides can still inhibit the proliferation of B-lymphocytes from a patient with multiple myeloma who was being treated with a dexamethasome-containing regimen (Greenstein et al., *Exp Hematol* 31:271-282, 2003) even after the B-lymphocytes have become resistant to dexamethasone (compare FIGS. 8 and 9). These experiments indicate that PACAP-like peptides should be efficacious in patients with blood cancers and autoimmune diseases even after the patients have become resistant to glucocorticoids.

Published experiments using common in vivo preclinical models indicate that PACAP-like peptides should be efficacious for the treatment of eating disorders (Matsuda and Maruyama, *Peptides* 28:1761-1766, 2007; Hawke et al., *J Neurosci* 29:14828-14835, 2009; Mounien et al., *Neuropsychopharmacology* 34:424-435, 2009).

Published experiments using common in vivo preclinical models indicate that PACAP-like peptides should be efficacious for the treatment of a wide range of acute and chronic liver diseases, including (but not limited to) ischemia/reperfusion injury (Leister et al., *Digestion* 66:186-192, 2002; Leister et al., *Int J Colorectal Dis* 20:42-48, 2005), hepatitis (Allam, Immunobiology 212:603-612, 2007; Luo et al., *Eur J Pharmacol* 607:226-233, 2009) and fatty liver (Kono et al., *Am J Physio* 280:G1005-G1012, 2001; Thakur et al., *J Gastroenterol Hepatol* 22 [Suppl 1]:S53-556, 2007; Cederbaum et al., *Arch Toxicol* 83:519-548, 2009).

Osteoporosis is characterized by a reduction in the mineral density of bone and, consequently, an increased risk of bone fractures. It is more common in women than men, especially in postmenopausal women. Osteoporosis is also a common side-effect of many glucocorticoid-containing anticancer therapeutic regimens. Published experiments using common in vitro preclinical models indicate that PACAP-like peptides should be efficacious for the treatment of osteoporosis (Winding et al., *Exp Physiol* 82:871-886, 1997; Mukohyama et al., *Biochem Biophys Res Commun* 271:158-163, 2000).

Pre-eclampsia is a life-threatening disorder that occurs during 5-10% of pregnancies, usually during the second and third trimester. Pre-eclampsia involves damage to the placental endothelium, kidneys and liver. The principal symptoms are systemic hypertension, inflammation and elevated levels of protein in the urine. Published clinical experiments and experiments using common in vitro and in vivo preclinical models indicate that PACAP-like peptides should be efficacious for the treatment of pre-eclampsia (Hoist et al., *Br J Obstet Gynaecol* 98:803-806, 1991; Steenstrup et al., *Regul Pept* 61:197-204, 1996; Kinhult et al., *Peptides* 22:2151-

2154, 2001; Lee et al., *J Hypertens* 21:395-402, 2003; Racz et al., *Gen Comp Endocrinol* 153:115-123, 2007; Li et al., *Regul Pept* 145:24-32, 2008; Reglodi et al., *J Endocrinol Invest* 33:443-445, 2010).

Published experiments using common in vivo preclinical models also indicate that PACAP-like peptides should be efficacious for the treatment of cell (Scharf et al., *J Mol Neurosci* 36:79-88, 2008; Kim et al., *Diabetes* 58:641-651, 2009; Sakuma et al., *Transplant Proc* 41:343-345, 2009) and solid organ transplantation (Alessandrini, *Acta Biomed Ateneo Parmense* 65:59-73, 1994; Riera et al., 2001; Ferencz et al., *J Mol Neurosci* 37:168-176, 2008; Jungraithmayr et al., *Transplantation* 88:478-485, 2009; Zhai et al., *Transplantation* 87:1140-1146, 2009; see FIG. 6).

A PACAP-like peptide plays important roles in learning and memory in Arthropods (Feany and Quinn, *Science* 268: 869-873, 1995; DeZazzo et al., *J Neurosci* 19:8740-8746, 1999). Published experiments in mammals using common in vivo preclinical models indicate that PACAP-like peptides should be efficacious for the treatment of cognitive disorders during normal (Otto et al., *J Neurosci* 21:5520-5527, 2001; Sacchetti et al., *Neurobiol Learn Mem* 76:1-6, 2001) and pathological (Deguil et al., *Neurotox Res.* 17:142-155, 2010) aging.

The AIDS dementia complex (HIV encephalopathy) is a severe cognitive and motor disorder caused by infection of microglial cells in the brain by the human immunodeficiency virus. The pathological features include microglial activation, neuronal apoptosis and demyelination. Stimulation of the $VPAC_2$ receptor has been shown to inhibit integration of the human immunodeficiency virus into genomic DNA (Bokaei et al., *Virology* 362:38-49, 2007). In addition, PACAP has been shown to protect cortical neurons against the toxic effects of the envelope glycoprotein of the human immunodeficiency virus gp120 (Arimura et al., *Ann NY Acad Sci* 739:228-243, 1994; Brenneman et al., *Neuropeptides* 36:271-280, 2002) and to "deactivate" activated microglial cells (Kong et al., *Neuroscience* 91:493-500, 1999; Delgado et al., *Glia* 39:148-161, 2002).

Normal aging of the central nervous system is accompanied by an increase in the levels of proinflammatory cytokines and superoxide, and a decrease in both the number of basal forebrain cholinergic neurons and the rate of proliferation of neural progenitor cells in the subependymal zone of the dentate gyrus (Ye and Johnson, *Neuroimmunomodulation* 9:183-192, 2001; Godbout et al., *FASEB J* 19:1329-1331, 2005; Baskerville et I., *Neuroreport* 17:1819-1823, 2006). Reduction of extracellular superoxide levels and stimulation of neural progenitor cell proliferation in the subependymal zone of the dentate gyrus improves cognitive performance during aging (Sun et al., *Endocrinology* 146:1138-1144, 2005; Hu et al., *J Neurosci* 26:3933-3941, 2006). PACAP has been shown to protect basal forebrain cholinergic neurons against apoptosis, inhibit inflammation, reduce extracellular superoxide levels, stimulate the proliferation of neural progenitor cells in the subependymal zone of the dentate gyrus, and enhance learning and memory (Takei et al., *Eur J Neurosci* 12:2273-2280, 2000; Otto et al., *J Neurosci* 21:5520-5527, 2001; Sacchetti et al., *Neurobiol Learn Mem* 76:1-6; 2001; Mercer et al., *J Neurosci Res* 76:205-215, 2004). Therefore, PACAP-like compounds of the invention should be efficacious for reversing the cognitive and motor decline during normal aging.

The PACAP analogs and compounds of the invention can be coupled to suitable radionuclides and used in the localization, diagnosis and treatment of disseminated cancers and metastatic tumors in humans or other mammals (Raderer et al., *J Nucl Med* 39:1570-1575, 1998; Reubi, *Endocr Rev* 24:389-427, 2003; Zhang et al., *Regul Pept* 144:91-100, 2007; Bodei et al., *J Endocrinol Invest* 32:360-369, 2009), and/or coupled to small molecule therapeutics and used as vectors for targeted drug delivery to humans or other mammals (Reubi, 2003; Moody et al., *Peptides,* 28:1883-1890, 2007).

Examples of suitable radionuclides that can be coupled to the PACAP-like compounds of the invention (e.g., one or more of the PACAP-like compounds having the sequence of Formula (I) (e.g., the sequence of SEQ ID NOs: 4-13)) include, e.g., a γ-emitting radionuclide, Auger-emitting radionuclide, β-emitting radionuclide, an α-emitting radionuclide, or a positron-emitting radionuclide (e.g., $^{11}C$, $^{13}N$, $^{15}O$, $^{18}F$, $^{52}Fe$, $^{55}Co$, $^{61}Cu$, $^{62}Cu$, $^{64}Cu$, $^{67}Cu$, $^{67}Ga$, $^{68}Ga$, $^{62}Zn$, $^{63}Zn$, $^{70}As$, $^{71}As$, $^{74}As$, $^{76}Br$, $^{79}Br$, $^{82}Rb$, $^{86}Y$, $^{89}Zr$, $^{110}In$, $^{111}In$, $^{120}I$, $^{123}I$, $^{124}I$, $^{125}I$, $^{131}I$, $^{122}Xe$, $^{175}Lu$, $^{154}Gd$, $^{155}Gd$, $^{156}Gd$, $^{157}Gd$, $^{158}Gd$, $^{94m}Tc$, $^{94}Tc$, and $^{99m}Tc$). The PACAP analogs and compounds of the invention can also be coupled to suitable imaging agents and used in the localization of granulomas in humans or other mammals with various infectious or autoimmune diseases (e.g., Metwali et al., *J Immunol* 157:265-270, 1996). Examples of suitable imaging agents include, e.g., $^{99m}Tc$, $^{51}Cr$, $^{67}Ga$, $^{68}Ga$, $^{111}In$, $^{168}Yb$, $^{140}La$, $^{90}Y$, $^{88}Y$, $^{153}Sm$, $^{156}Ho$, $^{165}Dy$, $^{64}Cu$, $^{97}Ru$, $^{103}Ru$, $^{186}Re$, $^{188}Re$, $^{203}Pb$, $^{211}Bi$, $^{212}Bi$, $^{213}Bi$, and $^{214}Bi$. Metal components that are useful as detectable labels may be a metal ion from heavy elements or rare earth ions, such as $Gd^{3+}$, $Fe^{3+}$, $Mn^{3+}$, or $Cr^{2+}$. Conjugates that include paramagnetic or superparamagnetic metals are useful as diagnostic agents in MRI imaging applications. Paramagnetic metals that may be used in conjunction with the PACAP-like compounds of the invention include, but are not limited to, chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), and ytterbium (III). Examples of small molecules include compounds having a molecular weight of less than 4,000 g/mol, more preferably having a molecular weight in the range of 200 to 2,000 g/mol, e.g., less than 2,000 g/mol, less than 1,000 g/mol, or even less than 900 g/mol. Examples of small molecules include, but are not limited to camptothecin, homocamptothecin, colchicine, thiocolchicine, combretastatin, dolistatin, doxorubicin, methotrexate, podophyllotoxin, rhizoxin, rhizoxin D, a taxol, paclitaxel, CC1065, and a maytansinoid, as well as those therapeutic and anticancer agents described below.

The maximal tolerable dose of the most commonly used cancer therapeutics is limited by their toxic effects on one or more major organs of the body of humans or other mammals. For example, the dose-limiting toxicity for cancer chemotherapy with cisplatin is nephrotoxicity (Kintzel, *Drug Saf* 24:19-38, 2001), the dose-limiting toxicity for cancer chemotherapy with bleomycin is pulmonary toxicity (Chandler, *Clin Chest Med* 11:21-30, 1990), and the dose-limiting toxicity for cancer chemotherapy with doxorubicin is cardiotoxicity (Takemura & Fujiwara, *Prog Cardiovasc Dis* 49:330-352, 2007). Several strategies have been used to increase the maximal tolerable dose of cancer therapeutics and, thus, increase their therapeutic effectiveness. For example, cancer therapeutics have been conjugated to monoclonal antibodies directed against tumor-associated antigens (Wu & Senter, *Nat Biotechnol* 23:1137-1146, 2005) or to bioactive peptides whose receptors are highly expressed in selected types of tumors (Reubi, 2003) in order to preferentially deliver the anticancer agent to the interior of tumor cells (e.g., somatostatin, bombesin, gastrin-releasing peptide, cholecystokinin/ gastrin, neurotensin, substance P, and neuropeptide Y). An alternate strategy to increase the efficacy of cancer therapeutics is to preferentially protect normal tissues against the cytotoxic effects of the anticancer agents (Hogle, *Semin Oncol Nurs* 23:213-224, 2007).

The U.S. FDA has approved several cytoprotective agents for use with anticancer agents, including amifostine (Ethyol), dexrazoxane (Zinecard) and mesna (Mesenex). None of these cytoprotective agents acts via G-protein-coupled receptors.

Accordingly, the present invention also relates to methods and compositions for the treatment, management, and prevention of injuries to the major organs of the body, such as the brain, heart, lung, kidneys, liver, and gastrointestinal tract, of humans or other mammals caused by trauma, acute or chronic diseases, or one or more prophylactic/therapeutic agents. The method comprises administering an effective amount of one or more of the novel PACAP analogs and compounds of the invention having activities at one or more PACAP/VIP receptors, for the inhibition of the pathology caused by trauma, chronic diseases, or one or more prophylactic/therapeutic agents.

PACAP-like compounds are extremely effective in protecting neurons, cardiomyocytes, hepatocytes, and lung, kidney and gastrointestinal epithelial cells in a concentration-dependent manner. Thus, the present invention relates to a method of treatment of these cells at a concentration of about $10^{-13}$ M to $10^{-6}$ M of the PACAP-like compound. When these cells are in culture, the concentration of the PACAP-like compound is preferably between $10^{-13}$ M and $10^{-6}$ M in the culture medium. When these cells are in the organs of a subject, the concentration of the PACAP-like compound is preferably between about $10^{-13}$ M to $10^{-6}$ M in the interstitial space or blood. Within the generally effective concentration range of the compositions of this invention, there is a peak effectiveness, below which the effectiveness of the composition falls off to a significant degree. In a preferred embodiment, the concentration of the PACAP composition of the present invention is between about $10^{-13}$ M and about $10^{-6}$ M, which permits treatment of the subject with minimal risk of adverse side effects from the treatment (Reglodi et al., 2000; Li et al., 2007). In a preferred embodiment, the concentration of the PACAP-like compound is about $10^{-9}$ M. The present discovery makes possible the use of the compositions of this invention in low concentrations to provide substantial protection of neurons, cardiomyocytes, hepatocytes, and lung, kidney and gastrointestinal epithelial cells. In a specific embodiment, the composition of the present invention protects these cells from injury or death. The injury or death of these cells may be due to trauma, chronic diseases, or one or more prophylactic/therapeutic agents.

The compositions of the present invention may be administered intravenously, intraperitoneally, subcutaneously, intramuscularly, or otherwise into the bloodstream in order to achieve the optimal concentration for the treatment, management or prevention of injuries to one or more of the major organs of the body of humans or other mammals caused by treatment with one or more anticancer agents. The intravenous administration of the composition of the present invention may be as a bolus injection, as a constant infusion or as a bolus injection followed immediately by a constant infusion. In a preferred embodiment, the subject is being treated with one or more chemotherapeutics for a hematological malignancy and the PACAP-like adjuvant is administered as a bolus injection (in order to saturate any serum binding proteins) followed immediately by a constant infusion.

The compositions of the present invention may be administered by inhalation or intranasally in order to have preferential access to the lung (Doberer et al., *Eur J Clin Invest* 37:665-672, 2007) or the brain (Nonaka et al., *J Pharmacol Exp Ther* 325:513-519, 2008), respectively. In a preferred embodiment, a subject is treated by inhalation with one or more novel PACAP analogs for pulmonary arterial hypertension. In another preferred embodiment, a subject is treated intranasally with one or more novel PACAP analogs for a concussion.

The compositions of the present invention may be administered orally in a time-dependent (Gazzaniga et al., *Expert Opin Drug Deliv* 3:583-597, 2006) or a pH-dependent (Gallardo et al., *Pharm Dev Technol* 13:413-4232008) formulation in order to have preferential access to different levels of the gastrointestinal tract or an injured region of the gastrointestinal tract, respectively. In a preferred embodiment, a subject is treated with one or more novel PACAP analogs for Crohn's disease or ulcerative colitis.

The compositions of the present invention may be administered in a controlled-release (Kost and Langer, *Adv Drug Deliv Rev* 46:125-148, 2001) or a sustained-release (Hutchinson and Furr, *J Control Release* 13:279-294, 1990) formulation. In a preferred embodiment, a subject is treated with one or more chemotherapeutics for a hematological malignancy.

The compositions of the present invention may be administered after encapsulation in liposomes (Sethi et al., *Methods Enzymol* 391:377-395, 2005) or microparticles (Almeida and Souto, *Adv Drug Deliv Rev* 59:478-490, 2007).

The compositions of the present invention may be administered transcutaneously after encapsulation in dendrimers (Grayson and Fréchet, *Chem Rev* 101:3819-3868, 2001). In a preferred embodiment, a subject is treated with one or more chemotherapeutics for a hematological malignancy.

The compositions of the present invention may be administered in combination with other cytoprotective adjunctive agents that have different mechanisms of action, such as amifostine, dexrazoxane, mesna, palifermin (human keratinocyte growth factor), and N-acetylcysteine, in order to have an additive or a synergistic effect.

The compositions of the present invention may be used to treat, manage or prevent injuries to one or more major organs of the body of humans or other mammals caused by both unconjugated anticancer agents and anticancer agents reversibly conjugated to a monoclonal antibody (Wu & Senter, *Nat Biotechnol* 23:1137-1146, 2005) or to one or more bioactive peptides, e.g., somatostatin, bombesin, gastrin-releasing peptide, cholecystokinin/gastrin, neurotensin, substance P, and neuropeptide Y (Reubi, *Endocr Rev* 24:389-427, 2003).

The compositions of the present invention may be used to directly enhance the efficacy of some anticancer agents on some cancer cells, especially the anticancer activity of some chemotherapeutics on lymphoid and myeloid hematopoietic cancers.

The compositions of the present invention may be coupled to radionuclides to localize, diagnose and treat disseminated cancers and metastatic tumors.

The compositions of the present invention may be coupled to small molecule therapeutics to target the delivery of the therapeutics preferentially to specific tissues or cell types.

The compositions of the present invention may be coupled to suitable imaging agents to localize granulomas in humans or other mammals with various infectious or autoimmune diseases.

The compositions of the present invention may be used to coat metallic or biodegradable stents to prevent restenosis of coronary arteries or other large arteries (Hwang et al., *Circulation* 104:600-605, 2001; Butt et al., *Future Cardiol* 5:141-157, 2009).

BRIEF DESCRIPTION OF THE DRAWINGS

FIG. 1 is a table showing the primary amino acid sequences of PACAP38 (SEQ ID NO:1), PACAP27 (SEQ ID NO:2), VIP (SEQ ID NO:3), [Pip$^3$, Aib$^{16,28}$,Ala$^{17}$,Lys$^{34}$,D-Lys$^{38}$]PACAP38 (SEQ ID NO:4), [pip$^3$Ala$^{15,17}$,Aib$^{16,28}$,Lys$^{34}$,D-Lys$^{38}$]PACAP38 (SEQ ID NO:5),[Pip$^3$,Ala$^{14,17}$,Aib$^{16,28}$,Lys$^{34}$,D-Lys$^{38}$]PACAP38 (SEQ ID NO:6),[Pip$^3$,Aib$^{16,28}$,Ala$^{17,21}$,Lys$^{34}$,D-Lys$^{38}$] PACAP38 (SEQ ID NO:7),[Pip$^3$,Aib$^{16,28}$,Ala$^{17,20}$,Lys$^{34}$, D -Lys$^{38}$]PACAP38 (SEQ ID NO:8),[Pip$^3$,Aib$^{16}$,Ala$^{17}$] PACAP27 (SEQ ID NO:9), N-acetyl[Pip$^3$,Aib$^{16}$,Ala$^{17}$] PACAP27 (SEQ ID NO:10), [Ala$^{2,17}$,Pip$^3$,Aib$^{16}$]PACAP27 (SEQ ID NO:11), and [Pip$^3$]PACAP38 (SEQ ID NO:12). All of these compounds have been used in the experiments described in either FIG. 3 or FIG. 10 listed below.

FIG. 2 is a table comparing the molecular weights of the ten novel PACAP analogs (SEQ ID NOs 4-13) as determined by matrix-assisted laser desorption/ionization (MALDI) mass spectroscopy (MS) using an Applied Biosystems Voyager DE machine with the calculated molecular weight based on the amino acid composition.

FIG. 3 is a table listing the EC$_{50}$ for the inhibitory effects of PACAP38, PACAP27, VIP, and eight novel PACAP analogs on the proliferation of light-chain immunoglobulin-secreting myeloma cells. The light-chain immunoglobulin-secreting human multiple myeloma cells were cultured in RPMI 1640 medium supplemented with 10% non-inactivated fetal bovine serum and 0.05 mM 2-mercaptoethanol. The effects of PACAP38, PACAP27, VIP, and the eight novel PACAP analogs on myeloma cell proliferation were assessed by determining incorporation of bromodeoxyuridine into DNA during cell division. The number of myeloma cells approximately doubled during the 24-hour incubation period in the absence of treatment with PACAP-like peptides. Five different concentrations, ranging from 10$^{-13}$ M to 10$^{-5}$ M, were tested for PACAP38, PACAP27, VIP, and each of the eight novel PACAP analogs. The EC$_{50}$ was calculated from the concentration response curve using the software package Prism (Graph Pad, San Diego, CA). Each value represents the mean of four-six determinations per experiment. The EC$_{50}$ for PACAP38 is based on the average of four separate experiments, while the EC$_{50}$ for PACAP27 and [Pip$^3$,Aib$^{16,28}$, Ala$^{17}$,Lys$^{34}$,D-LysIPACAP 38 (SEQ ID NO: 4) is based on the average of two separate experiments.

Sequences

Figure 4:
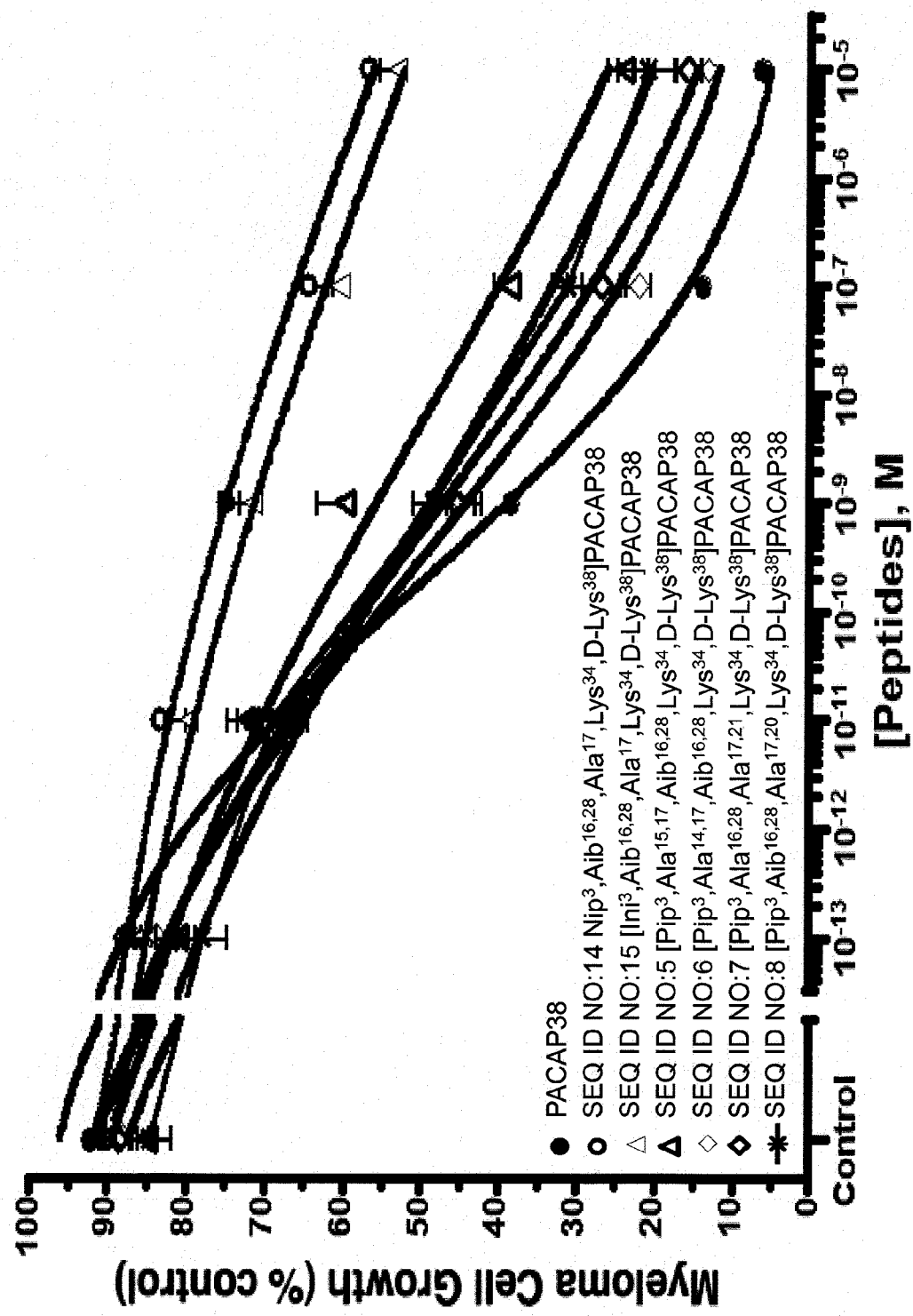
FIG. 4 is a graph showing a representative concentration response curve from a single experiment on the inhibitory effects PACAP38 and six PACAP38 analogs on the proliferation of light-chain immunoglobulin-secreting human myeloma cells. Each value represents the mean plus/minus the standard error of four-six determinations. Note that replacing pipecolic acid in position 3 of the novel analogs with either nipecotic acid or isonipecotic acid results in an analog with more than four orders of magnitude lower inhibitory potency.

SEQ ID NOs:1-3 are human sequences. SEQ ID NOs:4-13 are modifications of the corresponding human sequences. Below is a brief summary of the sequences presented in the accompanying sequence listing, which is incorporated by reference herein in its entirety:

SEQ ID NO:1 is the amino-acid sequence of PACAP38.
SEQ ID NO:2 is the amino-acid sequence of PACAP27.
SEQ ID NO:3 is the amino-acid sequence of VIP.
SEQ ID NO:4 is the amino-acid sequence of [Pip$^3$,Aib$^{16,28}$,Ala$^{17}$,Lys$^{34}$,D-Lys$^{38}$]PACAP38, which can be used for the purposes described in the present invention.
SEQ ID NO:5 is the amino-acid sequence of [Pip$^3$,Ala$^{15,17}$,Aib$^{6,28}$,Lys$^{34}$,D-Lys$^{38}$]PACAP38, which can be used for the purposes described in the present invention.
SEQ ID NO:6 is the amino-acid sequence of [Pip$^3$,Ala$^{14,17}$,Aib$^{16,28}$,Lys$^{34}$,D-Lys$^{38}$]PACAP38, which can be used for the purposes described in the present invention.
SEQ ID NO:7 is the amino-acid sequence of [Pip$^3$,Aib$^{16,28}$,Ala$^{17,21}$,Lys$^{34}$,D-Lys$^{38}$]PACAP38, which can be used for the purposes described in the present invention.
SEQ ID NO:8 is the amino-acid sequence of [Pip$^3$,Aib$^{16,28}$,Ala$^{17,20}$,Lys$^{34}$,D-Lys$^{38}$]PACAP38, which can be used for the purposes described in the present invention.

SEQ ID NO:9 is the amino-acid sequence of [Pip$^3$,Aib$^{16}$,Ala$^{17}$]PACAP27, which can be used for the purposes described in the present invention.
SEQ ID NO:10 is the amino-acid sequence of N-acetyl [Pip$^3$,Aib$^{16}$,Ala$^{17}$]PACAP27, which can be used for the purposes described in the present invention.
SEQ ID NO:11 is the amino-acid sequence of [Ala$^{2,17}$,Pip$^3$,Aib$^{16}$]PACAP27, which can be used for the purposes described in the present invention.
SEQ ID NO:12 is the amino-acid sequence of [Pip$^3$]PACAP38, which can be used for the purposes described in the present invention.
SEQ ID NO:13 is the amino-acid sequence of N-acetyl [Pip$^3$]PACAP38, which can be used for the purposes described in the present invention.

Definitions

The following standard three-letter abbreviations are used herein to identify amino acid residues.
Abu, α-aminobutyric acid
Acb, 1-amino-1-cyclobutanecarboxylic acid
Ach, 1-amino-1-cyclohexanecarboxylic acid
Acpe, 1-amino-1-cyclopentanecarboxylic acid
Acpr, 1-amino-1-cyclopropanecarboxylic acid
Aib, α-aminoisobutyric acid
Ala, alanine
Arg, arginine
Asn, asparagine
Asp, aspartic acid
Bip, 4-biphenylalanine
Cha, cyclohexylalanine
Cys, cysteine
Dab, diaminobutyric acid
Dap, diaminopropionic acid
Gaba, γ-amino-N-butyric acid
Gln, glutamine
Glu, glutamic acid
Gly, glycine
His, histidine
hSer, homoserine
Hyp, hydroxyproline
Ile, isoleucine
Ini, isonipecotic acid
Leu, leucine
Lys, lysine
N-Me-Asp, N-methylaspartic acid
N-Me-Ser, N-methylserine
Met, methionine
Nal, 2-naphthylalanine
Nip, nipecotic acid
Nle, norleucine
Nva, norvaline
Orn, ornithine
Pal, 3-pyridylalanine
Phe, phenylalanine
Pip, pipecolic acid
Pro, proline
Sar, sarcosine (N-methylglycine)
Ser, serine
Thr, threonine
Trp, tryptophan
Tyr, tyrosine
Val, valine As used herein, the term "PACAP" refers to human PACAP27 (SEQ ID NO:2) and/or human PACAP38 (SEQ ID NO:1).

As used herein, the term "PACAP/VIP agonist" refers to any molecule, including a protein, naturally or synthetically post-translationally modified protein, polypeptide, naturally or synthetically modified polypeptide, peptide, naturally or synthetically modified peptide, and large or small nonpeptide molecule that binds to and stimulates one or more of the PACAP/VIP receptors.

As used herein, the term "analog" refers to both conformational and linear sequence analogs. Maxadilan, a 61-amino-acid peptide with two disulfide bridges that is synthesized naturally in the salivary glands of the hematophagous sand fly *Lutzomyia longipalpis*, is one example of a conformational analog of PACAP. It has no obvious linear amino-acid sequence identities with PACAP but binds preferentially to the $PAC_1$ receptors with high affinity (Tatsuno et al., *Brain Res* 889:138-148, 2001; Lerner et al., *Peptides* 28:1651-1654, 2007). The amino-acid sequences of maxadilan made by sand flies from different regions of Central and South America can differ by more than 20%. However, the relative positions of the cysteine residues in these bioactive orthologs are invariant and all of these bioactive orthologs have a similar predicted secondary structure. The amino-acid sequences of some naturally occurring maxadilans are described by Lanzaro et al. (*Insect Mol Biol* 8:267-275, 1999). Therefore, linear analogs of conformational analogs of PACAP, such as linear analogs of maxadilan (Reddy et al., *J Biol Chem* 281:16197-16201, 2006), would be expected to bind to and stimulate PACAP/VIP receptors. Those skilled in the art will recognize that additional conformational analogs of PACAP could be created by synthetic combinatorial chemistry or phage display technologies. A peptide analog may contain one or more amino acids that occur naturally in mammalian cells but do not occur naturally in mammalian peptides. For example (but not by way of limitation), a peptide analog may contain γ-amino-N-butyric acid (GABA), β-alanine, ornithine, and citrulline. An analog of a peptide may also contain one or more nonnatural amino acids that do not occur naturally in mammalian cells. For example (but not by way of limitation), an analog of a peptide may also contain D-alanine, naphthylalanine, pyridylalanine, and norleucine. An analog may have an extension of one or more naturally occurring and/or non-natural amino acids at its amino terminus and/or its carboxyl terminus. The extension at the amino terminus and/or the carboxyl terminus may include one or more additional copies of the same peptide and/or other bioactive peptides (e.g., gastrin-releasing peptide, cholecystokinin/gastrin, neurotensin, substance P, and neuropeptide Y). The extension at the amino terminus and/or the carboxyl terminus may include one or more sites for proteolytic processing in order to make the extended peptide function as a precursor (prodrug) for the bioactive peptide. For example, the PACAP-like compounds may include cleavage sites at the amino terminus and/or the carboxyl terminus for one or more of the following proteolytic enzymes: trypsin, chymotrypsin, a prohormone convertase (e.g., prohormone convertase 1, 2, 4, 5, or 7), furin, chymase, thrombin, calpain, a cathepsin (e.g., cathepsin A, B, D, G, H, or L), papain, Factor Xa, Factor IXa, Factor XIa, renin, chymosin (rennin), thermolysin, a kallikrein, an elastase, and a matrix metalloproteinase.

As used herein, the term "PACAP-like compound" refers to human PACAP27 (SEQ ID NO:2), human PACAP38 (SEQ ID NO:1), human VIP (SEQ ID NO:3), lizard PACAP38 (Valiante et al., *Brain Res* 1127:66-75, 2007), frog PACAP38 (Chartrel et al., *Endocrinology* 129:3367-3371, 1991), and sand fly maxadilan (Lanzaro et al., *Insect Mol Biol* 8:267-275, 1999), and peptides or peptidomimetic compounds that are orthologs, paralogs, analogs, fragments, or derivatives of these naturally occurring peptides and that have agonist activity at one or more PACAP/VIP receptors. PACAP-like compounds of the invention include those having the sequence set forth in SEQ ID NOs: 4-13 and polypeptides having at least 75, 80, 85, 90, 95, 97, 95, or 99% or more sequence identity to the sequence of SEQ ID NOs: 4-13.

As used herein, the term "peptidomimetic" refers to both hybrid peptide/organic molecules and nonpeptide organic molecules that have critical functional groups in a three-dimensional orientation that is functionally equivalent to the corresponding peptide (Marshall, *Tetrahedron* 49:3547-3558, 1993). Peptidomimetic compounds that are functionally equivalents to the PACAP-like compounds of the present invention can be rationally designed by those skilled in the art based on published structure-activity studies (e.g., Igarashi et al., *J Pharmacol Exp Ther* 301:37-50, 2002; Igarashi et al., *J Pharmacol Exp Ther* 303:445-460, 2002; Bourgault et al., *Peptides* 29:919-932, 2008; Bourgault et al., *J Med Chem* 52:3308-3316, 2009).

The terms "percent identity" and "percent similarity" can be used to compare the amino-acid sequences of two peptides. To determine the percent identity of two amino acid sequences, the sequences are aligned for optimal comparison purposes (e.g., gaps can be introduced in the sequence of a first amino-acid sequence for optimal alignment with a second amino-acid sequence). The amino-acid residues at the corresponding amino-acid positions are then compared. When a position in the first sequence is occupied by the same amino-acid residue at the corresponding position in the second sequence, then the molecules are identical at that position. The percent identity between the two sequences is a function of the number of identical positions shared by the sequences (i.e., % identity=the number of identical overlapping positions/total number of positions×100%). In the most common embodiment, the two amino-acid sequences are the same length. To determine the percent similarity of two amino acid sequences, the sequences are also aligned for optimal comparison purposes. When a position in the first sequence is occupied by either the same amino-acid residue or a "conserved" amino acid at the corresponding position in the second sequence, then the molecules are similar at that position. The percent similarity between the two sequences is a function of the number of corresponding positions in the amino acid sequences at which the amino acids are either identical or the different amino acids are conserved substituents (i.e., % similarity=the number of identical or conserved overlapping positions/total number of positions×100%). A conservative substitution is a substitution of one amino acid by another amino acid with a similar side-chain. A conservative substitution frequently results in an analog with similar physical and biological properties. The following is a list of commonly defined classes of "similar" amino acids that occur naturally in mammalian peptides.

Aromatic side-chain: phenylalanine≅tyrosine≅tryptophan≅histidine

Acidic side-chain: aspartic acid≅glutamic acid

Basic side-chain: arginine≅lysine≅histidine

β-Branched side-chain: threonine≅valine≅isoleucine

Nonpolar side-chain: alanine≅valine≅leucine≅proline≅methionine phenylalanine≅tryptophan Uncharged polar side-chain: glycine≅asparagine≅glutamine≅serine threonine≅cysteine≅tyrosine Those skilled in the art will recognize that many amino acids that occur naturally in mammalian cells but do not occur naturally in mammalian peptides and many nonnatural amino acids that do not occur naturally in mammalian cells can be substituted conservatively for one or more of the amino acids that occur naturally in mammalian peptides. For example (but not by way of limitation), hydroxyproline, dehydroproline and N-alkylamino acids could be substituted conservatively for proline, sarcosine, dialkylglycine and α-aminocycloalkane carboxylic acid could be substituted conservatively for glycine, and α-aminoisobutyric acid, naphthylalanine and pyridylalanine could be substituted conservatively for alanine. "Percent identity" and "percent similarity" are determined after optimal alignment of the two sequences without or without the introduction of one or more gaps in one or both amino-acid sequences. There are many algorithms that are well known to those skilled in the art that can be used to determine the optimal alignment. In the most common embodiment, the two amino-acid sequences are the same length.

As used herein, the term "fragment" in the context of PACAP-like or VIP-like peptides refers to a peptide that has fewer amino acids than the PACAP-like or VIP-like peptide and has at least five amino acids with sequence similarity to the PACAP-like or VIP-like peptide, respectively.

As used herein, the term "derivative" refers to a peptide that has been modified by the covalent attachment of another molecule and/or a functional group to the peptide chain. For example (but not by way of limitation), a derivative of a peptide may be produced by glycosylation, acetylation, pegylation, acylation, alkylation, oxidation, phosphorylation, sulfation, formylation, methylation, demethylation, amidation, gamma-carboxylation, cyclization, lactamization, prenylation, myristoylation, iodination, selenoylation, ribosylation, ubiquitination, or hydroxylation. The derivatized peptide can be a peptide analog. A derivative of a peptide can easily be made by standard techniques known to those of skilled in the art. A derivative of a peptide may possess an identical function(s) to the parent peptide. A derivative of a peptide may also have one or more other functions in addition to the function(s) of the parent peptide. For example (but not by way of limitation), a derivative of a peptide may have a longer half-life than the parent peptide and/or have cytoprotective or cytotoxic properties that are not possessed by the parent peptide.

As used herein, the term "subject" refers to either a non-primate (e.g., a cow, pig, horse, cat, dog, rat, etc.) or a primate (e.g., a monkey or a human being, most preferably a human being. In a specific embodiment, the subject is a farm animal (e.g., a horse, pig, lamb or cow) or a pet (e.g., a dog, cat, rabbit, or monkey). In another embodiment, the subject is an animal other than a farm animal or a pet (e.g., a mouse, rat or guinea pig). In a preferred embodiment, the subject is a normal human being. In another preferred embodiment, the subject is a human that has an untreated or treated cancer.

As used herein, the term "in combination with" refers to the use of more than one therapeutic or cytoprotective agent. The use of the term "in combination with" does not restrict the order in which the therapeutic or cytoprotective agent is administered to a subject. One therapeutic or cytoprotective agent can be administered prior to, concomitantly with, or subsequent to the administration of the other therapeutic or cytoprotective agent. The therapies are administered to a subject in a sequence and within a time interval such that the PACAP-like compound(s) of the present invention can act together with the other agent to provide a different response from the subject, preferably a greater therapeutic or cytoprotective benefit, than if they were administered otherwise.

As used herein, the term "nervous system" refers to the central nervous system (the brain and spinal cord), the sympathetic nervous system, the parasympathetic nervous system, and the enteric nervous system.

As used herein, the term "gastrointestinal tract" refers to the pharynx, esophagus, stomach, small intestine, pancreas, and large intestine.

As used herein, the term "hematological malignancies" refers to cancers of blood cells, bone marrow cells or cells of the lymph nodes, including (but not limited to) leukemias, lymphomas and plasma cell dyscrasias.

As used herein, the phrase "plasma cell dyscrasias" refers to monoclonal neoplasms of the B-lymphocyte lineage, including (but not limited to) multiple myeloma, Waldenström's macroglobulinemia, POEMS syndrome, Seligman's disease, and Franklin's disease.

As used herein, the adjective "hematopoietic" refers to cells (including cancer cells) that are derived from hematopoietic stem cells. The normal cells of the body that are derived from hematopoietic stem cells include (but are not limited to) erythrocytes, granulocytes (basophils, eosinophils and neutrophils), lymphocytes, monocytes (macrophages, microglia, splenocytes, and dendritic cells), and thrombocytes.

As used herein, the term "about" refers to a value that is ±10% of the recited value.

DETAILED DESCRIPTION OF THE INVENTION

The inventors of the present patent application have discovered that replacing aspartic acid in position 3 of native human PACAP27 or PACAP38 with pipecolic acid results in a series of novel PACAP analogs (SEQ ID NOs: 4-13, FIG. 1 and FIG. 2) with unique pharmacological properties. In addition, amino-acid substitutions in other positions of the PACAP analogs besides position 3 can be made in order to block proteolysis and/or renal clearance, reduce the cost of synthesis, and alter tissue distribution and/or receptor specificity.

The inventors of the present patent application have discovered that one or more of these novel PACAP analogs are extremely potent inhibitors of the proliferation of human multiple myeloma cells in vitro (FIGS. 3 and 4).

Figure 5:
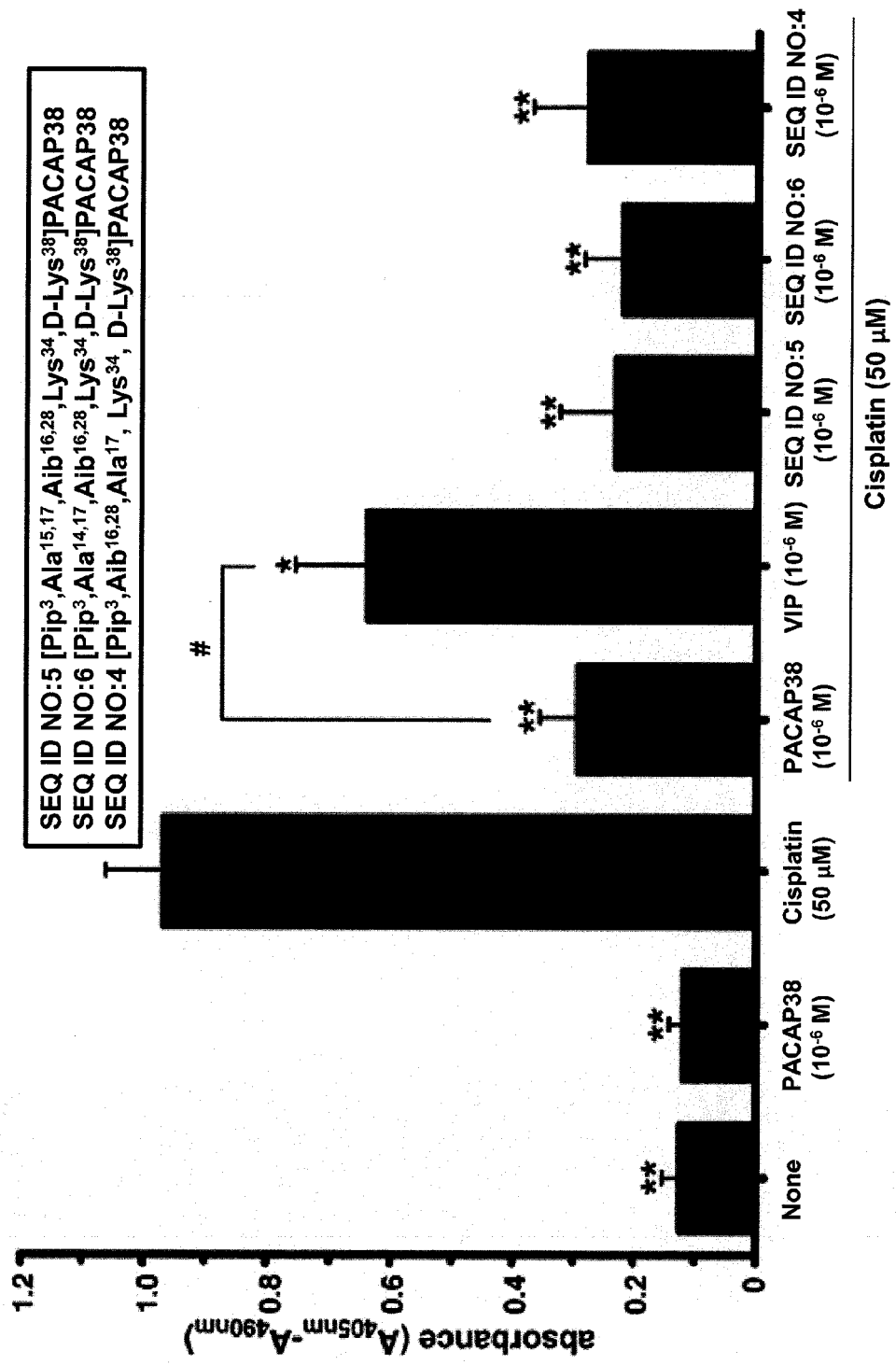
FIG. 5 is a graph showing the reduction in cisplatin-induced apoptotic cell death of rat renal proximal tubule epithelial cells caused by comparable concentrations of PACAP38, VIP and three novel PACAP38 analogs. Primary cultures of renal proximal tubule epithelial cells were made from the kidneys of 6- to 8-weeks-old mice. Kidney cortices were dissected from the medulla, minced and filtered. The tubule cells were purified by repeated centrifugation and washing. The final pellet was resuspended in medium, and the tubule cells were placed in a collagen-coated dish and incubated at 37° C. The medium was then changed every 2 to 3 days until the cells were confluent. Cells were checked for the expression of γ-glutamyltranspeptidase and alkaline phosphatase, markers for renal proximal tubule epithelial cells. All three PACAP38 analogs appeared to be at least as potent as PACAP38 in the in vitro bioassay. VIP was significantly (#p<0.05) less potent than PACAP38. The inhibitory effects of PACAP38, VIP and the three PACAP38 analogs on apoptotic cell death was assessed by the quantitative determination of cytoplasmic histone-associated DNA-fragmentation (mono- and oligonucleosomes) after exposure to cisplatin for 24 hours. Each value represents the mean plus/minus the standard deviation of eight determinations. **p<0.01 and *p<0.05 compared to the group treated only with cisplatin. #p<0.05 compared to the group treated with cisplatin and 10$^{-6}$ M VIP.

The inventors of the present patent application have discovered that the nephrotoxicity caused by cisplatin in primary cultures rat renal tubule epithelial cells can be dramatically reduced by these novel PACAP analogs (FIG. 5).

Figure 6:
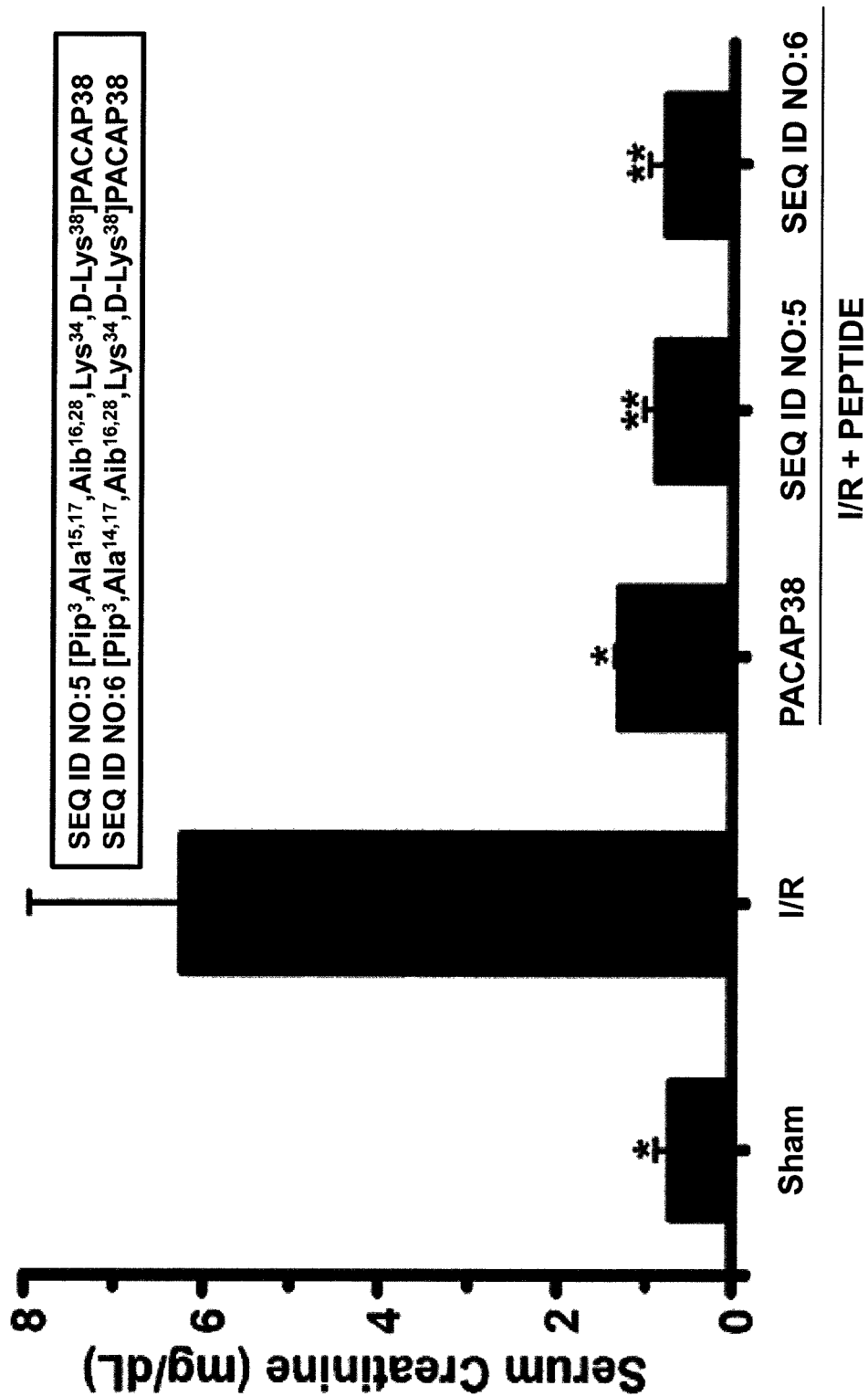
FIG. 6 is a graph showing the effects of PACAP38 and two novel PACAP analogs on serum creatinine levels in mice following ischemia/reperfusion injury to the kidney. The renal artery in male C57BL/6 mice was clamped bilaterally for 45 minutes in all mice except for the sham-operated mice. Twenty micrograms of PACAP38 or one of the PACAP analogs were given intraperitoneally 1 hour after the start of reperfusion and additional doses were given at 24 and 48 hours after the initial dose. The sham-operated group of mice was injected intraperitoneally with PACAP38 on the same schedule as the mice subjected to ischemia/reperfusion. The control group of mice was injected intraperitoneally with the same volume of saline as for the injections of PACAP38 on the same schedule. All of the mice were euthanized 24 hours after the final injection of saline, PACAP38 or one of the novel PACAP analogs. Each value represents the mean plus/minus the standard error of four determinations. **p<0.01 and *p<0.05 compared to the ischemia/reperfusion group treated with saline. I/R, ischemia/reperfusion; sham, sham-operated.

The inventors of the present patent application have discovered that the increase in serum creatinine caused by ischemia/reperfusion injury to the kidney can be dramatically reduced by these novel PACAP analogs (FIG. 6).

Figure 7:
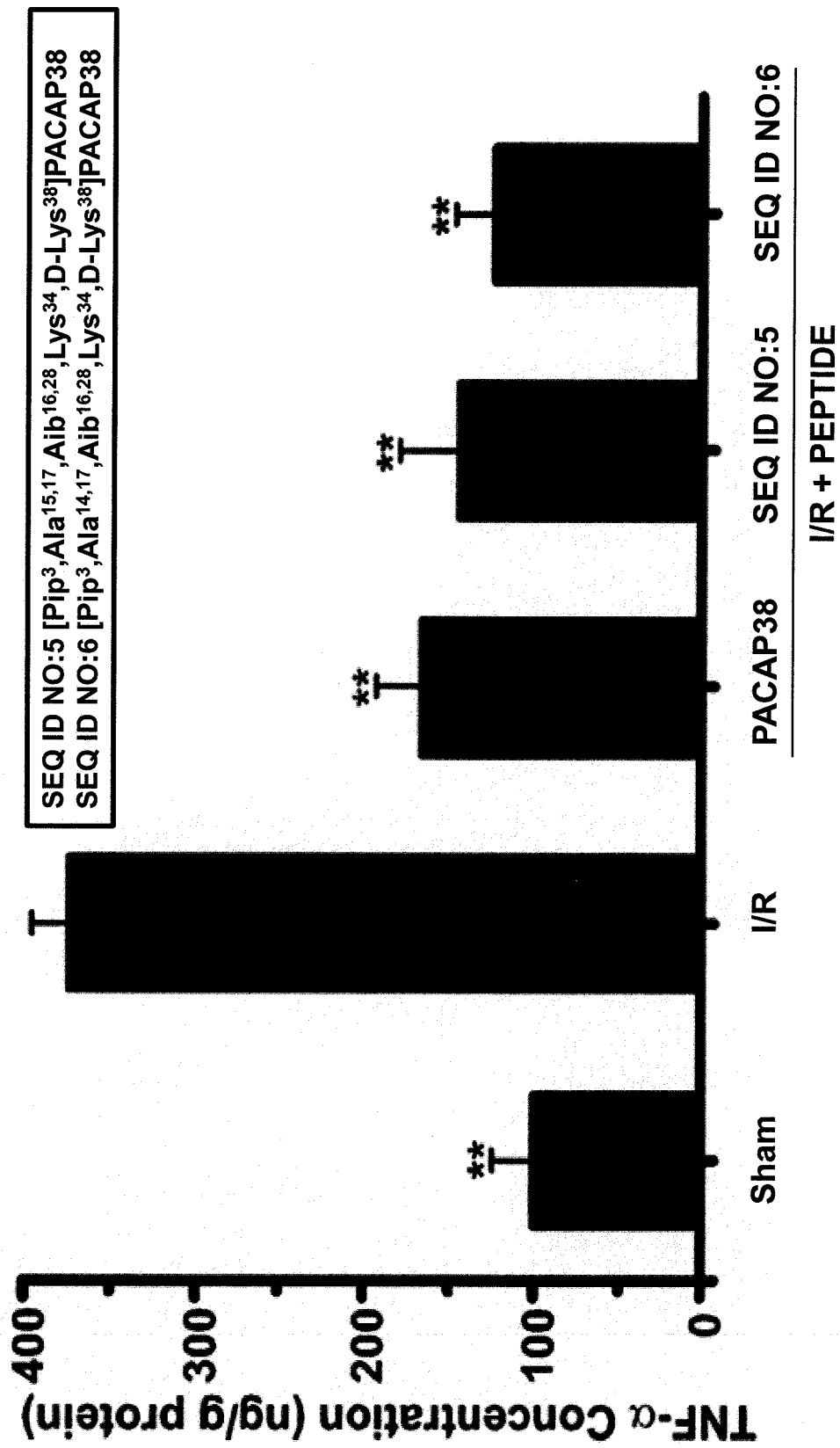
FIG. 7 is a graph showing the effects of PACAP38 and two novel PACAP analogs on the production of TNF-α in the kidneys of mice following ischemia/reperfusion injury to the kidney. The renal artery in male C57BL/6 mice was clamped for 45 minutes in all mice except for the sham-operated mice. Twenty micrograms of PACAP38 or one of the PACAP analogs were given intraperitoneally 1 hour after the start of reperfusion and additional doses were given at 24 and 48 hours after the initial dose. The sham-operated group of mice was injected intraperitoneally with PACAP38 on the same schedule as the mice subjected to ischemia/reperfusion. The control group of mice was injected intraperitoneally with the same volume of saline as for the injections of PACAP38 on the same schedule. All of the mice were euthanized 24 hours after the final injection of saline, PACAP38 or one of the PACAP analogs. Each value represents the mean plus/minus the standard error of four determinations. **p<0.01 compared to the ischemia/reperfusion group treated with saline. I/R, ischemia/reperfusion; sham, sham-operated.

The inventors of the present patent application have discovered that the increase in the levels of tumor necrosis factor-α in the kidney caused by ischemia/reperfusion injury to the kidney can be dramatically reduced by these novel PACAP analogs (FIG. 7).

Figure 8:
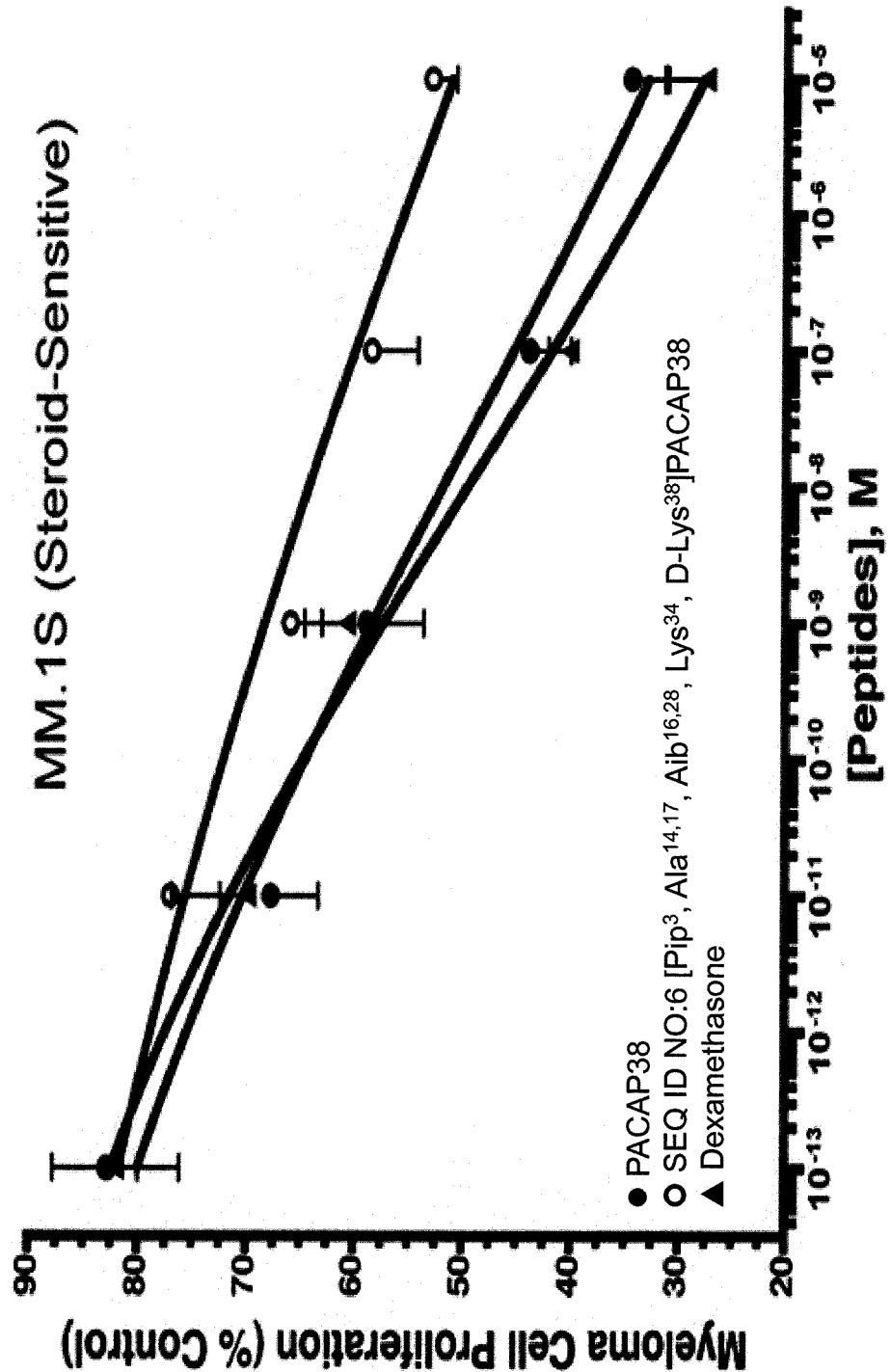
FIG. 8 is a graph showing the effects PACAP38, [Pip$^3$, Ala$^{14,17}$,Aib$^{16,28}$,Lys$^{34}$,D-Lys$^{38}$ (SEQ ID NO: 6) and dexamethasone on the proliferation of light-chain immunoglobulin-secreting human myeloma cell line (MM.1S) that was derived from a patient who was being treated for multiple myeloma with a dexamethasome-containing regimen. The light-chain immunoglobulin-secreting multiple myeloma cells were cultured in RPMI 1640 medium supplemented with 10% non-inactivated fetal bovine serum and 0.05mM 2-mercaptoethanol. The effects of dexamethasone, PACAP38 and the novel PACAP38analog on cell proliferation were assessed by determining the incorporation of bromodeoxyuridine into DNA during cell division. Each value represents the mean plus/minus the standard error of four-six determinations. The cell lines in FIGS. 8 and 9 were obtained from the same patient at different stages of the treatment (Greenstein et al., *Exp Hematol* 31 :271-282, 2003).
Figure 9:
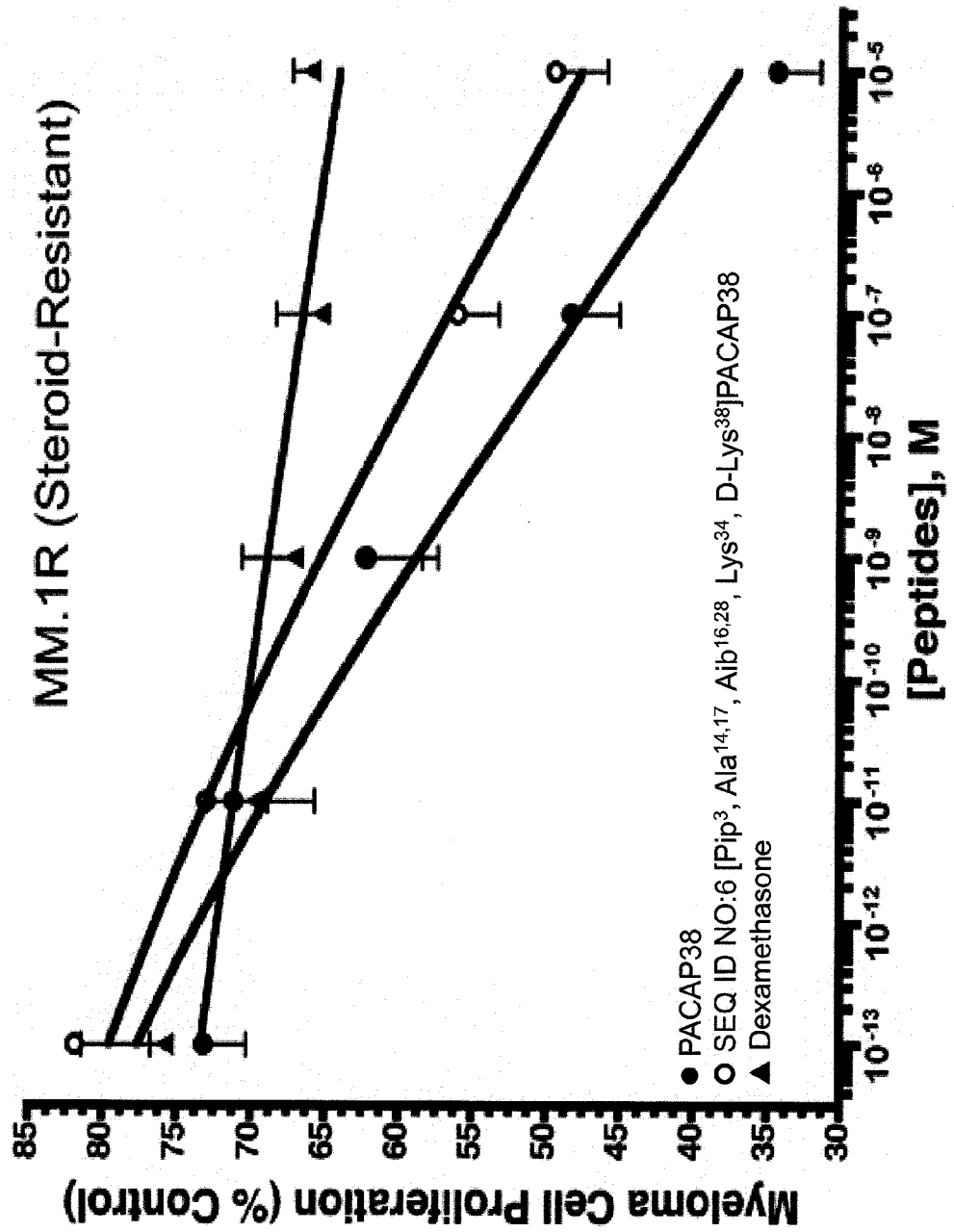
FIG. 9 is a graph showing the effects PACAP38, [Pip$^3$,Ala$^{14,17}$,Aib$^{16,28}$,Lys$^{34}$,D-Lys$^{38}$] PACAP38(SEQ ID NO: 6) and dexamethasone on the proliferation of light-chain immunoglobulin-secreting human myeloma cell line (MM.1 R) that was derived from a patient who was being treated for multiple myeloma with a dexamethasome-containing regimen. The light-chain immunoglobulin-secreting multiple myeloma cells were cultured in RPMI 1640 medium supplemented with 10% non-inactivated fetal bovine serum and 0.05mM 2-mercaptoethanol. The effects of dexamethasone, PACAP38 and the novel PACAP38 analog on cell proliferation were assessed by determining the incorporation of bromodeoxyuridine into DNA during cell division. Each value represents the mean plus/minus the standard error of four-six determination. The cell lines in FIGS. 8 and 9 were obtained from the same patient at different stages of the treatment (Greenstein et al., *Exp Hematol* 31 :271-282, 2003).

The inventors of the present patent application have discovered that these novel PACAP analogs are still highly effective in lymphocytes that have become resistant to corticosteroids (FIGS. 8 and 9).

Figure 10:
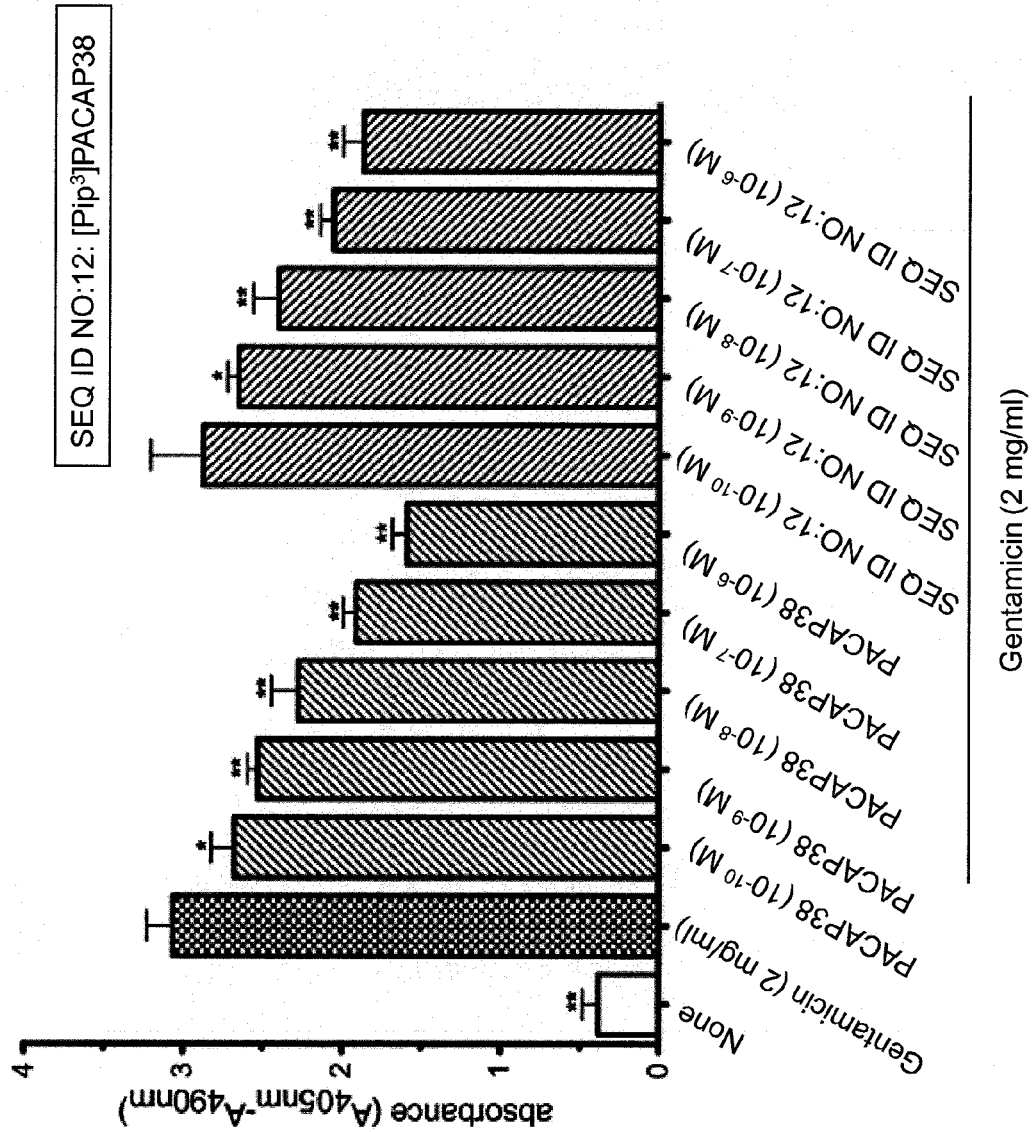
FIG. 10 shows the reduction in gentamicin-induced apoptotic cell death of human renal proximal tubule epithelial cells caused by various concentrations of PACAP38 and [Pip$^3$]PACAP38. The inhibitory effects of PACAP38 and the novel PACAP analog on apoptotic cell death was assessed by the quantitative determination of cytoplasmic histone-associated DNA-fragmentation (mono- and oligonucleosomes) after exposure to gentamicin for 24 hours. Both PACAP38 and [Pip$^3$]PACAP38 produced a dose-dependent inhibition of apoptosis, but the novel analog appeared to be less potent than PACAP38 in this in vitro model of aminoglycoside-induced renal proximal tubule epithelial cell injury. Each value represents the mean plus/minus the standard deviation of four determinations. **$p<0.01$ and *$p<0.05$ compared to the group treated only with gentamicin.

The inventors of the present patent application have discovered that the nephrotoxicity caused by gentamicin in cultured human renal proximal tubule epithelial cells can be dramatically reduced by PACAP38 and a novel PACAP analog (FIG. 10).

The inventors of the present patent application have discovered that these novel PACAP analogs can be used as prophylactic/therapeutic agents for a wide range of medical disorders, including (but not limited to) age-related neurodegenerative diseases (such as Alzheimer's disease, Parkinson's disease and amyotrophic lateral sclerosis), injuries to the central nervous system caused by stroke, heart attack and blunt force trauma (such as concussions and spinal cord trauma), Huntington's disease and other CAG codon repeat expansion diseases, retinal diseases (such as diabetic retinopathy, macular degeneration and glaucoma), autoimmune diseases (such as rheumatoid arthritis, Crohn's disease, ulcerative colitis, scleroderma, Sjögren's disease, idiopathic membranous nephropathy, Goodpasture's disease, autoimmune hepatitis, myasthenia gravis, multiple sclerosis, Guillain-Barré syndrome, type I diabetes, Hashimoto's thyroiditis, Graves' disease, pemphigus vulgaris, and lupus erythematosus), keratoconjunctivitis sicca caused by autoimmune diseases or LASIK surgery, type II diabetes, sepsis caused by bacteria and/or viruses (including bacterial and viral toxins), acute and chronic cardiovascular diseases (such as myocardial infarction, atherosclerosis and restenosis), acute and chronic renal diseases (such as ischemia/reperfusion injury, nephritis and drug-induced nephrotoxicity), acute and chronic pulmonary diseases (such as asthma, chronic obstructive pulmonary disease, cystic fibrosis, and pulmonary arterial hypertension), systemic hypertension, hematological cancers (such as leukemias, lymphomas and plasma cell dyscrasias), eating disorders, acute and chronic liver diseases (such as ischemia/reperfusion injury, hepatitis and fatty liver), osteoporosis, pre-eclampsia, cell and solid organ transplantation, cognitive disorders, AIDS dementia complex, and aging of the central nervous system.

The inventors of the present patent application have discovered that these PACAP analogs coupled to suitable radionuclides can be used in the localization, diagnosis and treatment of disseminated cancers and metastatic tumors, and coupled to small molecule therapeutics can be used as vectors for targeted drug delivery. The inventors of the present patent application have discovered that these novel PACAP analogs coupled to suitable imaging agents can also be used in the localization of granulomas in humans or other mammals with various infectious or autoimmune diseases.

Identification of PACAP-Like Compounds

The present invention provides methods for assaying and screening for PACAP-like activity by incubating the compounds with epithelial cells containing one or more PACAP/VIP receptors, e.g., kidney, lung or liver epithelial cells, and multiple myeloma cells, and then assaying for a reduction in a pathology-causing cell phenotype and inhibition of multiple myeloma cell proliferation, respectively (Li et al., Regul Pept 145:24-32, 2008). For example, a PACAP-like peptide or peptidomimetic should increase the viability of cisplatin-treated kidney epithelial cells and decrease the rate of proliferation of multiple myeloma cells. In addition, the intrinsic activity of any PACAP-like compound at each of the three PACAP/VIP receptors can be determined in stably transfected cell lines that express only one of these receptors by measuring the intracellular accumulation of cyclic AMP (Tatsuno et al., Brain Res 889:138-148, 2001). Radioligand receptor binding assays can be used to determine the affinity of a compound for each of the PACAP/VIP receptors. However, radioligand receptor binding assays do not differentiate between receptor agonists and receptor antagonists. Therefore, other types of assays well known to those skilled in the art must be used to discriminate between PACAP/VIP receptor agonists and PACAP/VIP receptor antagonists.

The viability of renal, pulmonary, hepatic, and neuronal epithelial cells can be determined by a variety of techniques well known to those skilled in the art, including (but not limited to) quantification of the fragmentation of nuclear DNA or caspase 3 activity, quantification of annexin V binding, counting of apoptotic (pyknotic) cells and counting of Trypan blue-positive cells. In the preferred embodiment, the fragmentation of nuclear DNA or caspase 3 activity is determined.

The cell proliferation of hematopoietic and epithelial cells can be determined by a variety of techniques well known to those skilled in the art, including (but not limited to) quantification of the incorporation of bromodeoxyuridine or [$^3$H]thymidine into nuclear DNA, counting of the number of cells expressing proliferating cell nuclear antigen and counting of mitotic figures. In the preferred embodiment, the incorporation of bromodeoxyuridine or [$^3$H]thymidine into nuclear DNA is determined.

The intracellular accumulation of cyclic AMP in stably transfected cell lines that express only one of these receptors can be determined following stimulation with PACAP-like compounds by a variety of techniques well known to those skilled in the art, including (but not limited to) a radioimmunoassay or an enzyme-linked immunosorbent assay. The stimulation is stopped by the addition of ice-cold 20% trifluoroacetic acid. The cAMP is extracted from the cells, the extracts are centrifuged, the supernatants are placed into small plastic vials, and the supernatants are lyophilized for assay of the levels of cAMP. In the preferred embodiment, the intracellular levels of cAMP are quantified with an enzyme-linked immunosorbent assay.

Patient Populations

The present invention provides methods for treating, preventing and managing damage caused by trauma, acute or chronic diseases, or one or more prophylactic/therapeutic agents to one or more major organs of the body, especially, nervous system, heart, lung, kidneys, liver, and gastrointestinal tract, of humans or other mammals by the therapeutic or prophylactic administration of effective amounts of one or more compositions of the present invention. In another embodiment, the composition of the present invention can be administered in combination with one or more other cytoprotective agents.

The methods and compositions of the present invention consists of the administration of one or more compositions of the invention to subjects with injuries caused by trauma, acute or chronic diseases, or one or more prophylactic/therapeutic agents who have suffered from, are suffering from or are expected to suffer from the side-effects of one or more prophylactic/therapeutic agents (e.g., an anticancer agent, a steroid (e.g., a corticosteroid or a glucocorticoid), an anti-inflammatory agent, or an aminoglycoside). In a preferred embodiment, the subject has been, is being or is expected to be administered one or more cancer chemotherapeutics for a hematological malignancy. In the most preferred embodiment, the hematological malignancy is multiple myeloma.

The subjects may or may not have previously been treated on one or more occasions for trauma injuries, acute or chronic diseases, or the side-effects of one or more prophylactic/therapeutic agents. The subjects may or may not have previously been refractory to one or more prophylactic/therapeutic agents (e.g., a cancer chemotherapeutic). The methods and compositions of the present invention may be used as an adjuvant for a first line, second line or nonstandard treatment regimen for trauma, acute or chronic diseases, or the side-effects of one or more prophylactic/therapeutic agents. The methods and compositions of the present invention can be used before any trauma, acute or chronic diseases, or the side-effects of one or more prophylactic/therapeutic agents are observed or after the first or later observations of any trauma, acute or chronic diseases, or the side-effects of one or more prophylactic/therapeutic agents.

Other Therapeutic/Prophylactic Agents

In some embodiments, the present invention provides methods for treating, managing or preventing of injuries to one or more of the major organs of the body of humans or other mammals caused by trauma, acute or chronic diseases, or one or more prophylactic/therapeutic agents by administering one or more compositions of the present invention in combination with one or more other cytoprotective agents. These other cytoprotective agents include (but are not limited to) amifostine, dexrazoxane, mesna, palifermin, and N-acetylcysteine. None of the listed cytoprotective agents stimulate G-protein-coupled receptors and all of these cytoprotective agents have mechanisms of action that are distinct from the presumed cytoprotective mechanisms of action of PACAP-like peptides. Therefore, one or more of these cytoprotective agents can have additive or even synergistic effects when administered in combination with PACAP-like peptides.

Synthesis of the Novel PACAP Analogs

Peptides were prepared by modified solid-phase procedures using Fmoc chemistries on a CEM microwave-assisted automatic peptide synthesizer (Matthews, N.C.) followed by trifluoroacetic acid (TFA) resin cleavage. Briefly, a standard Rink amide resin (Advanced CheTech, Louisville, Ky.) was used to yield peptide amides directly after TFA cleavage. Treatment with 20% piperidine in a dimethylformamide solution containing 0.2 M 1-hydroxybenzotriazole (HOBt) acid (2 minutes at 70° C.) was used for Fmoc group removal and amino acid couplings were achieved using a 4 M excess of each protected amino acid and 1 equivalent of the PyClocK reagent (Peptides International, Louisville, Ky.) and 2 equivalents of 0.2 M diisoprpropyethyamine in a dimethylformamide solution at 70° C. accompanied by microwave irradiation except for Fmoc-His(Trt), which was coupled at 50° C. for 15 minutes. Fmoc amino acid side-chain protection groups commonly used were: Asp, Glu, Ser, Thr, and Tyr: tBu; Arg: Pbf; Lys, Orn, Dab, and Dap: Boc; and His: Trt.

Peptides are simultaneously deprotected and cleaved from the resin support by shaking at room temperature for 4 hours with a mixture of TFA containing 1% water and 1% triisopropylsilane. The resin and solution were then poured into a large excess of cold diethylether and the precipitate and resin filtered through a fine glass frit. After washing with ether and allowing the precipitate and resin to dry, the cleaved peptide was extracted from the resin using dilute acetic acid/water mixtures. The resulting solutions were applied directly to preparative chromatography systems (either I.5 or 2.5×25 cm columns) containing Vydac C-I8 silica of 300-angstrom pore size (particle size m). Two fully volatile solvent elution systems have been used successfully for all of these peptides: linear gradients of acetonitrile in 0.1 % TFA or acetonitrile in 20% acetic acid (which was excellent for insoluble peptides) at flow rates of about 8-20 ml/min. Fractions containing the desired peptide in acceptable purity (>95%) were identified using analytical high-performance liquid chromatography (HPLC) and MALDI MS and then lyophilized.

A long-chain saturated fatty acid could be covalently linked to the free epsilon-amino group of one of the four Lys residues near the C-terminus of PACAP38, to one of the four Lys residues near the C-terminus of [Pip$^3$]PACAP38 (SEQ ID NO:12) or N-acetyl[Pip$^3$]PACAP38 (SEQ ID NO:13), to one of the five Lys residues near the C-terminus of one of the other five novel PACAP38 analogs (SEQ ID NOs:4-NO:8), or to PACAP38 analogs containing similar free amino group-containing amino acids such as Orn, Dab and Dap near the C-terminus. PACAP27 and PACAP38 have similar affinities for the PAC$_1$, VPAC$_1$ and VPAC$_2$ receptors suggesting that the additional 11 amino acids are not essential for high-affinity receptor binding. The fatty acid attachment will promote high-affinity binding of the conjugate to serum albumin (Kurtzhals et al., *J Pharm Sci* 85:304-308, 1996), which is by far the most abundant protein in serum, and dramatically reduce the rate of filtration by the kidney. This strategy has been used to make long-acting analogs of GLP-1 (Knudsen et al., *J Med Chem* 43:1664-1669, 2000), which is a member of the secretin/VIP/PACAP family.

The purity of each purified compound was confirmed by analytical HPLC and MALDI MS.

Therapeutic or Anticancer Agents Administered with or Coupled to PACAP Compounds of the Invention The PACAP analogs of the invention (e.g., PACAP-like compounds having the structure of Forumla (I); e.g., PACAP-like compounds having the sequence of SEQ ID NOs: 4-13) can be administered or formulated with, or coupled to, a therapeutic or anticancer agent. Examples of therapeutic and anticancer agents include, e.g., antineoplastic agents such as: Acivicin; Aclarubicin; Acodazole Hydrochloride; Acronine; Adozelesin; Adriamycin; Aldesleukin; Altretamine; Ambomycin; A. metantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Camptothecin; Caracemide;

Carbetimer; Carboplatin; Carmustine; Carubicin Hydrochloride; Carzelesin; Cedefingol; Chlorambucil; Cirolemycin; Cisplatin; Cladribine; Combretestatin A-4; Crisnatol Mesylate; Cyclophosphamide; Cytarabine; Dacarbazine; DACA (N- [2- (Dimethyl-amino) ethyl] acridine-4-carboxamide); Dactinomycin; Daunorubicin Hydrochloride; Daunomycin; Decitabine; Dexormaplatin; Dezaguanine; Dezaguanine Mesylate; Diaziquone; Docetaxel; Dolasatins; Doxorubicin; Doxorubicin Hydrochloride; Droloxifene; Droloxifene Citrate; Dromostanolone Propionate; Duazomycin; Edatrexate; Eflornithine Hydrochloride; Ellipticine; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; Gemcitabine; Gemcitabine Hydrochloride; Gold Au 198; Homocamptothecin; Hydroxyurea; Idarubicin Hydrochloride; Ifosfamide; Ilmofosine; Interferon Alfa-2a; Interferon Alfa-2b; Interferon Alfa-nl; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometerxol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin;Ormaplatin; Oxisuran; Paclitaxel; Pegaspargase; Peliomycin; Pentamustine; PeploycinSulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Rhizoxin; Rhizoxin D; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP53; Topotecan Hydrochloride; Toremifene Citrate; Trestolone Acetate; Triciribine Phosphate; Trimeterxate; Trimeterxate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2' Deoxyformycin; 9-am inocamptothecin; raltitrexed; N-propargyl-5,8-dideazafolic acid; 2chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan, chlorambucil; ifosfamide; busulfan; N-methyl-Nnitrosourea (MNU); N, N'-Bis (2-chloroethyl)-N -nitrosourea (BCNU); N- (2-chloroethyl)-N' cyclohexyl-N-nitrosourea (CCNU); N- (2-chloroethyl)-N'- (trans-4-methylcyclohexyl-N-nitrosourea (MeCCNU); N- (2-chloroethyl)-N'- (diethyl) ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin;Cl-973; DWA 2114R; JM216; JM335; Bis (platinum); azacitidine; cytarabine; gemcitabine; 6-Mercaptopurine; 6-Thioguanine; Hypoxanthine; teniposide 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxyretro-retinol; all-trans retinoic acid; N- (4- Hydroxyphenyl) retinamide; 13-cis retinoic acid; 3-Methyl TTNEB; 9-cis retinoic acid; fludarabine (2-F-ara-AMP); or 2-chlorodeoxyadenosine (2-Cda). Preferred anticancer agents for administration or formulation with, or coupling to, e.g., PACAP-like compounds having the structure of Forumla (I) (e.g., PACAP-like compounds having the sequence of SEQ ID NOs: 4-13) include cisplatin, carboplatin, oxaliplatin, bleomycin, mitomycin C, calicheamicins, maytansinoids, geldanamycin, doxorubicin, idarubicin, daunorubicin, epirubicin, busulfan, carmustine (BCNU), lomustine (CCNU), semustine, thalidomide, lenalidomide, methotrexate, azathioprine, 6-mercaptopurine, fludarabine, 5-azacytidine, pentostatin (2'-deoxycoformycin), cytarabine (cytosine arabinoside), gemcitabine, 5-fluorouracil, hydroxyurea, elesclomol (STA-4783), etoposide, teniposide, amsacrine, camptothecin, topotecan, irinotecan, chlorambucil, cyclophosphamide, ifosfamide, melphalan, bortezomib, vincristine, vinblastine, vinorelbine, paclitaxel, and docetaxel.

Other anti-neoplastic compounds that can be administered or formulated with, or coupled to, PACAP-like compounds of the invention (e.g., PACAP-like compounds having the structure of Formula (I); e.g., PACAP-like compounds having the sequence of SEQ ID NOs: 4-13) can be administered or formulated with, or coupled to, include, but are not limited to, 20-pi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e.g., 10-hydroxycamptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; epristeride; estramustine analogue; estrogen agonists; estrogen antagonists; etanidazole; elesclomol; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7;

lobaplatin; lombricine; lometerxol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; rnerbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimeterxate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

PACAP-like compounds of the invention can also be administered or formulated with, or coupled to, an antiproliferative agent, for example piritrexim isothionate, an antiprostatic hypertrophy agent, such as, for example, sitogluside, a benign prostatic hyperplasia therapy agent, such as, for example, tamsulosin hydrochloride, or a prostate growth inhibitor such as, for example, pentomone.

PACAP-like compounds of the invention can also be administered or formulated with, or coupled to, a radioactive agent, including, but not limited to: Fibrinogen $^{125}$I; Fludeoxyglucose $^{18}$F; Fluorodopa $^{18}$F; Insulin $^{125}$I; Insulin $^{131}$I; Iobenguane $^{123}$I; Iodipamide Sodium $^{131}$I; Iodoantipyrine $^{131}$I; Iodocholesterol $^{131}$I; Iodohippurate Sodium $^{123}$I; Iodohippurate Sodium $^{125}$I; Iodohippurate Sodium $^{131}$I; Iodopyracet $^{125}$I; Iodopyracet $^{131}$I; Iofetamine Hydrochloride $^{123}$I; Iomethin $^{125}$I; Iomethin $^{131}$I; Iothalamate Sodium $^{125}$I; Iothalamate Sodium $^{131}$I; tyrosine $^{131}$I; Liothyronine $^{125}$I; Liothyronine $^{131}$I; Merisoprol Acetate $^{197}$Hg; Merisoprol Acetate $^{203}$Hg; Merisoprol $^{197}$Hg; Selenomethionine $^{75}$Se; Technetium $^{99m}$Tc Antimony Trisulfide Colloid; Technetium $^{99m}$Tc Bicisate; Technetium $^{99m}$Tc Disofenin; Technetium $^{99m}$Tc Etidronate; Technetium $^{99m}$Tc Exametazime; Technetium $^{99m}$Tc Furifosmin; Technetium $^{99m}$Tc Gluceptate; Technetium $^{99m}$Tc Lidofenin; Technetium $^{99m}$Tc Mebrofenin; Technetium $^{99m}$Tc Medronate; Technetium $^{99m}$Tc Medronate Disodium; Technetium $^{99m}$Tc Mertiatide; Technetium $^{99m}$Tc Oxidronate; Technetium $^{99m}$Tc Pentetate; Technetium $^{99m}$Tc Pentetate Calcium Trisodium; Technetium $^{99m}$Tc Sestamibi; Technetium $^{99m}$Tc Siboroxime; Technetium $^{99m}$Tc; Succimer; Technetium $^{99m}$Tc Sulfur Colloid; Technetium $^{99m}$Tc Teboroxime; Technetium $^{99m}$Tc Tetrofosmin; Technetium $^{99m}$Tc Tiatide; Thyroxine $^{125}$I; Thyroxine $^{131}$I; Tolpovidone $^{131}$I; Triolein $^{125}$I; or Triolein $^{131}$I.

PACAP-like compounds of the invention can also be administered or formulated with, or coupled to, anti-cancer Supplementary Potentiating Agents, including, but not limited to: Tricyclic anti-depressant drugs (e.g., imipramine, desipramine, amitryptyline, clomipramine, trimipramine, doxepin, nortriptyline, protriptyline, amoxapine, and maprotiline); non-tricyclic anti-depressant drugs (e.g., sertraline, trazodone, and citalopram); Ca++ antagonists (e.g., verapamil, nifedipine, nitrendipine, and caroverine); Calmodulin inhibitors (e.g., prenylamine, trifluoroperazine, and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

PACAP-like compounds of the invention that are coupled to a therapeutic or cytoxic agent can also be administered or formulated with anti-cancer cocktails. Preferred anticancer agents used in anti-cancer cocktails include (some with their MTDs shown in parentheses): gemcitabine (1000 mg/m$^2$); methotrexate (15gm/m$^2$ i.v. +leuco. <500 mg/m$^2$ i.v. w/o leuco); 5fluorouracil (500 mg/m$^2$/day x 5days); floxuridine (100 mg/kg x 5 in mice, 0.6 mg/kg/day in human i.a.); FdUMP; Hydroxyurea (35 mg/kg/d in man); Docetaxel (60-100 mg/m$^2$); discodermolide; epothilones; vincristine (1.4mg/m$^2$); vinblastine (escalating: 3.3-11.1 mg/m$^2$, or rarely to 18.5 mg/m$^2$); vinorelbine (30 mg/m$^2$/wk); meta-pac; irinotecan (50-150 mg/m$^2$,1 x/wk depending on patient response); SN-38 (-100 times more potent than Irinotecan); 10-OH camptothecin; topotecan (1.5 mg/m$^2$/day in humans, 1 x iv LDIOmice=75 mg/m²); etoposide (100 mg/m² in man); adriamycin; flavopiridol; cisplatin (100mg/m² in man); carbo Pt carboplatin (360 mg/m² in man); bleomycin (20 mg/m2); mitomycin C (20 mg/m²); mithramycin (30 ug/kg); capecitabine (2.5 g/m² orally); cytarabine (100 mg/m²/day); 2-CI-2'deoxyadenosine; Fludarabine-PO4 (25 mg/m²/day, x 5days); mitoxantrone (12-14 mg/m²); mitozolomide (>400 mg/m²); Pentostatin; or Tomudex.

PACAP-like compounds of the invention can also be administered or formulated with, or coupled to a cytokine (e.g., granulocyte colony stimulating factor). Alternatively, PACAP-like compounds of the invention can be administered or formulated with, or coupled to, one or more immunomodulatory molecules, such as a molecule selected from the group consisting of antibodies, cytokines (e.g., interleukins, interferons, tumor necrosis factor (TNF), granulocyte macrophage colony stimulating factor (GM-CSF), macrophage colony stimulating factor (M-CSF), and granulocyte colony stimulating factor (G-CSF)), chemokines, complement components, complement component receptors, immune system accessory molecules, adhesion molecules, and adhesion molecule receptors.

PACAP-like compounds of the invention can also be administered or formulated with, or coupled to, an antimetabolic agent or a member of the anthracycline family of neoplastic agents. Antimetabolic agents include, but are not limited to, the following compounds and their derivatives: azathioprine, cladribine, cytarabine, dacarbazine, fludarabine phosphate, fluorouracil, gencitabine chlorhydrate, mercaptopurine, methotrexate, mitobronitol, mitotane, proguanil chlorohydrate, pyrimethamine, raltitrexed, trimeterxate glucuronate, urethane, vinblastine sulfate, vincristine sulfate, etc. More preferably, the antimetabolic agent is a folic acid-type antimetabolite, e.g., a class of agents that includes, for example, methotrexate, proguanil chlorhydrate, pyrimethanime, trimethoprime, or trimeterxate glucuronate, or derivatives of these compounds. Agents within the anthracycline family of neoplastic agents include, but are not limited to, aclarubicine chlorhydrate, daunorubicine chlorhydrate, doxorubicine chlorhydrate, epirubicine chlorhydrate, idarubicine chlorhydrate, pirarubicine, or zorubicine chlorhydrate; a camptothecin, or its derivatives or related compounds, such as 10, 11 methylenedioxycamptothecin; or a member of the maytansinoid family of compounds, which includes a variety of structurally related compounds, e.g., ansamitocin P3, maytansine, 2'-N-demethylmaytanbutine, and maytanbicyclinol.

The PACAP-like compounds of the invention can be coupled directly to a therapeutic or anticancer agent using known chemical methods. Alternatively the PACAP-like compounds can be coupled to an anticancer or therapeutic agent via an indirect linkage. For example, the PACAP-like compounds may be attached to a chelating group that is attached to the anticancer or therapeutic agent. Chelating groups include, but are not limited to, iminocarboxylic and polyaminopolycarboxylic reactive groups, diethylenetri-aminepentaacetic acid (DTPA), and 1,4,7,10-tetraazacyclododecane-1,4,7,10-tetraacetic acid (DOTA). For general methods, see, e.g., Liu et al., *Bioconjugate Chem.* 12(4):653, 2001; Cheng et al., WO 89/12631; Kieffer et al., WO 93/12112; Albert et al., U.S. Pat. No. 5,753,627; and WO 91/01144 (each of which are hereby incorporated by reference). When coupled to a therapeutic or anticancer agent, the specific targeting by the PACAP-like compounds of the invention allows selective destruction of cells expressing a PACAP/VIP receptor, including, e.g., the catecholamine-containing cells in the adrenal medulla and the sympathetic ganglia; microglia, astrocytes and some types of neurons in the central nervous system; and T- and B-lymphocytes, macrophages, neutrophils, dendritic cells in the immune system, and cancer cells (e.g., leukemia, lymphoma, and myeloid cancer cells; in particular granuloma cells). PACAP-like compounds of the invention may be administered to a mammalian subject, such as a human, directly or in combination with any pharmaceutically acceptable carrier, excipient, or salt known in the art, as is discussed in more detail herein.

Diagnostic Agents Coupled to PACAP-Like Compounds of the Invention

PACAP-like compounds of the invention can be modified or labeled to facilitate diagnostic or therapeutic uses. Detectable labels, such as a radioactive, fluorescent, heavy metal, or other agent may be bound (ionically or covalently) to the PACAP-like compounds of the invention. Single, dual, or multiple labeling of a PACAP-like compound of the invention may be advantageous. For example, dual labeling with radioactive iodination of one or more residues combined with the additional coupling of, for example, $^{90}$Y via a chelating group to amine-containing side or reactive groups, would allow combination labeling. This may be useful for specialized diagnostic needs, such as identification of widely dispersed small neoplastic cell masses. PACAP-like compounds of the invention may also be modified, for example, by halogenation. Halogens include fluorine, chlorine, bromine, iodine, and astatine. Such halogenated compounds may be detectably labeled, e.g., if the halogen is a radioisotope, such as, for example, $^{18}$F, $^{75}$Br, $^{77}$Br, $^{122}$I, $^{123}$I, $^{124}$I, $^{125}$I, $^{129}$I, $^{131}$I, or $^{211}$At. Other suitable detectable modifications include binding of other compounds (e.g., a fluorochrome, such as fluorescein) to the PACAP-like compounds of the invention.

Radioisotopes for radiolabeling the PACAP-like compounds of the invention can be selected from radioisotopes that emit either beta or gamma radiation. Alternatively, PACAP-like compounds of the invention can be modified to contain a chelating group. The chelating group can then be modified to contain any of a variety of radioisotopes, such as gallium, indium, technetium, ytterbium, rhenium, or thallium (e.g., $^{125}$I, $^{67}$Ga, $^{111}$In, $^{99m}$Tc, $^{169}$Yb, $^{186}$Re). PACAP-like compounds of the invention that include radioactive metals are useful in radiographic imaging or radiotherapy. Preferred radioisotopes also include $^{99m}$Tc, $^{51}$Cr, $^{67}$Ga, $^{68}$Ga, $^{111}$In, $^{168}$Yb, $^{140}$La, $^{90}$Y, $^{88}$Y, $^{153}$Sm, $^{156}$Ho, $^{165}$Dy, $^{64}$Cu, $^{97}$Ru, $^{103}$Ru, $^{186}$Re, $^{188}$Re, $^{203}$Pb, $^{211}$Bi, $^{212}$Bi, $^{213}$Bi, and $^{214}$Bi. The choice of metal is determined based on the desired therapeutic or diagnostic application. PACAP-like compounds of the invention that include a metal component are useful as diagnostic and/or therapeutic agents. A detectable label may be a metal ion from heavy elements or rare earth ions, such as $Gd^{3+}$, $Fe^{3+}$, $Mn^{3+}$, or $Cr^{2+}$. Conjugates that include paramagnetic or superparamagnetic metals are useful as diagnostic agents in MRI imaging applications. Paramagnetic metals that may be used in conjunction with PACAP-like compounds of the invention include, but are not limited to, chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), and ytterbium (III). Preferably, the PACAP-like compounds have a relaxtivity of at least 10, 12, 15, or 20 $mM^{-1}sec^{-1}Z^{-1}$, wherein Z is the concentration of paramagnetic metal.

PACAP-like compounds of the invention can be coupled to a chelating agent to form diagnostic conjugate of the invention. Chelating groups may be used to indirectly couple detectable labels or other molecules to PACAP-like compounds of the invention. Chelating groups may be used to link radiolabels to the PACAP-like compounds of the invention. Examples of chelators known in the art include, for example, the iminocarboxylic and polyaminopolycarboxylic reactive groups, ininocarboxylic and polyaminopolycarboxylic reactive groups, diethylenetriaminepentaacetic acid (DTPA), and 1,4,7,10-tetraazacyclododecane-1,4,7,10-tetraacetic acid (DOTA). Diagnostic conjugates may be prepared by various methods depending upon the chelator chosen. The PACAP-like compound portion of the conjugate can be prepared by techniques known in the art, and by techniques described herein.

Demonstration of the Therapeutic Usefulness

The protocols and compositions of the present invention are preferably tested in vitro, and then in preclinical models in vivo, for the desired therapeutic or prophylactic activity, prior to use in humans. For example, in vitro assays that can be used to determine whether administration of a specific therapeutic protocol is indicated include in vitro cell culture assays in which an appropriate cell line or a patient's tissue sample is grown in culture, and exposed to or otherwise administered a protocol, and the effect of such protocol upon the tissue sample is observed. For example (but not by way of limitation), rescuing of sensory neurons, renal or pulmonary epithelial cells, hepatocytes, or cardiomyocytes; decreased NFκB activation; decreased survival or proliferation of B- or T-lymphocytes; or decreased production of TNF-α and IL-6. A demonstration of one or more of the aforementioned properties of the exposed cells indicates that the therapeutic agent is effective for treating the condition in the patient. Many assays standard in the art can be used to assess such survival and/or growth of neurons, epithelial cells, hepatocytes, and/or B- or T-lymphocytes. Furthermore, any of the assays known to those skilled in the art can be used to evaluate the prophylactic and/or therapeutic utility of the therapies disclosed herein for treatment, management or prevention of injuries to one or more major organs of the body caused by trauma, diseases or other prophylactic or therapeutic agents.

The injuries to one or more major organs of the body of humans or other mammals caused by trauma, acute or chronic diseases, or one or more prophylactic/therapeutic agents (e.g., one or more anticancer agents) can be monitored in the subjects with commonly used biomarkers. For example (but not by way of limitation), injury to the kidney can be monitored by determining the concentration of protein in the urine, or the concentration of creatinine or urea nitrogen in the bloodstream. Injury to the liver can be monitored by determining the enzyme activity or concentration of alanine aminotransferase in the bloodstream, or the concentration of conjugated bilirubin in the urine. Injury to the heart can be monitored by determining the concentration of troponin I or the MB isoenzyme of creatinine kinase in the bloodstream. Injury to the β-cells of the pancreas can be monitored by determining the activity or concentration of glutamic acid decarboxylase in the bloodstream, and injury to the nervous system can be monitored by determining the activity or concentration of neuron-specific enolase in the bloodstream.

The injuries to one or more major organs of the body of humans or other mammals caused by trauma, acute or chronic diseases, or one or more prophylactic/therapeutic agents (e.g., one or more anticancer agents) can also be monitored in the subjects with commonly used imaging techniques. For example (but not by way of limitation), injury to the heart can be monitored by electrocardiography or serial echocardiography.

The injuries to one or more major organs of the body of humans or other mammals caused by trauma, acute or chronic diseases, or one or more prophylactic/therapeutic agents (e.g., one or more anticancer agents) can also be monitored in the subjects with commonly used functional tests. For example (but not by way of limitation), injury to the kidney can be monitored by determining the glomerular filtration rate with cystatin C or with sodium $^{125}$I-iothalamate clearance. Injury to the peripheral nerves can be monitored by determining nerve conduction velocities or somatosensory perception. Injury to the heart can be monitored with a variety of exercise tests.

Based on the currently available data, there is a correlation between the reduction in the rate of proliferation of some cancer cells by PACAP-like compounds and the enhancement of the therapeutic efficacy of anticancer agents by PACAP-like compounds. Cancer cells can be obtained from biopsy samples from humans and other mammals, cultured in multi-well plates, and the effect of PACAP-like peptides on their rate of proliferation can be quantified in order to determine whether the PACAP-like compounds will protect the cancer cells against cancer chemotherapeutics or enhance the efficacy of cancer chemotherapeutics.

The definitive diagnosis of multiple myeloma can be made in about 95% of the patients after a bone marrow aspiration or bone marrow biopsy. In the other patients, the bone marrow involvement is probably focal rather than diffuse. The efficacy of the adjunctive treatment with PACAP-like peptides can be determined subjectively by the patient reporting an improvement in symptoms, such as bone pain, fatigue, and overall well-being. The efficacy of the adjunctive treatment with PACAP-like peptides can be determined objectively by a physical examination that shows an improvement in overall appearance and muscle strength, by laboratory tests that show a reduction in anemia (a rise in hemoglobin and hematocrit), serum and urinary levels of the monoclonal paraprotein (Bence-Jones protein), and serum and urinary β-2 microglobulin, and by laboratory tests that show an improvement in kidney function (blood creatinine, urea nitrogen and cystatin C). In a preferred embodiment, serum and urinary levels of the monoclonal free light-chain immunoglobulin (Bence-Jones protein) are monitored with a highly sensitive nephelometric assay during the course of the treatment with the PACAP-like cytoprotective adjunctive agents.

Those skilled in the art will recognize, or be able to ascertain using no more than routine searches of the medical literature that there are similar standard methods for selecting appropriate patient populations to study of the effects of the compositions of the present invention on age-related neurodegenerative diseases; injuries to the central nervous system caused by stroke, heart attack and blunt force trauma; Huntington's disease and other CAG codon repeat expansion diseases; retinal diseases; autoimmune diseases; keratoconjunctivitis sicca; type II diabetes; sepsis; acute and chronic cardiovascular diseases; acute and chronic renal diseases; acute and chronic pulmonary diseases; systemic hypertension; hematological cancers; eating disorders; acute and chronic liver diseases; osteoporosis; pre-eclampsia; cell and solid organ transplantation; cognitive disorders; AIDS dementia complex; and aging of the central nervous system.

Pharmaceutical Compositions

The compositions of the present invention include bulk drug compositions useful in the manufacture of pharmaceutical compositions (e.g., impure or non-sterile compositions) and parenteral pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the present invention comprise a prophylactically or therapeutically effective amount of one or more PACAP-like compounds useful in the method of the invention and a pharmaceutically acceptable carrier. In a further embodiment, the composition of the present invention further comprises an additional therapeutic as discussed above.

In a specific embodiment, the term "pharmaceutically acceptable" means approved by a regulatory agency of the Federal government or listed in the U.S. Pharmacopeia or other generally recognized pharmacopeia for use in animals, and particularly for use in humans. The term "carrier" refers to a diluent, adjuvant (e.g., Freund's adjuvant or, more preferably, MF59C.I adjuvant), excipient, or vehicle with which the therapeutic is administered. The pharmaceutical carriers can be sterile liquids, such as water and oils, including those of petroleum, animal, vegetable or synthetic origin, such as peanut oil, soybean oil, mineral oil, sesame oil. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include (but are not limited to) starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The composition, if desired, can also contain minor amounts of wetting or emulsifying agents, or pH buffering agents. These compositions can take many forms, including (but not limited to) suspensions, emulsions, tablets, pills, capsules, powders, and sustained-release formulations.

Generally, the ingredients of the compositions of the present invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the present invention can be formulated as neutral or salt forms. Pharmaceutically acceptable salts include (but are not limited to) those formed with anions such as those derived from hydrochloric acid, phosphoric acid, acetic acid, oxalic acid, and tartaric acid, and those formed with cations such as those derived from sodium, potassium, ammonium, calcium, ferric hydroxides, isopropylamine, triethylamine, 2-ethylamino ethanol, histidine, and procaine.

As desired, additives such as a dissolution aid (e.g., sodium salicylate or sodium acetate), a buffer (e.g., sodium citrate or glycerin), an isotonizing agent (e.g., glucose or invert sugar), a stabilizer (e.g., human serum albumin or polyethylene glycol), a preservative (e.g., benzyl alcohol or phenol), or an analgesic (e.g., benzalkonium chloride or procaine hydrochloride) may be added.

There are many delivery methods known to those skilled in the art that can be used to administer the PACAP-like compound(s), or the PACAP-like compound(s) in combination with other cytoprotective agents, in order to treat, manage or prevent injuries to one or more of the major organs of the body of humans or other mammals caused by one or more anticancer agents. For example (but not by way of limitation), encapsulation in liposomes, microparticles or microcapsules, secretion from mammalian cells genetically engineered to synthesize one or more PACAP-like peptides, or synthesis by various recombinant viral vectors. The routes of administration of the PACAP-like compounds of the present invention include (but are not limited to), parenteral (e.g., intradermal, intramuscular, intraperitoneal, intravenous, and subcutaneous), vaginal, rectal, epidural, and mucosal (e.g., intranasal, inhaled, and oral routes). In a specific embodiment, prophylactic or therapeutic agents of the present invention are administered intramuscularly, intravenously, intraosseously, or subcutaneously. The prophylactic or therapeutic agents may be administered by any convenient route or regimen, for example by infusion or a bolus injection, by absorption through epithelial or mucocutaneous linings (e.g., oral mucosa, rectal, topical, including buccal and sublingual, and intestinal mucosa, etc.) and may be administered in combination with other biologically active agents. Administration can be systemic or local.

In a specific embodiment, it may be desirable to administer the prophylactic or therapeutic agents of the present invention locally to the area in need of treatment; this maybe achieved by, for example, but not by way of limitation, local infusion, by injection, or by means of an implant, said implant being of a porous, non-porous, or gelatinous material, including membranes, such as Silastic membranes, or fibers.

In another embodiment, the compositions of this invention can be delivered in a controlled release or sustained release manner. In one embodiment, a pump can be used to achieve controlled or sustained release. In another embodiment, polymeric materials can be used to achieve controlled release or sustained release. Suitable polymers for controlled release or sustained release formulations include (but are not limited to) poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly (lactide-co-glycolides) (PLGA), and polyorthoesters. In a preferred embodiment, the polymer used in a controlled release or a sustained release formulation is inert, free of leachable impurities, stable on storage, sterile, and biodegradable. In a specific embodiment, a controlled release, or a sustained release device or formulation can be placed in proximity of the prophylactic or therapeutic target, thus reducing the required amount of the PACAP-like compound to only a fraction of the systemic dose. Many other techniques known to one skilled in the art can be used to produce controlled release or sustained release formulations comprising one or more therapeutic agents of the present invention.

The compositions for administration of the PACAP-like compounds include (but are not limited to) those suitable for oral, rectal, nasal, topical (including buccal and sublingual), vaginal, or parenteral (including subcutaneous, transcutaneous, intramuscular, intravenous, and intradermal) administration. The formulations may conveniently be presented in unit dosage forms and may be prepared by any methods well known in the art of pharmacy. Thus, the PACAP-like compounds of the present invention and their physiologically acceptable salts and solvates may be formulated for administration by inhalation or insufflation (either through the mouth or the nose), or by oral, parenteral or mucosal (such as buccal, vaginal, rectal, and sublingual) routes. In a preferred embodiment, parenteral administration is used.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium dodecyl sulfate). The tablets may be coated by methods well known in the art. Liquid preparations for oral administration may take the form of, for example, solutions, syrups or suspensions, or they may be presented as a dry product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated to give controlled release or sustained release of the active compound.

For buccal administration, the compositions of the present invention may be conventionally formulated as tablets or lozenges.

For administration by inhalation, the prophylactic or therapeutic agents for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The prophylactic or therapeutic agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in a powder form for reconstitution before use with a suitable vehicle, e.g., sterile pyrogen-free water.

In addition to the formulations described previously, the prophylactic or therapeutic agents may also be formulated as a depot preparation. Such long-acting formulations may be administered by implantation (e.g., subcutaneously or intramuscularly) or by intramuscular injection. Thus, for example, the prophylactic or therapeutic agents may be formulated with suitable polymeric or hydrophobic materials (e.g., as an emulsion in an acceptable oil) or ion-exchange resins, or as sparingly soluble derivatives, for example, as a sparingly soluble salt.

Compositions suitable for topical administration to the skin may be presented as ointments, creams, gels, and pastes comprising the compound and a pharmaceutically acceptable carrier. For example (but not by way of limitation), a suitable topical delivery system is a transdermal patch containing the PACAP-like compound to be administered.

Sublingual tablets can be prepared by using binders (e.g., hydroxypropylcellulose, hydroxypropylmethylcellulose, or polyethylene glycol), disintegrating agents (e.g., starch or carboxymethylcellulose calcium), and/or lubricants (e.g., magnesium stearate or talc).

Suitable formulations for nasal administration wherein the carrier is a solid include a coarse powder having a particle size, for example, in the range to 500 microns (m). Suitable formulations for nasal administration wherein the carrier is a liquid (e.g., a nasal spray or nasal drops) include aqueous or oily solutions of the active ingredient.

Compositions suitable for parenteral administration include aqueous and non-aqueous sterile injection solutions which may contain anti-oxidants, buffers, bacteriostatic agents, and solutes that make the formulation isotonic with the blood of the intended recipient; and aqueous and non-aqueous sterile suspensions that may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described. It should be understood that in addition to the ingredients specifically mentioned above, the formulations of this invention may include other agents commonly used in the art for the type of formulation in question. For example (but not by way of limitation), those suitable for oral administration may include flavoring agents.

EXAMPLES

In order to make the uses of the present invention clearer, the following examples are presented. These examples are only for illustrative purposes and should not be interpreted in any way as limitations in the uses of this invention.

Example 1

Novel PACAP Analogs

Peptides can have extraordinarily high affinities for their cognate receptors. The major drawback of using native peptides as therapeutics is their short half-life in the circulation after parenteral administration due mainly to rapid proteolysis and rapid filtration by the kidney. Therefore, analogs of PACAP have been made in order to reduce the rates of proteolysis and/or renal clearance. In addition, other changes have been made in the native amino-acid sequences of PACAP27 and PACAP38 in order to reduce the cost of synthesis, and alter tissue distribution and/or receptor specificity.

Ten novel peptide analogs of PACAP27 or PACAP38 have been made by solid-phase synthesis (SEQ ID NOs: 4-13; FIG. 1 and FIG. 2) using the procedures briefly described above.

Some of the biological properties of nine of these ten PACAP analogs are illustrated below (FIGS. 3-10) and the potential medical applications of these novel PACAP analogs suggested by these illustrations are briefly outlined.

Example 2

Inhibition of the Proliferation of Multiple Myeloma Cells by PACAP38, PACAP27, VIP, and Novel PACAP Analogs Multiple myeloma, a malignant cancer of plasma cells, is the sixth most common cancer in the USA. It accounts for about 10% of the hematological malignancies diagnosed in the USA. Multiple myeloma is slightly more prevalent in men than in women. The disease can cause serious medical complications, including bone resorption (osteolysis), hypercalcemia, anemia, thrombocytopenia, and kidney failure. Inflammation of the kidney is the second most frequent complication and occurs in about half of the patients with multiple myeloma. The cause of this inflammation is the overproduction by plasma cells of light-chain immunoglobulins (Bence-Jones proteins), which aggregate to form casts in the distal convoluted tubules and collecting ducts of the kidneys. Plasma cells are derived from activated B lymphocytes by clonal expansion. The normal restraints on the expansion of a single plasma cell clone is lost in patients with multiple myeloma, which results in the excessive production of a single type of light-chain immunoglobulin.

The effects of PACAP38, PACAP27, VIP, and PACAP analogs on myeloma cell proliferation were assessed by determining incorporation bromodeoxyuridine into DNA during cell division. The number of myeloma cells approximately doubled during the 24-hour incubation period in the absence of treatment with PACAP-like peptides. The addition of PACAP38 to the medium resulted in 50% inhibition of the rate of proliferation of the light-chain immunoglobulin-secreting human myeloma cells at a concentration of about 250 picomolar (FIG. 3). Four of the five novel PACAP38 analogs caused 50% inhibition of the rate of proliferation of the light-chain immunoglobulin-secreting human myeloma cells at concentrations substantially below 1 nanomolar (FIG. 3). PACAP27, VIP and the novel PACAP27 analogs were significantly less potent than either PACAP38 or the novel PACAP38 analogs in this in vitro model of hematopoietic cancer cell proliferation. These results suggest that inhibition of the proliferation of this human multiple myeloma cell line is mediated primarily by stimulation of the $PAC_1$ receptor and the phospholipase C-mediated signal transduction pathway (Spengler et al., Nature 365:170-175, 1993). PACAP38 analogs with either nipecotic acid or isonipecotic acid in position 3 were more than 10,000 times less potent as inhibitors of multiple myeloma cell proliferation than the corresponding analog with pipecolic acid in position 3 (FIG. 4).

PACAP and PACAP analogs have also been shown to inhibit the proliferation of myeloid hematopoietic cancer cells (Hayez et al., J Neuroimmunol 149:167-181, 2004) and to enhance the killing of both lymphoid and myeloid hematopoietic cancer cells by commonly used anticancer agents such as carmustine, vincristine and thalidomide (PCT/US2009/058445). PACAP38 can also directly protect the kidney against light-chain immunoglobulin overload and would be expected to inhibit bone resorption in patients with multiple myeloma (Li et al., Regul Pept 145:24-32, 2008). PACAP protects kidney, lung, pancreatic and neuronal epithelial cells against commonly used anticancer agents such as cisplatin, doxorubicin, bleomycin, and streptozotocin (Aubert et al., Neurobiol Dis 32:66-80, 2008; Onoue et al., FEBS J 275: 5542-5551, 2008; PCT/US2009/058445; FIG. 5). These results indicate that these novel PACAP38 analogs could be used as either monotherapeutics or adjunctive therapeutics for both lymphoid and myeloid hematopoietic cancers, especially multiple myeloma.

Example 3

Reduction of Cisplatin-Induced Cytotoxicity by PACAP38, PACAP27 and Novel PACAP Analogs Cisplatin (cis-diamminedichloridoplatinum(II), Platinol) is the first-in-class platinum-based DNA-crosslinking anti-cancer therapeutic. It was approved for clinical use by the U.S. FDA in 1978. The other members of this class of "alkylating-like" platinum-based anticancer agents now include (but are not limited to) carboplatin, oxaliplatin and satraplatin. Cisplatin is one of the most widely used cancer chemotherapeutics and is the cornerstone of many multi-drug anti-cancer regimens. Nephrotoxicity is usually the "dose-limiting" toxicity for the use of cisplatin in cancer chemotherapy, but sensory neuropathies can sometimes limit the doses that can be used to treat some patients.

Treatment of rat renal proximal tubule epithelial cells with cisplatin resulted in a large significant increase in apoptotic cell death (FIG. 5). The addition of PACAP38 to the medium at a concentration of $10^{-6}$ M resulted in a significant reduction in cisplatin-induced apoptotic cell death of these proximal tubule epithelial cells. VIP also reduced the cisplatin-induced apoptotic cell death of the human renal proximal tubule epithelial cells, but VIP was significantly less potent than PACAP38. The three novel PACAP38 analogs (SEQ ID NOs 4, 5 and 6) were either as effective or more effective than PACAP38 as cytoprotectants in this in vitro model of acute renal proximal tubule cell injury (FIG. 5).

These experiments show that PACAP38 and the three novel PACAP38 analogs are potent cytoprotectants against cisplatin-induced damage to the kidney, which is the "dose-limiting" toxicity for cancer chemotherapy with cisplatin. Therefore, pre- and/or post-treatment of subjects undergoing cisplatin-based cancer chemotherapy with therapeutic doses of these novel PACAP38 analogs should result in a higher maximal tolerable dose of cisplatin, and an increased frequency of partial clinical responses and/or an increased number of complete remissions. We have previously shown that PACAP38 protects the kidney against acute injury due to light-chain immunoglobulin overload, gentamicin, streptozotocin, and doxorubicin (Li et al., Regul Pept 145:24-32, 2008; Maderdrut et al., VIP, PACAP and Related Peptides [Ninth International Symposium], Kagoshima, 2009). Therefore, these novel PACAP38 analogs should also protect the kidney against a similarly broad range of potential nephrotoxins.

Example 4

Reduction of Ischemia/Reperfusion Injury by PACAP38 and Novel PACAP Analogs

Ischemia/reperfusion injury to one or more major organs of the body can be caused by blunt force trauma, transient arterial stenosis, hemorrhagic shock, severe sepsis, solid organ transplantation, and deliberately during some common surgical procedures.

Transient clamping of the renal artery for 45 minutes resulted in a large significant increase in serum creatinine after 72 hours. The administration of PACAP38, [$Pip^3$, $Ala^{15,17}$,$Aib^{16,28}$,$Lys^{34}$,$D-Lys^{38}$]PACAP38 (SEQ ID NO 5) or [$Pip^3$,$Ala^{14,17}$,$Aib^{16,28}$,$Lys^{34}$,$D-Lys^{38}$]PACAP38 (SEQ ID NO 6) almost completely reversed the rise in serum creatinine caused by ischemia/reperfusion (FIG. 6). Both novel PACAP38 analogs appear to be slightly more potent than native PACAP38 in this in vivo model.

These experiments show that PACAP38 and the two novel PACAP38 analogs are potent cytoprotectants against injury to the kidney caused by ischemia/reperfusion. PACAP-like peptides have already been shown to protect the brain, heart, lung, pancreas, and intestine against injury caused by ischemia/reperfusion. Therefore, these novel PACAP38 analogs should also protect a similarly broad range of major organs of the body of humans and other mammals against injuries caused by ischemia/reperfusion. These novel PACAP analogs should be useful therapeutics for injuries caused by blunt force trauma, transient arterial stenosis, hemorrhagic shock, severe sepsis, solid organ transplantation, and the side-effects of some common surgical procedures. These novel PACAP analogs could be used at one or more stages of the organ transplantation process: for perfusion of the brain-dead organ donor, as an additive in the organ storage solution or for treatment of the organ recipient after transplantation.

Example 5

Inhibition of Dexamethasone-Sensitive and Dexamethasone-Resistant B-Lymphocytes by PACAP38 and a Novel PACAP Analogs Glucocorticoids are frequently used for the treatment of patients with blood cancers and autoimmune diseases in order to inhibit the activity of B- and T-lymphocytes. However, a significant portion of the patients treated with glucocorticoids eventually become resistant to the steroid (Barnes & Adcock, *Lancet* 373:1905-1917, 2009).

FIGS. 8 and 9 shows the effects PACAP38, [Pip$^3$,Ala$^{1417}$, Aib$^{16,28}$,Lys$^{34}$,D-Lys$^{38}$]PACAP38 (SEQ ID NO: 6) and dexamethasone on the proliferation of two different light-chain immunoglobulin-secreting human myeloma cell lines that were derived from the same patient who was being treated for multiple myeloma with a dexamethasome-containing regimen (Greenstein et al., *Exp Hematol* 31:271-282, 2003). The cell line in FIG. 8 (MM.1S) appears to be as sensitive to dexamethasone as it is to PACAP38, while the cell line in FIG. 9 (MM.1R) is almost completely insensitive to dexamethasone but is still sensitive to both PACAP38 and the novel PACAP38 analog.

These observations indicate that PACAP-like peptides should be efficacious in patients with blood cancers and autoimmune diseases even after the patients have become resistant to glucocorticoids. Therefore, these novel PACAP analogs could be used to replace the glucocorticoid in common multiple drug regimens, such as COP (cyclophosphamide, ONCOVIN™ (vincristine) and prednisone) and VAD (vincristine, ADRIAMYCIN™ (doxorubicin) and dexamethasone), as soon as the patient becomes insensitive to the steroid. These observations also indicate that these novel PACAP analogs could be used as monotherapy to replace the commonly used glucocorticoid for diseases such as systemic lupus erythematosis and rheumatoid arthritis. In addition, these observations indicate that PACAP-like peptides could be efficacious in patients with inflammatory diseases that are usually insensitive to treatment with glucocorticoids such as cystic fibrosis and interstitial pulmonary fibrosis.

The above examples show that these novel PACAP analogs (SEQ ID NOs: 4-13) should be efficacious monotherapeutics and/or adjunctive therapeutics for an extraordinarily wide range of major medical disorders. The above examples show that these novel PACAP38 analogs could be used as either monotherapeutics and/or adjunctive therapeutics for both lymphoid and myeloid hematopoietic cancers, for acute and chronic drug-induced nephropathies, and for injuries caused by blunt force trauma, transient arterial stenosis, hemorrhagic shock, severe sepsis, solid organ transplantation, and the side-effects of some common surgical procedures. In addition, these novel PACAP analogs should be efficacious monotherapeutics and/or adjunctive therapeutics for the extraordinarily wide range of other major medical disorders already shown for native PACAP27, native PACAP38 and native VIP (see SUMMARY OF THE INVENTION).

Example 6

Reduction of Gentamicin-Induced Cytotoxicity by PACAP38 and a Novel PACAP Analog Aminoglycosides are commonly used as antibiotics for the treatment of Gram-negative bacterial infections. The use of aminoglycosides as antibacterial agents is limited by their nephrotoxic (Mingeot-Leclercq & Tulkens, *Antimicrob Agents Chemother* 43:1003-1012, 1999) and ototoxic (Selimoglu, *Curr Pharm Des* 13:119-126) side-effects. The proximal tubule epithelial cells of the kidney undergo apoptosis in animals and humans treated with gentamicin.

Treatment of human renal proximal tubule epithelial cells with gentamicin (FIG. 10) resulted in a large significant increase in apoptotic cell death. The addition of PACAP38 or [Pip$^3$]PACAP38 (SEQ ID NO 12) to the medium resulted in a significant dose-dependent reduction in gentamicin-induced apoptotic cell death of these proximal tubule epithelial cells. PACAP38 was more effective as a cytoprotectant in this in vitro model of aminoglycoside-induced renal proximal tubule epithelial cell injury than the novel PACAP38 analog (FIG. 10).

These observations indicate that PACAP-like peptides should be useful as adjunctive agents in combination with aminoglycosides for the treatment of bacterial infections, especially Gram-negative bacterial infections.

There are more than 1,000 human genetic diseases that are caused in part by premature in-frame stop codons that result in the synthesis of truncated nonfunctional proteins. Burke & Mogg (Nucleic Acids Res 13:6265-6272,1985) discovered that aminoglycosides could impair the recognition of premature stop codons in mammalian cells. Aminoglycosides have now been shown to impair the recognition of premature stop codons in vitro and/or in animal models in vivo for numerous genetic diseases, including cystic fibrosis, Duchenne muscular dystrophy, Hurler's syndrome, nephropathic cystinosis, polycystic kidney disease, retinitis pigmentosa, and ataxia telangiectasia. Gentamicin has been shown to promote the synthesis of small quantities of full-length functional proteins in human clinical trials for cystic fibrosis (Wilschanski et al., N Engl J Med 349:1433-1441, 2003) and Duchenne muscular dystrophy (Politano et al., Acta Myol 22:15-21, 2003). However, the use of aminoglycosides to impair recognition of premature stop codons and promote the synthesis of full-length functional proteins is limited by their nephrotoxic (Mingeot-Leclercq & Tulkens, Antimicrob Agents Chemother 43:1003-1012, 1999) and ototoxic (Selimoglu, Curr Pharm Des 13:119-126) side-effects. These side-effects should be extremely serious limitations for the treatment of life-long diseases. PACAP-like peptides should be useful as adjunctive agents in combination with aminoglycosides for the treatment of genetic diseases caused by in-frame premature stop codons because of their cytoprotective effects against aminoglycoside-induced renal proximal tubule epithelial cell injury. Cystic fibrosis is one of the most common genetic diseases among Caucasians. It is an autosomal recessive disease that is caused by mutations in both alleles of the gene for the cystic fibrosis transmembrane conductance regulator. Over 1,000 different mutations have been described in the cystic fibrosis transmembrane conductance regulator gene. About 10% of these mutations are in-frame premature stop codons. The combination of an aminoglycoside and a PACAP-like peptide should be especially efficacious in a significant portion of patients with cystic fibrosis because published articles indicate that PACAP should be modestly efficacious in some patients with cystic fibrosis even as a monotherapeutic. PACAP stimulates the activity of the cystic fibrosis transmembrane conductance regulator (Dérand et al., Br J Pharmacol 141:698-708, 2004) and would facilitate the insertion of the cystic fibrosis transmembrane conductance regulator into membranes (Ameen et al., J Cell Sci 12:887-894, 1999; Chappe et al., J Pharmacol Exp Ther 327:226-238, 2008). In addition, PACAP inhibits neutrophil infiltration into the lung (Kinhult et al., Peptides 22:2151-2154, 2001; Sergejeva et al., Regul Pept 117:149-154, 2004). Furthermore, lung inflammation in persons with cystic fibrosis is usually insensitive to corticosteroids (see above). The combination of an aminoglycoside and a PACAP-like peptide should also be especially efficacious in a significant portion of other recessive diseases where PACAP-like peptides would be expected to have modest efficacy as monotherapeutics, including (but not limited to) Duchenne muscular dystrophy, nephropathic cystinosis and polycystic kidney disease.

Equivalents

Those skilled in the art will recognize, or be able to ascertain using no more than routine experimentation, many equivalents to the specific embodiments of the present invention described herein. Such equivalents are intended to be encompassed by the following claims.

All publications, patents and patent applications mentioned in this specification are herein incorporated by reference into the specification to the same extent as if each individual publication, patent or patent application was specifically indicated to be incorporated herein by reference.

What is claimed is:

1. A compound having a sequence selected from any one of SEQ ID NOs: 4-13 or a pharmaceutically acceptable salt thereof.

2. A polypeptide having at least 90% sequence identity to a sequence selected from any one of SEQ ID NOs: 4-13, wherein the polypeptide comprises a pipecolic acid (Pip) residue at position 3.

3. The polypeptide of claim 2, wherein said polypeptide is conjugated to a radionuclide selected from the group consisting of $^{11}$C, $^{13}$N, $^{15}$O, $^{18}$F, $^{52}$Fe, $^{55}$Co, $^{61}$Cu, $^{62}$Cu, $^{64}$Cu, $^{67}$Cu, $^{67}$Ga, $^{68}$Ga, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{111}$In, $^{120}$I, $^{123}$I, $^{124}$I, $^{125}$I, $^{131}$I, $^{122}$Xe, $^{175}$Lu, $^{154}$Gd, $^{155}$Gd, $^{156}$Gd, $^{157}$Gd, $^{158}$Gd, $^{94m}$TC, $^{94}$Tc, and $^{99m}$Tc.

4. The polypeptide of claim 2, wherein said polypeptide is conjugated to cisplatin, carboplatin, oxaliplatin, bleomycin, mitomycin C, calicheamicins, maytansinoids, geldanamycin, doxorubicin, idarubicin, daunorubicin, epirubicin, busulfan, carmustine (BCNU), lomustine (CCNU), semustine, thalidomide, lenalidomide, methotrexate, azathioprine, 6-mercaptopurine, fludarabine, 5-azacytidine, pentostatin (2'-deoxycoformycin), cytarabine (cytosine arabinoside), gemcitabine, 5-fluorouracil, hydroxyurea, elesclomol, etoposide, teniposide, amsacrine, camptothecin, topotecan, irinotecan, chlorambucil, cyclophosphamide, ifosfamide, melphalan, bortezomib, vincristine, vinblastine, vinorelbine, paclitaxel, or docetaxel.

5. The polypeptide of claim 2, wherein said polypeptide is conjugated to cyclosporine A, tacrolimus (FK506), sirolimus (rapamycin), everolimus, temsirolimus, zotarolimus, or biolimus.

6. The polypeptide of claim 2, wherein said polypeptide is conjugated to G418, gentamicin, streptomycin, kanamycin, tobramycin, amikacin, arbekacin, neomycin, netilmicin, paromomycin, rhodostreptomycin, framycetin, ribostamycin, bekanamycin, dibekacin, spectinomycin, hygromycin B, sisomicin, isepamicin, astromicin, apramycin, amphotericin B, rifampicin, or pentamidine.

7. A method of producing a conjugate comprising coupling a radionuclide, an antibiotic, an immunosuppressant agent, or an anti-cancer agent to the polypeptide of claim 2 or a pharmaceutically acceptable salt thereof.

8. The method of claim 7, wherein said polypeptide has the sequence of any one of SEQ ID NOs: 4-13.

9. The method of claim 7, wherein said radionuclide is selected from $^{11}$C, $^{13}$N, $^{15}$O, $^{18}$F, $^{52}$Fe, $^{55}$Co, $^{61}$Cu, $^{62}$Cu, $^{64}$Cu, $^{67}$Cu, $^{67}$Ga, $^{68}$Ga, $^{62}$Zn, $^{63}$Zn, $^{70As}$, $^{71}$As, $^{74}$As, $^{76Br}$, $^{79}$Br, $^{82}$Rb, $^{86}$Y, $^{89}$Zr, $^{110}$In, $^{111}$In, $^{120}$I, $^{123}$I, $^{124}$I, $^{125}$I, $^{131}$I, $^{122}$Xe, $^{175}$Lu, $^{154}$Gd, $^{155}$Gd, $^{156}$Gd, $^{157}$Gd, $^{158}$Gd, $^{94m}$Tc, $^{94}$Tc, and $^{99m}$Tc.

10. The method of claim 7, wherein said anticancer agent is selected from cisplatin, carboplatin, oxaliplatin, bleomycin, mitomycin C, calicheamicins, maytansinoids, geldanamycin, doxorubicin, idarubicin, daunorubicin, epirubicin, busulfan, carmustine (BCNU), lomustine (CCNU), semustine, thalidomide, lenalidomide, methotrexate, azathioprine, 6-mercaptopurine, fludarabine, 5-azacytidine, pentostatin (2'-deoxycoformycin), cytarabine (cytosine arabinoside), gemcitabine, 5-fluorouracil, hydroxyurea, elesclomol, etoposide, teniposide, amsacrine, camptothecin, topotecan, irinotecan, chlorambucil, cyclophosphamide, ifosfamide, melphalan, bortezomib, vincristine, vinblastine, vinorelbine, paclitaxel, and docetaxel.

11. The method of claim 7, wherein said immunosuppressant agent is cyclosporine A, tacrolimus (FK506), sirolimus (rapamycin), everolimus, temsirolimus, zotarolimus, or biolimus.

12. The method of claim 7, wherein said antibiotic is G418, gentamicin, streptomycin, kanamycin, tobramycin, amikacin, arbekacin, neomycin, netilmicin, paromomycin, rhodostreptomycin, framycetin, ribostamycin, bekanamycin, dibekacin, spectinomycin, hygromycin B, sisomicin, isepamicin, astromicin, apramycin, amphotericin B, rifampicin, or pentamidine.

* * * * *